(12) United States Patent
Huggins et al.

(10) Patent No.: US 10,738,050 B2
(45) Date of Patent: Aug. 11, 2020

(54) 4H-PYRIDO[1,2-A]PYRIMIDIN-4-ONE COMPOUNDS

(71) Applicant: Prana Biotechnology Limited, Parkville (AU)

(72) Inventors: Penelope Jane Huggins, Murrumbeena (AU); Jack Gordon Parsons, Point Cook (AU); Kevin Jeffrey Barnham, Coburg (AU); Elisabeth Colette Louise Gautier, Hughesdale (AU); Antony Vincent Robinson, Athelstone (AU)

(73) Assignee: Prana Biotechnology Limited, Parkville, Victoria (AU)

( * ) Notice: Subject to any disclaimer, the term of this patent is extended or adjusted under 35 U.S.C. 154(b) by 0 days.

(21) Appl. No.: 16/409,296

(22) Filed: May 10, 2019

(65) Prior Publication Data

US 2019/0352301 A1 Nov. 21, 2019

Related U.S. Application Data

(63) Continuation of application No. 15/529,891, filed as application No. PCT/AU2015/000730 on Dec. 2, 2015, now Pat. No. 10,287,285.

(30) Foreign Application Priority Data

Dec. 2, 2014 (AU) .............................. 2014904868

(51) Int. Cl.
*C07D 239/00* (2006.01)
*C07D 471/04* (2006.01)
*A61K 31/519* (2006.01)
*C07D 498/14* (2006.01)
*C07F 1/08* (2006.01)
*C07F 3/06* (2006.01)

(52) U.S. Cl.
CPC .......... *C07D 471/04* (2013.01); *A61K 31/519* (2013.01); *C07D 498/14* (2013.01); *C07F 1/08* (2013.01); *C07F 3/06* (2013.01)

(58) Field of Classification Search
CPC ............................. C07D 239/00; C07D 471/04
See application file for complete search history.

(56) References Cited

U.S. PATENT DOCUMENTS

| 4,022,897 A | 5/1977 | Yale et al. |
| 4,291,036 A | 9/1981 | Knoll et al. |

FOREIGN PATENT DOCUMENTS

| EP | 2210892 A2 | 7/2010 |
| WO | 2006109084 A1 | 10/2006 |
| WO | 2007118276 A1 | 10/2007 |
| WO | 2007147217 A1 | 12/2007 |
| WO | 2010003533 A2 | 1/2010 |
| WO | 2010020647 A2 | 2/2010 |
| WO | 2010136778 A1 | 12/2010 |
| WO | 2011085990 A1 | 7/2011 |

OTHER PUBLICATIONS

Final Office Action in U.S. Appl. No. 15/529,891 dated Aug. 23, 2018, 6 pages.
Non-Final Office Action in U.S. Appl. No. 15/529,891 dated Apr. 4, 2018, 6 pages.
PCT International Preliminary Report on Patentability in PCT/AU2015/000730 dated Mar. 1, 2017, 64 pages.
PCT International Search Report in PCT/AU2015/000730 dated Feb. 8, 2016, 12 pages.
PCT Written Opinion in PCT/AU2015/000730 dated Feb. 8, 2016, 9 pages.
Alvarez, Salvador G., et al., "A Practical Procedure for the Synthesis of Alkyl Azides at Ambient Temperature in Dimethyl Sulfoxide in High Purity and Yield", Synthesis, Apr. 1997, pp. 413-414.
Barbeau, Olivier R., et al., "Quinolinone and pyridopyrimidinone inhibitors of DNA-dependent protein kinase", Org. Biomol. Chem., 2007, 5, 2670-2677.
Cebasek, Petra , et al., "Parallel Synthesis of 3-Amino-4H-Quinolizin-4-ones, Fused 3-Amino-4H-Pyrimidin-4-ones, and Fused 3-Amino-2H-Pyran-2-ones", J. Comb. Chem. 2006, 8, 95-102.
De La Vega De Leon, Antonio , et al., "Design of a Three-Dimensional Multitarget Activity Landscape", J. Chem. Inf. Model. 2012, 52, 2876-2883.
Ferrarini, Pier Luigi, et al., "Synthesis of Some 4H-Pyrido[I,2-a]Pyrimidin-4-Ones Investigated as Antimicrobial Agents", II Farmaco, 50 (1), 69-72 (1995).
Lombardo, Franco , et al., "ElogPoct: A Tool for Lipophilicity Determination in Drug Discovery", J. Med. Chem.v2000, 43, 2922-2928.

(Continued)

*Primary Examiner* — Bruck Kifle

(57) ABSTRACT

The present invention relates to compounds of the formula I or II: (I) (II) processes for their preparation and their use as pharmaceutical agents or compositions in the treatment, of neurological disorders.

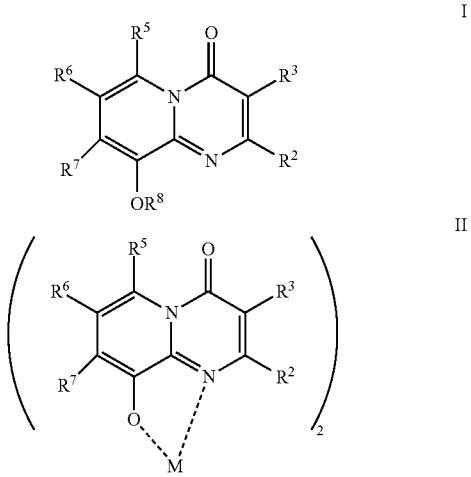

6 Claims, No Drawings

(56) References Cited

OTHER PUBLICATIONS

Smirnov, L. D., et al., "Structure and Reactivity of 2-Methyl-9-Hydroxy-4H-Pyrido[1,2-a]Pyrimidin-4-One", Scientific-Research Institute of Pharmacology, Russian Academy of Medical Sciences. Translated from Khimiya Geterosiklicheskikh Soedinenii, No. 12, pp. 1660-1666, Dec. 1992. Original Article submitted Feb. 11, 1991.
Wei, Yu-Feng, et al., "Aquabis(2-methyl-4-oxopyrido[1,2-a]-pyrimidin-9-olato)zinc(II) monohydrate", Acta Cryst. (2009). E65, m91, 7 pages.
Zhang, Huaihong, et al., "Aquabis(2,3-dimethyl-4-oxo-4H-pyrido-[1,2-a]pyrimidin-9-olato)nickel(II), and supporting information", Acta Cryst. (2010), E66, m5, 10 pages.
Zhang, Huaihong, et al., "Aquabis(2-methyl-4-oxopyrido[1,2-a]pyrimidin-9-olato)cobalt (II): Crystal Structure and Spectroscopic Properties", J. Chem. Crystallogr. (2011), vol. 41, pp. 715-720.

4H-PYRIDO[1,2-A]PYRIMIDIN-4-ONE COMPOUNDS

CROSS REFERENCE TO RELATED APPLICATIONS

This application is a continuation of U.S. patent application Ser. No. 15/529,891, filed May 25, 2017 and issued as U.S. Pat. No. 10,287,285 on May 14, 2019, which is a national stage entry of International Application No. PCT/AU2015/000730, filed Dec. 2, 2015, which claims priority to Australian Patent Application No. 2014904868, filed Dec. 2, 2014, the disclosures of which are incorporated by reference in their entireties.

TECHNICAL FIELD

The present invention relates generally to pyrido[1,2-a]pyrimidin-4-one compounds, processes for their preparation and their use as pharmaceutical agents or in compositions for the treatment of neurological disorders.

BACKGROUND

Neurological disorders including neurodegenerative disorders can undergo pathologically related reactions between proteins and the redox-active metal ions, such as zinc, copper or iron. These reactions generate reactive oxygen species (ROS), which have the capacity to damage cellular components by oxidizing proteins, lipid bilayers, and DNA. This can result in alterations of protein conformations, enzyme activities and cause protein aggregation.

ROS include free radicals such as superoxide anion, hydroxyl radical and other molecular species such as hydrogen peroxide (Bush and Goldstein (2001)). Hydroxyl radicals are the most reactive and damaging generated ROS. They are predominantly formed by a Fenton reaction between transition metals (usually iron(II) or copper(I)) and hydrogen peroxide.

Whilst cells possess antioxidant systems to protect against ROS damage, including protective enzymes such as copper-zinc superoxide dismutase, these enzymes contain metals. Cells must therefore maintain a careful balance between free and bound pro-oxidant versus antioxidant metal ions, which are critical to cellular homeostasis. It is generally considered that the aging brain has a slow and progressive imbalance between antioxidant defenses and intracellular concentrations of ROS.

There is a need to identify compounds designed to manage and modulate ionic biological metals that, when unregulated, have an established association with a growing number of diseases including those characterized by the presence of oxidative stress, protein aggregation and intracellular or extracellular metal imbalance.

SUMMARY

We have now found compounds which have two fused 6-membered rings with nitrogens at positions 1 and 5 and an $OR^8$ group at position 9 which are useful for treating neurological disorders. These compounds may possess one or more of the following properties: crosses the BBB, exhibits reduced adverse side effects and/or are stable in aqueous environments.

In a first aspect, there is provided a compound of formula I

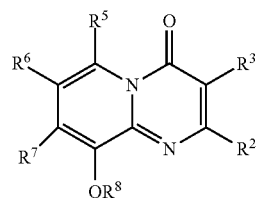

in which $R^2$ is H, $(CH_2)_n NR^9 R^{10}$, $C_{1-4}$ alkyl optionally interrupted with oxygen or $(CH_2)_n SC=SNR^9 R^{10}$;

$R^3$ is H, $C_{1-4}$ alkyl optionally interrupted with oxygen, $C_{1-4}$ alkoxy, $C_{3-6}$ cycloalkyl, $(CH_2)_m$ optionally substituted aryl, $(CH_2)_n$ optionally substituted aryl optionally fused with a 5 or 6 membered heterocyclyl, $C(O)NR^9 R^{10}$, $(CH_2)_n NR^9 R^{10}$ or $C(O)NH-N=CR^9 R^{10}$;

$R^5$ is H or $C_{1-4}$ alkyl;

$R^6$ is H, halo, $(CH_2)_n$ optionally substituted 5 or 6 membered heterocyclyl or $C_{2-4}$ alkynyl;

$R^7$ is H, halo, $(CH_2)_n$ 5 membered optionally substituted heterocyclyl, optionally substituted $C_{1-4}$ alkyl, $C_{2-4}$ alkynyl, $(CH_2)_n NR^9 R^{10}$, $NO_2$, $NR^5 SO_2$ optionally substituted aryl or $NR^5 SO_2$ optionally substituted $C_{1-4}$ alkyl;

$R^8$ is H, $SO_2$ optionally substituted aryl, $C_{1-4}$ alkyl or $(CH_2)_n$ aryl; or $R^7$ together with the carbon atom to which it is attached and $R^8$ together with the oxygen atom to which it is attached from a 5 membered ring;

$R^9$ and $R^{10}$ are independently selected from H, $C_{1-8}$ alkyl optionally interrupted with O, ON, $(CH_2)_n$ optionally substituted aryl optionally fused with a 5 or 6 membered heterocyclyl, $(CH_2)_n$ optionally substituted $C_{3-8}$ cycloalkyl, $(CH_2)_n$ optionally substituted 5 or 6 membered optionally substituted heterocyclyl, $SO_2$ optionally substituted aryl and $C_{1-4}$ alkoxy; or $R^9$ and $R^{10}$ together with the nitrogen atom to which they are attached form a 5 or 6 membered optionally substituted heterocyclyl;

X is N or CH;

m is 1, 2 or 3; and n is 0, 1, 2 or 3;

provided that:

(i) at least one of $R^2$, $R^3$, $R^5$, $R^6$ and $R^7$ is other than H;

(ii) when $R^3$ is $C_{1-4}$ alkyl and $R^2$, $R^5$ and $R^8$ are H, then $R^7$ or $R^6$ are other than H;

(iii) when $R^3$ is $C_{1-4}$ alkyl, $R^2$, $R^5$ and $R^8$ are H and $R^7$ is I, then $R^6$ is other than H, salts, isomers or prodrugs thereof or compounds selected from:

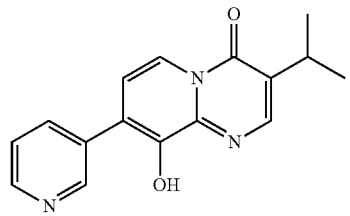

1596

-continued
1629 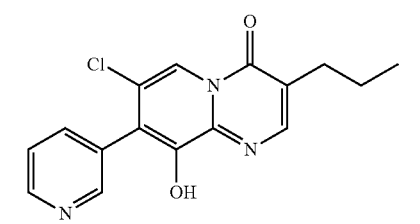
1639 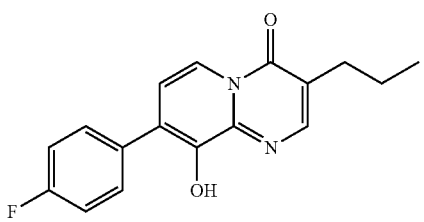
1641 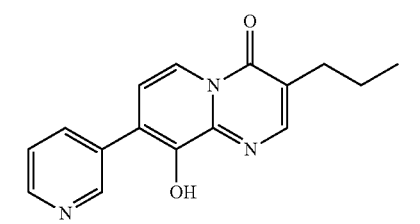
1655 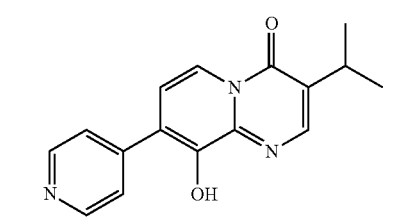
1659 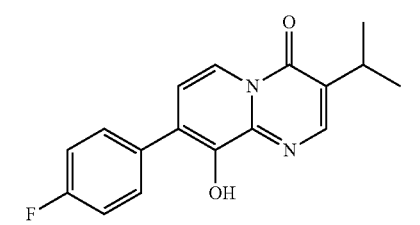
1668 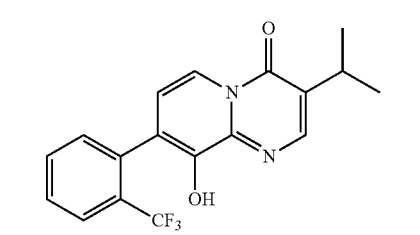
1671 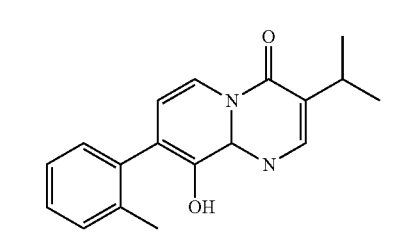
-continued
1680 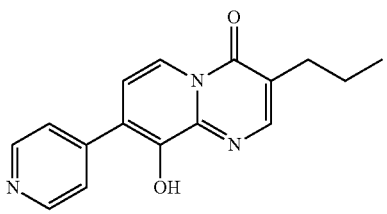
1681 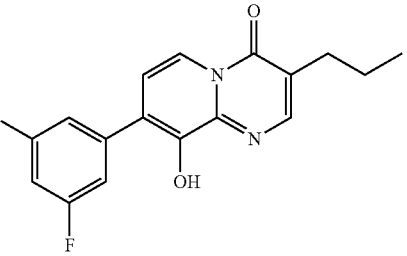
1683 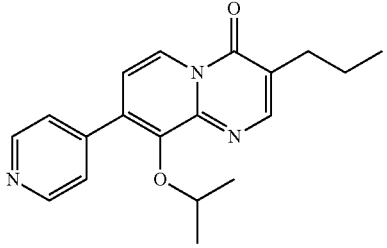
1649 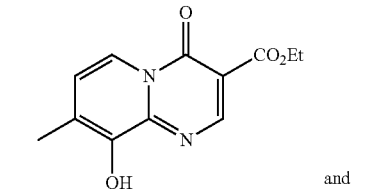
and
1710 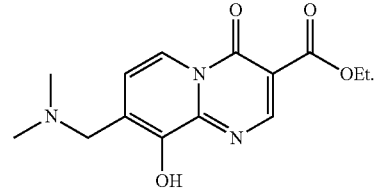
In a second aspect, there is provided a compound of formula II
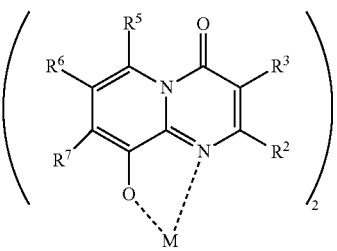
II
in which
R², R³, R⁵, R⁶ and R⁷ are as defined in formula I above; and
M is transition metal;
salts, isomers or prodrugs thereof.

In a third aspect, there is provided a process for the preparation of the compound of formula I, salts, isomers or prodrugs thereof defined above which comprises reacting a compound of formula III

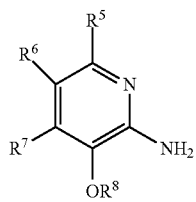

III in which
$R^5$, $R^6$, $R^7$ and $R^8$ are as defined in formula I above;
with a compound of formula IV

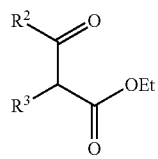

IV in which
$R^2$ and $R^3$ are as defined in formula I above;
to prepare a compound of formula V

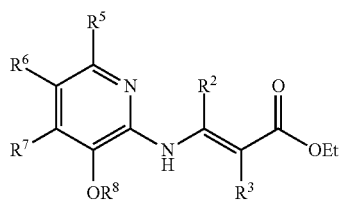

V in which
$R^2$, $R^3$, $R^5$, $R^6$, $R^7$ and $R^8$ are as defined in formula I above;
and cyclisation of the compound of formula V.

In a fourth aspect, there is provided a process for the preparation of the compound of formula II, salts, isomers or prodrugs thereof defined above which comprises reacting the compound of formula I, salts, isomers or prodrugs thereof defined above with a source of M in which M is as defined in formula II above.

In a fifth aspect, there is provided a pharmaceutical agent comprising the compound of formula I or II, salts, isomers or prodrugs thereof as defined above.

There is also provided a use of the compound of formula I or II, salts, isomers or prodrugs thereof as defined above as a pharmaceutical agent.

There is further provided the compound of formula I or II, salts, isomers or prodrugs thereof as defined above for use as a pharmaceutical agent.

The pharmaceutical agent may be a neurotherapeutic or neuroprotective agent.

In a sixth aspect, there is provided neurotherapeutic or neuroprotective agent comprising the compound of formula I or II, salts, isomers or prodrugs thereof as defined above.

There is also provided use of the compound of formula I or II, salts, isomers or prodrugs thereof as defined above as a neurotherapeutic or neuroprotective agent.

There is further provided the compound of formula I or II, salts, isomers or prodrugs thereof as defined above for use as a neurotherapeutic or neuroprotective agent.

The compound of formula I or II, salts, isomers or prodrugs thereof may be administered in the form of a pharmaceutical composition together with a pharmaceutically acceptable carrier.

In a seventh aspect, there is provided a pharmaceutical composition comprising the compound of formula I or II, salts, isomers or prodrugs thereof and a pharmaceutically acceptable carrier.

In one embodiment, the pharmaceutical composition additionally comprises a therapeutically effective amount of one or more further active agents such as a chemotherapeutic compound, immunotherapeutic compound, cytokine, genetic molecule and/or anesthetic.

In an eighth aspect, there is provided a method for the treatment of a neurological disorder which comprises administering an effective amount of the compound of formula I or II, salts, isomers or prodrugs thereof as defined above or the pharmaceutical agent or pharmaceutical composition defined above to a subject in need thereof.

There is also provided use of the compound of formula I or II, salts, isomers or prodrugs thereof as defined above or the pharmaceutical agent or pharmaceutical composition as defined above in the manufacture of a medicament for the treatment of a neurological disorder.

There is further provided use of the compound of formula I or II, salts, isomers or prodrugs thereof as defined above or the pharmaceutical composition as defined above for the treatment of a neurological disorder.

There is still further provided the compound of formula I or II, salts, isomers or prodrugs thereof as defined above or the pharmaceutical agent or pharmaceutical composition defined above for use in the treatment of a neurological disorder.

Although, the preferred subject is a human, the present invention has application in the veterinary and animal husbandry industries and hence extends to non-human animals.

DETAILED DESCRIPTION

Compounds

The present invention relates to compounds of formula I defined above.

In one embodiment, the compound of formula I is a compound of formula Ia

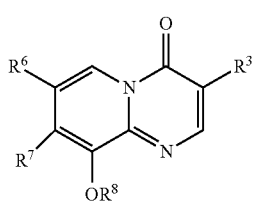

Ia in which $R^3$ and $R^5$ to $R^8$ are as defined in formula I above.

In one embodiment of formula Ia, $R^3$ is $C_{1-4}$ alkyl optionally interrupted with O, $C_{5-6}$ cycloalkyl, $(CH_2)_n$ optionally substituted aryl optionally fused with a 5 or 6 membered heterocyclyl, $C(O)NR^9R^{10}$ wherein $R^9$ is H and $R^{10}$ is $C_{1-6}$ alkyl, optionally substituted phenyl or optionally substituted 5 membered heterocyclyl; $R^6$ is H, halo such as Cl or Br, 5 membered heterocyclyl optionally substituted with benzyl or cyclopentyl, $C_{1-4}$alkyl or $C_{2-4}$alkynyl; $R^7$ is H, halo such as I, 5 or 6 membered optionally substituted heterocyclyl, optionally substituted phenyl, $(CH_2)NR^9R^{10}$, $C_{1-4}$alkyl, $C_{2-4}$alkynyl or $NR^5SO_2$ optionally substituted phenyl; and $R^8$ is H or $C_{1-4}$alkyl.

Representative examples of compounds of formula Ia include compounds 1235, 1607, 1621, 1622, 1623, 1624, 1643, 1599, 1611, 1650, 1674, 1675, 1685, 1686, 1596, 1597, 1600, 1601, 1602, 1603, 1605, 1629, 1630, 1633, 1639, 1641, 1648, 1651, 1652, 1653, 1654, 1655, 1656, 1659, 1660, 1668, 1671, 1680, 1681, 1683, 1627, 1631, 1632, 1640, 1642, 1645, 1647, 1679, 1691, 1693, 1706, 1606, 1615, 1616, 1617, 1626, 1613, 1619, 1620, 1625, 1628, 1644, 1658, 1664, 1669, 1682, 1704, 1710, 1712, 1722, 1657, 1660, 1661, 1717, 1708 and 1716 as shown in Schemes 1-4, 7-9 and 15-17 of Examples 1-4, 7-9 and 15-17.

In another embodiment, the compound of formula I is a compound of formula Ib

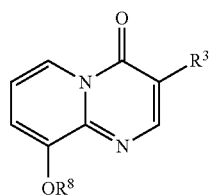

Ib in which $R^3$ and $R^8$ are as defined in formula I above

In one embodiment of formula Ib, $R^3$ is H, $C(O)NR^9R^{10}$ or $(C(O)N-NH=CR^9R^{10}$; and $R^8$ is H or benzyl.

Representative examples of compounds of formula Ib include 1394, 1422, 1423, 1425, 1426, 1427, 1428, 1429, 1431, 1432, 1433, 1436, 1437, 1440, 1441, 1445, 1446, 1447, 1450, 1452, 1453, 1454, 1461, 1462, 1532, 1533, 1649, 1723, 1724 and 1732 as shown in Schemes 5 and 13 of Examples 5 and 13.

In a further embodiment, the compound of formula I is a compound of formula Ic

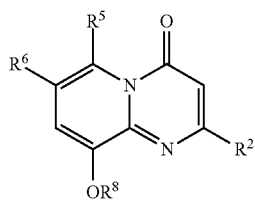

Ic in which $R^2$, $R^5$, $R^6$ and $R^8$ are as defined in formula I above.

In one embodiment of formula Ic, $R^2$ is $(CH_2)_nNR^9R^{10}$, $C_{1-4}$alkyl optionally interrupted with O or $(CH_2)_n$ SC=$SNR^9R^{10}$; $R^5$ is H or $C_{1-4}$alkyl such as methyl; and $R^6$ is halo such as Cl.

Representative examples of compounds of formula Ic include compounds 1400, 1401, 1402, 1403, 1404, 1405, 1406, 1407, 1408, 1409, 1410, 1411, 1412, 1413, 1414, 1415, 1416, 1417, 1418, 1435, 1438, 1439, 1442, 1443, 1444, 1448, 1449, 1451, 1455, 1456, 1457, 1458, 1459, 1463, 1464, 1466, 1467, 1468, 1469, 1470, 1471, 1476, 1478, 1479, 1485, 1490, 1491, 1500, 1503, 1504, 1506, 1508, 1515, 1516, 1517, 1518, 1519, 1521, 1522, 1523, 1525, 1527, 1531, 1604, 1608, 1609, 1610, 1612, 1614, 1618, 1634, 1635, 1636, 1637, 1638, 1670, 1699, 1707, 1591, 1646, 1701, 1705, 1713, 1714, 1720 and 1721 as shown in Schemes 6, 10 and 12 of Examples 6, 10 and 12.

In a still further embodiment, the compound of formula I is a compound of formula Id

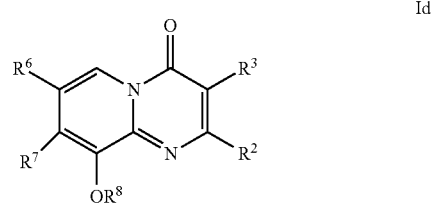

Id in which $R^2$, $R^3$ and $R^6$ to $R^8$ are as defined in formula I above.

In one embodiment of formula Id, $R^2$ is $C_{1-4}$alkyl such as methyl; $R^3$ is $C_{1-4}$alkyl or benzyl; $R^6$ is halo such as Cl; $R^7$ is halo such as I or 5 or 6 membered optionally substituted heterocyclyl; and $R^8$ is H or $C_{1-4}$alkyl such as propyl.

Representative examples of compounds of formula Id include compounds 1662, 1663, 1665, 1666, 1667, 1672, 1673, 1687, 1688, 1689, 1690, 1694 and 1698 as shown in Scheme 14 of Example 14.

In one embodiment, the compound of formula II is a compound of formula IIa.

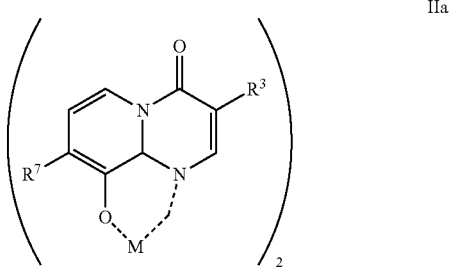

IIa in which
$R^3$, $R^7$ and M are as defined in formula II above.

In one embodiment of formula IIa, $R^3$ is $C_{1-4}$alkyl such as propyl or $C(O)NR^9R^{10}$; $R^7$ is $C_{1-4}$alkyl such as propyl and M is Zn or Cu.

Representative examples of compounds of formula IIa include compounds 1678, 1692, 1700, 1715, 1718, 1719, 1744, 1745 and 1748 as shown in Scheme 18 of Example 18.

Definitions

Unless otherwise herein defined, the following terms will be understood to have the general meanings which follow.

The term "$C_{1-6}$alkyl" refers to optionally substituted straight chain or branched chain hydrocarbon groups having from 1 to 6 carbon atoms. Examples include methyl (Me), ethyl (Et), propyl (Pr), isopropyl (i-Pr), butyl (Bu), isobutyl (i-Bu), sec-butyl (s-Bu), tert-butyl (t-Bu), pentyl, neopentyl, hexyl and the like. Unless the context requires otherwise, the term "$C_{1-6}$alkyl" also encompasses alkyl groups containing one less hydrogen atom such that the group is attached via two positions i.e. divalent. "$C_{1-4}$alkyl" and "$C_{1-3}$alkyl" including methyl, ethyl, propyl, isopropyl, n-butyl, isobutyl, sec-butyl and tert-butyl are preferred with methyl being particularly preferred.

The term "$C_{2-6}$alkenyl" refers to optionally substituted straight chain or branched chain hydrocarbon groups having at least one double bond of either E or Z stereochemistry where applicable and 2 to 6 carbon atoms. Examples include vinyl, 1-propenyl, 1- and 2-butenyl and 2-methyl-2-propenyl. Unless the context requires otherwise, the term "$C_{2-6}$alkenyl" also encompasses alkenyl groups containing one less hydrogen atom such that the group is attached via two positions i.e. divalent. "$C_{2-4}$alkenyl" and "$C_{2-3}$alkenyl" including ethenyl, propenyl and butenyl are preferred with ethenyl being particularly preferred.

The term "$C_{2-6}$alkynyl" refers to optionally substituted straight chain or branched chain hydrocarbon groups having at least one triple bond and 2 to 6 carbon atoms. Examples include ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl and 5-hexynyl and the like. Unless the context indicates otherwise, the term "$C_{2-6}$alkynyl" also encompasses alkynyl groups containing one less hydrogen atom such that the group is attached via two positions i.e. divalent. $C_{2-4}$alkynyl is preferred.

The term "$C_{3-8}$cycloalkyl" refers to non-aromatic cyclic groups having from 3 to 8 carbon atoms, including cyclopropyl, cyclobutyl, cyclopentyl, cyclohexyl, cycloheptyl and cyclooctyl. It will be understood that cycloalkyl groups may be saturated such as cyclohexyl or unsaturated such as cyclohexenyl. $C_{3-6}$cycloalkyl such as cyclopropyl, cyclobutyl, cyclopentyl and cyclohexyl are preferred.

The terms "hydroxy" and "hydroxyl" refer to the group —OH.

The term "$C_{1-6}$alkoxy" refers to an alkyl group as defined above covalently bound via an O linkage containing 1 to 6 carbon atoms, such as methoxy, ethoxy, propoxy, isoproxy, butoxy, tert-butoxy and pentoxy. "$C_{1-4}$alkoxy" and "$C_{1-3}$alkoxy" including methoxy, ethoxy, propoxy and butoxy are preferred with methoxy being particularly preferred.

The term "aryl" refers to a carbocyclic (non-heterocyclic) aromatic ring or mono-, bi- or tri-cyclic ring system. The aromatic ring or ring system is generally composed of 6 to 10 carbon atoms. Examples of aryl groups include but are not limited to phenyl, biphenyl, naphthyl and tetrahydronaphthyl. 6-membered aryls such as phenyl are preferred. The term "alkylaryl" refers to $C_{1-6}$alkylaryl such as benzyl.

The term "heterocyclyl" refers to a moiety obtained by removing a hydrogen atom from a ring atom of a heterocyclic compound which moiety has from 3 to 10 ring atoms (unless otherwise specified), of which 1, 2, 3 or 4 are ring heteroatoms each heteroatom being independently selected from O, S and N.

In this context, the prefixes 3-, 4-, 5-, 6-, 7-, 8-, 9- and 10-membered denote the number of ring atoms, or range of ring atoms, whether carbon atoms or heteroatoms. For example, the term "3-10 membered heterocyclyl", as used herein, pertains to a heterocyclyl group having 3, 4, 5, 6, 7, 8, 9 or 10 ring atoms. Examples of heterocyclyl groups include 5-6-membered monocyclic heterocyclyls and 9-10 membered fused bicyclic heterocyclyls.

Examples of monocyclic heterocyclyl groups include, but are not limited to, those containing one nitrogen atom such as aziridine (3-membered ring), azetidine (4-membered ring), pyrrolidine (tetrahydropyrrole), pyrroline (e.g., 3-pyrroline, 2,5-dihydropyrrole), 2H-pyrrole or 3H-pyrrole (isopyrrole, isoazole) or pyrrolidinone (5-membered rings), piperidine, dihydropyridine, tetrahydropyridine (6-membered rings), and azepine (7-membered ring); those containing two nitrogen atoms such as imidazoline, pyrazolidine (diazolidine), imidazoline, pyrazoline (dihydropyrazole) (5-membered rings), piperazine (6-membered ring); those containing one oxygen atom such as oxirane (3-membered ring), oxetane (4-membered ring), oxolane (tetrahydrofuran), oxole (dihydrofuran) (5-membered rings), oxane (tetrahydropyran), dihydropyran, pyran (6-membered rings), oxepin (7-membered ring); those containing two oxygen atoms such as dioxolane (5-membered ring), dioxane (6-membered ring), and dioxepane (7-membered ring); those containing three oxygen atoms such as trioxane (6-membered ring); those containing one sulfur atom such as thiirane (3-membered ring), thietane (4-membered ring), thiolane (tetrahydrothiophene) (5-membered ring), thiane (tetrahydrothiopyran) (6-membered ring), thiepane (7-membered ring); those containing one nitrogen and one oxygen atom such as tetrahydrooxazole, dihydrooxazole, tetrahydroisoxazole, dihydroisoxazole (5-membered rings), morpholine, tetrahydrooxazine, dihydrooxazine, oxazine (6-membered rings); those containing one nitrogen and one sulfur atom such as thiazoline, thiazolidine (5-membered rings), thiomorpholine (6-membered ring); those containing two nitrogen and one oxygen atom such as oxadiazine (6-membered ring); those containing one oxygen and one sulfur such as: oxathiole (5-membered ring) and oxathiane (thioxane) (6-membered ring); and those containing one nitrogen, one oxygen and one sulfur atom such as oxathiazine (6-membered ring).

Heterocyclyls also encompass aromatic heterocyclyls and non-aromatic heterocyclyls. Such groups may be substituted or unsubstituted.

The term "aromatic heterocyclyl" may be used interchangeably with the term "heteroaromatic" or the term "heteroaryl" or "hetaryl". The heteroatoms in the aromatic heterocyclyl group may be independently selected from N, S and O.

"Heteroaryl" is used herein to denote a heterocyclic group having aromatic character and embraces aromatic monocyclic ring systems and polycyclic (e.g. bicyclic) ring systems containing one or more aromatic rings. The term aromatic heterocyclyl also encompasses pseudoaromatic heterocyclyls. The term "pseudoaromatic" refers to a ring system which is not strictly aromatic, but which is stabilized by means of delocalization of electrons and behaves in a similar manner to aromatic rings. The term aromatic heterocyclyl therefore covers polycyclic ring systems in which all of the fused rings are aromatic as well as ring systems where one or more rings are non-aromatic, provided that at least one ring is aromatic. In polycyclic systems containing both aromatic and non-aromatic rings fused together, the group may be attached to another moiety by the aromatic ring or by a non-aromatic ring.

Examples of heteroaryl groups are monocyclic and bicyclic groups containing from five to ten ring members. The heteroaryl group can be, for example, a five membered or six membered monocyclic ring or a bicyclic structure formed from fused five and six membered rings or two fused six membered rings or two fused five membered rings. Each ring may contain up to about four heteroatoms typically selected from nitrogen, sulphur and oxygen. The heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Aromatic heterocyclyl groups may be 5-membered or 6-membered mono-cyclic aromatic ring systems.

Examples of 5-membered monocyclic heteroaryl groups include but are not limited to furanyl, thienyl, pyrrolyl, oxazolyl, oxadiazolyl (including 1,2,3 and 1,2,4 oxadiazolyls and furazanyl i.e. 1,2,5-oxadiazolyl), thiazolyl, isoxazolyl, isothiazolyl, pyrazolyl, imidazolyl, triazolyl (including 1,2,3, 1,2,4 and 1,3,4 triazolyls), oxatriazolyl, tetrazolyl, thiadiazolyl (including 1,2,3 and 1,3,4 thiadiazolyls) and the like.

Examples of 6-membered monocyclic heteroaryl groups include but are not limited to pyridinyl, pyrimidinyl, pyridazinyl, pyrazinyl, triazinyl, pyranyl, oxazinyl, dioxinyl, thiazinyl, thiadiazinyl and the like. Examples of 6-membered aromatic heterocyclyls containing nitrogen include pyridyl (1 nitrogen), pyrazinyl, pyrimidinyl and pyridazinyl (2 nitrogens).

Aromatic heterocyclyl groups may also be bicyclic or polycyclic heteroaromatic ring systems such as fused ring systems (including purine, pteridinyl, napthyridinyl, 1H thieno[2,3-c]pyrazolyl, thieno[2,3-b]furyl and the like) or linked ring systems (such as oligothiophene, polypyrrole and the like). Fused ring systems may also include aromatic 5-membered or 6-membered heterocyclyls fused to carbocyclic aromatic rings such as phenyl, napthyl, indenyl, azulenyl, fluorenyl, anthracenyl and the like, such as 5-membered aromatic heterocyclyls containing nitrogen fused to phenyl rings, 5-membered aromatic heterocyclyls containing 1 or 2 nitrogens fused to phenyl ring.

A bicyclic heteroaryl group may be, for example, a group selected from: a) a benzene ring fused to a 5- or 6-membered ring containing 1, 2 or 3 ring heteroatoms; b) a pyridine ring fused to a 5- or 6-membered ring containing 1, 2 or 3 ring heteroatoms; c) a pyrimidine ring fused to a 5- or 6-membered ring containing 1 or 2 ring heteroatoms; d) a pyrrole ring fused to a 5- or 6-membered ring containing 1, 2 or 3 ring heteroatoms; e) a pyrazole ring fused to a 5- or 6-membered ring containing 1 or 2 ring heteroatoms; f) an imidazole ring fused to a 5- or 6-membered ring containing 1 or 2 ring heteroatoms; g) an oxazole ring fused to a 5- or 6-membered ring containing 1 or 2 ring heteroatoms; h) an isoxazole ring fused to a 5- or 6-membered ring containing 1 or 2 ring heteroatoms; i) a thiazole ring fused to a 5- or 6-membered ring containing 1 or 2 ring heteroatoms; j) an isothiazole ring fused to a 5- or 6-membered ring containing 1 or 2 ring heteroatoms; k) a thiophene ring fused to a 5- or 6-membered ring containing 1, 2 or 3 ring heteroatoms; l) a furan ring fused to a 5- or 6-membered ring containing 1, 2 or 3 ring heteroatoms; m) a cyclohexyl ring fused to a 5- or 6-membered ring containing 1, 2 or 3 ring heteroatoms; and n) a cyclopentyl ring fused to a 5- or 6-membered ring containing 1, 2 or 3 ring heteroatoms.

Particular examples of bicyclic heteroaryl groups containing a five membered ring fused to another five membered ring include but are not limited to imidazothiazole (e.g. imidazo[2,1-b]thiazole) and imidazoimidazole (e.g. imidazo[1,2-a]imidazole).

Particular examples of bicyclic heteroaryl groups containing a six membered ring fused to a five membered ring include but are not limited to benzofuran, benzothiophene, benzimidazole, benzoxazole, isobenzoxazole, benzisoxazole, benzothiazole, benzisothiazole, isobenzofuran, indole, isoindole, indolizine, indoline, isoindoline, purine (e.g., adenine, guanine), indazole, pyrazolopyrimidine (e.g. pyrazolo[1,5-a]pyrimidine), benzodioxole and pyrazolopyridine (e.g. pyrazolo[1,5-a]pyridine) groups. A further example of a six membered ring fused to a five membered ring is a pyrrolopyridine group such as a pyrrolo[2,3-b]pyridine group.

Particular examples of bicyclic heteroaryl groups containing two fused six membered rings include but are not limited to quinoline, isoquinoline, chroman, thiochroman, chromene, isochromene, isochroman, benzodioxan, quinolizine, benzoxazine, benzodiazine, pyridopyridine, quinoxaline, quinazoline, cinnoline, phthalazine, naphthyridine and pteridine groups.

Examples of heteroaryl groups containing an aromatic ring and a non-aromatic ring include tetrahydronaphthalene, tetrahydroisoquinoline, tetrahydroquinoline, dihydrobenzothiophene, dihydrobenzofuran, 2,3-dihydro-benzo[1,4]dioxine, benzo[1,3]dioxole, 4,5,6,7-tetrahydrobenzofuran, indoline, isoindoline and indane groups.

Examples of aromatic heterocyclyls fused to carbocyclic aromatic rings may therefore include but are not limited to benzothiophenyl, indolyl, isoindolyl, benzofuranyl, isobenzofuranyl, benzimidazolyl, indazolyl, benzoxazolyl, benzisoxazolyl, isobenzoxazoyl, benzothiazolyl, benzisothiazolyl, quinolinyl, isoquinolinyl, quinoxalinyl, quinazolinyl, cinnolinyl, benzotriazinyl, phthalazinyl, carbolinyl and the like.

The term "non-aromatic heterocyclyl" encompasses optionally substituted saturated and unsaturated rings which contain at least one heteroatom selected from the group consisting of N, S and O.

Non-aromatic heterocyclyls may be 3-7 membered monocyclic rings.

Examples of 5-membered non-aromatic heterocyclyl rings include 2H-pyrrolyl, 1-pyrrolinyl, 2-pyrrolinyl, 3-pyrrolinyl, pyrrolidinyl, 1-pyrrolidinyl, 2-pyrrolidinyl, 3-pyrrolidinyl, tetrahydrofuranyl, tetrahydrothiophenyl, pyrazolinyl, 2-pyrazolinyl, 3-pyrazolinyl, pyrazolidinyl, 2-pyrazolidinyl, 3-pyrazolidinyl, imidazolidinyl, 3-dioxalanyl, thiazolidinyl, isoxazolidinyl, 2-imidazolinyl and the like.

Examples of 6-membered non-aromatic heterocyclyls include piperidinyl, piperidinonyl, pyranyl, dihyrdopyranyl, tetrahydropyranyl, 2H pyranyl, 4H pyranyl, thianyl, thianyl oxide, thianyl dioxide, piperazinyl, diozanyl, 1,4-dioxinyl, 1,4-dithianyl, 1,3,5-triozalanyl, 1,3,5-trithianyl, 1,4-morpholinyl, thiomorpholinyl, 1,4-oxathianyl, triazinyl, 1,4-thiazinyl and the like.

Examples of 7-membered non-aromatic heterocyclyls include azepanyl, oxepanyl, thiepanyl and the like.

Non-aromatic heterocyclyl rings may also be bicyclic heterocyclyl rings such as linked ring systems (for example uridinyl and the like) or fused ring systems. Fused ring systems include non-aromatic 5-membered, 6-membered or 7-membered heterocyclyls fused to carbocyclic aromatic rings such as phenyl, napthyl, indenyl, azulenyl, fluorenyl, anthracenyl and the like. Examples of non-aromatic 5-membered, 6-membered or 7-membered heterocyclyls fused to carbocyclic aromatic rings include indolinyl, benzodiazepinyl, benzazepinyl, dihydrobenzofuranyl and the like.

The term "halo" refers to fluoro, chloro, bromo or iodo.

The term "optionally substituted" refers to a group that may or may not be further substituted with one or more groups selected from $C_{1-6}$ alkyl, $C_{3-6}$ cycloalkyl, $C_{2-6}$ alkenyl, $C_{2-6}$ alkynyl, aryl, heterocyclyl, halo, halo$C_{1-6}$alkyl, $CF_3$, halo$C_{3-6}$cycloalkyl, halo$C_{2-6}$alkenyl, halo$C_{2-6}$alkynyl, haloaryl, haloheterocycylyl, hydroxy, $C_{1-6}$ alkoxy, $OCF_3$, $C_{2-6}$alkenyloxy, $C_{2-6}$alkynyloxy, aryloxy, heterocyclyoxy, carboxy, halo$C_{1-6}$alkoxy, halo$C_{2-6}$alkenyloxy, halo$C_{2-6}$alkynyloxy, haloaryloxy, nitro, nitro$C_{0-6}$alkyl, nitro$C_{2-6}$alkenyl, nitroaryl, nitroheterocyclyl, azido, amino, $C_{1-6}$alkylamino, $C_{2-6}$alkenylamino, $C_{2-6}$alkynylamino, arylamino, heterocyclylamino acyl, $C_{1-6}$alkylacyl, $C_{2-6}$alkenylacyl, $C_{2-6}$alkynylacyl, arylacyl, heterocyclylacyl, acylamino, acyloxy, aldehydo, $C_{1-6}$alkylsulphonyl, arylsulphonyl, $C_{1-6}$alkylsulphonylamino, arylsulphonylamino, $C_{1-6}$alkylsulphonyloxy, arylsulphonyloxy, $C_{1-6}$alkylsulphenyl, $C_{2-6}$alklysulphenyl, arylsulphenyl, carboalkoxy, carboaryloxy, mercapto, $C_{1-6}$alkylthio, arylthio, acylthio, cyano and the like. Preferably, the optional substituent is $C_{1-4}$ alkyl, $CF_3$, hydroxy, halo such as Cl or F, $C_{1-4}$ alkoxy such as methoxy or $OCF_3$.

It will be understood that suitable derivatives of aromatic heterocyclyls containing nitrogen include N-oxides thereof.

The salts of the compounds of formula I or II are preferably pharmaceutically acceptable, but it will be appreciated that non-pharmaceutically acceptable salts also fall within the scope of the present invention, since these are useful as intermediates in the preparation of pharmaceutically acceptable salts. Examples of pharmaceutically acceptable salts include salts of pharmaceutically acceptable cations such as sodium, potassium, lithium, calcium, magnesium, ammonium and alkylammonium; acid addition salts of pharmaceutically acceptable inorganic acids such as hydrochloric, orthophosphoric, sulphuric, phosphoric, nitric, carbonic, boric, sulfamic and hydrobromic acids; or salts of pharmaceutically acceptable organic acids such as acetic, propionic, butyric, tartaric, maleic, hydroxymaleic, fumaric, citric, lactic, mucic, gluconic, benzoic, succinic, oxalic, phenylacetic, methanesulphonic, trihalomethanesulphonic, toluenesulphonic, benzenesulphonic, salicylic, sulphanilic, aspartic, glutamic, edetic, stearic, palmitic, oleic, lauric, pantothenic, tannic, ascorbic and valeric acids. Salts of amine groups may also comprise quaternary ammonium salts in which the amino nitrogen atom carries a suitable organic group such as an alkyl, alkenyl, alkynyl or aralkyl moiety.

The salts may be formed by conventional means, such as by reacting the free base form of the compound with one or more equivalents of the appropriate acid.

It should be understood that a reference to a pharmaceutically acceptable salt includes the solvent addition forms or crystal forms thereof, particularly solvates or polymorphs. Solvates contain either stoichiometric or non-stoichiometric amounts of a solvent, and may be formed during the process of crystallization with pharmaceutically acceptable solvents such as water, alcohols such as methanol, ethanol or isopropyl alcohol, DMSO, acetonitrile, dimethyl formamide (DMF) and the like with the solvate forming part of the crystal lattice by either non-covalent binding or by occupying a hole in the crystal lattice. Hydrates are formed when the solvent is water, alcoholates are formed when the solvent is alcohol. Solvates of the compounds of the present invention can be conveniently prepared or formed during the processes described herein. In general, the solvated forms are considered equivalent to the unsolvated forms for the purposes of the compounds and methods provided herein.

Additionally, the compounds of the present invention can exist in unsolvated as well as solvated forms with pharmaceutically acceptable solvents such as water, ethanol, and the like. The solvated forms of the compounds of the present invention are also considered to be disclosed herein.

It will be understood that compounds of formula I or II may possess a chiral centre and may therefore exist as an isomer such as a racemate or an R- or S-enantiomer. The compounds may therefore be used as a purified enantiomer or diastereomer, or as a mixture of any ratio thereof. The isomers may be separated conventionally by chromatographic methods or using a resolving agent. Alternatively the individual isomers may be prepared by asymmetric synthesis using chiral intermediates. Where the compound has a carbon-carbon double bond, it may occur in Z- or E-form and all isomeric forms of the compounds being included in the present invention.

This invention also encompasses prodrugs of the compounds of formula I or II.

A prodrug may be a pharmacologically inactive derivative of the active compound that requires transformation within the body in order to release the active compound, and that has improved delivery properties over the active compound. The transformation in vivo may be, for example, as the result of some metabolic process, such as chemical or enzymatic hydrolysis of a carboxylic, phosphoric or sulphate ester, or reduction or oxidation of a susceptible functionality. In one embodiment, the $OR^8$ group on the compounds of formula (I) may be blocked to form a prodrug when $R^8$ is H, in particular an ester prodrug. The hydroxy group represents a principal site of metabolism for the compounds: conjugation with glucose glucuronic acid or sulphate gives a hydrophilic species ready to be excreted.

Included within the scope of this invention are compounds of the formula I or II to which at least one of a detectable label, an affinity tag and a photoreactive group is linked.

Methods of Treatment

The compounds of formula (I) may be used in the treatment of a neurological disorder.

Generally, the term "treatment" means affecting a subject, tissue or cell to obtain a desired pharmacological and/or physiological effect and includes: (a) inhibiting the neurological disorder, i.e. arresting its development or further development; (b) relieving or ameliorating the effects of the neurological disorder, i.e. cause regression of the effects of the neurological disorder; (c) reducing the incidence or the neurological disorder or (d) preventing the disorder from occurring in a subject, tissue or cell predisposed to the neurological disorder or at risk thereof, but has not yet been diagnosed with a protective pharmacological and/or physiological effect so that the neurological disorder does not develop or occur in the subject, tissue or cell.

The term "subject" as used herein refers to any animal, in particular mammals such as humans having a disease or condition which requires treatment with the compound of formula I or II.

The term "administering" refers to providing the compound or pharmaceutical composition of the invention to a subject suffering from or at risk of the diseases or conditions to be treated or prevented.

The term "neurological disorders" is used herein in its broadest sense and refers to disorders in which various cell types of the nervous system are degenerated and/or have been damaged as a result of neurodegenerative disorders or injuries or exposures. In particular, compounds of formula I or II can be used for the treatment of resulting disorders, in which damage to cells of the nervous system has occurred due to surgical interventions, infections, exposure to toxic agents, tumours, nutritional deficits or metabolic disorders.

The term "neurodegenerative disorder" as used herein refers to an abnormality in which neuronal integrity is threatened. Neuronal integrity can be threatened when neuronal cells display decreased survival or when the neurons can no longer propagate a signal.

Additionally, the compounds of formula I or II may also be used to potentiate the effects of other treatments, for example to potentiate the neuroprotective effects of brain derived nerve growth factor.

The term "diseases characterized by metal imbalance" refers to a disease whereby a subject has either a too high or too low total amount of metal. This term also refers to a subject with a normal total amount of metal, but the metal is not correctly or is abnormally distributed.

The term "diseases characterized by the presence of oxidative stress" refers to a disease whereby biological constituents of a subject are damaged by reactive oxygen species. It is particularly contemplated that such consistuents are damaged by reactive oxygen species such as the hydroxyl radical, hydrogen peroxide and superoxide produced in Fenton's and similar reactions. In particular it is understood that metals such as iron, copper, zinc, chromium, vanadium and cobalt are capable of redox cycling in which a single electron may be accepted or donated by the metal, facilitating oxidative reactions. Actual damage results when the oxidative species causes modifications of amino acids (e.g. meta-tyrosine and ortho-tyrosine formation from phenylalanine), carbohydrates and lipids (inducing peroxidation). In some cases such modification may cause a toxic gain of function or corruption of the biological consistuent substrate.

Reference to an "agent" includes combinations of two or more active agents. A "combination" also includes multi-part such as a two-part composition where the agents are provided separately and given or dispensed separately or admixed together prior to dispensation. For example, a multi-part pharmaceutical pack may have two or more agents separately maintained. Hence, this aspect of the present invention includes combination therapy. Combination therapy includes the co-administration of an agent and another active such as a chemotherapeutic compound, immunotherapeutic compound, cytokine, genetic molecule and/or an anesthetic.

Dosages

The terms "effective amount" and "therapeutically effective amount" of an agent as used herein mean a sufficient amount of the agent to provide the desired therapeutic or physiological or effect or outcome. Such an effect or outcome includes inhibiting the growth or viability of cells associated with a glioma in the brain. Undesirable effects, e.g. side effects, are sometimes manifested along with the desired therapeutic effect; hence, a practitioner balances the potential benefits against the potential risks in determining what is an appropriate "effective amount". The exact amount required will vary from subject to subject, depending on the species, age and general condition of the subject, mode of administration and the like. Thus, it may not be possible to specify an exact "effective amount". However, an appropriate "effective amount" in any individual case may be determined by one of ordinary skill in the art using only routine experimentation.

The effective amount is deemed the amount required to inhibit the growth or viability of cells associated with a glioma. Effective amounts include from about 1 ng to about 1 g/subject administration. The administration may be a single dose or a series of divided doses. Amounts include from about 5 ng to about 800 mg/subject administration. Actual amounts include about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 ng or 200, 300, 400, 500, 600, 700, 800, 900, 1000 ng or 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 mg or 200, 300, 400, 500, 600, 700, 800, 900, 1000 mg per subject.

Pharmaceutical Compositions

The compositions of the present invention comprise at least one of the compounds of formula I or II together with one or more pharmaceutically acceptable carriers and optionally other therapeutic agents. Each carrier must be pharmaceutically "acceptable" in the sense of being compatible with the other ingredients of the formulations and not injurious to the subject. Carriers may include excipients and other additives such as diluents, detergents, coloring agents, wetting or emulsifying agents, pH buffering agents, preservatives, and the like. Compositions include those suitable for oral, rectal, nasal, topical (including buccal and sublingual), vaginal or parenteral (including subcutaneous, intramuscular, intravenous and intradermal) administration. The compositions may conveniently be presented in unit dosage form and may be prepared by methods well known in the art of pharmacy. Such methods include the step of bringing into association the active ingredient with the carrier which constitutes one or more accessory ingredients. In general, the formulations are prepared by uniformly and intimately bringing into association the active ingredient with liquid carriers, diluents, adjuvants and/or excipients or finely divided solid carriers or both, and then if necessary shaping the product.

The compounds of formula I or II may be administered orally, topically, or parenterally in dosage unit formulations containing conventional non-toxic pharmaceutically acceptable carriers, adjuvants, and vehicles. The term parenteral as used herein includes subcutaneous injections, aerosol for administration to lungs or nasal cavity, intravenous, intramuscular, intrathecal, intracranial, injection, intraocular or infusion techniques.

The present invention also provides suitable topical, oral, and parenteral pharmaceutical compositions for use in the novel methods of treatment of the present invention. The compounds of the present invention may be administered orally as tablets, aqueous or oily suspensions, lozenges, troches, powders, granules, emulsions, capsules, syrups or elixirs. The compositions for oral use may contain one or more agents selected from the group of sweetening agents, flavoring agents, coloring agents and preserving agents in order to produce pharmaceutically elegant and palatable preparations. Suitable sweeteners include sucrose, lactose, glucose, aspartame or saccharin. Suitable disintegrating agents include corn starch, methylcellulose, polyvinylpyrrolidone, xanthan gum, bentonite, alginic acid or agar. Suitable flavoring agents include peppermint oil, oil of wintergreen, cherry, orange or raspberry flavoring. Suitable preservatives include sodium benzoate, vitamin E, alphatocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate. The tablets contain the active ingredient in admixture with non-toxic pharmaceutically acceptable excipients which are suitable for the manufacture of tablets.

These excipients may be, for example, (1) inert diluents, such as calcium carbonate, lactose, calcium phosphate or sodium phosphate; (2) granulating and disintegrating agents, such as corn starch or alginic acid; (3) binding agents, such as starch, gelatin or acacia; and (4) lubricating agents, such as magnesium stearate, stearic acid or talc. These tablets may be uncoated or coated by known techniques to delay disintegration and absorption in the gastrointestinal tract and thereby provide a sustained action over a longer period. For example, a time delay material such as glyceryl monostearate or glyceryl distearate may be employed. Coating may also be performed using techniques described in the U.S. Pat. Nos. 4,256,108; 4,160,452; and 4,265,874 to form osmotic therapeutic tablets for control release.

The above compounds as well as the pharmaceutically-active agent useful in the method of the invention can be administered, for in vivo application, parenterally by injection or by gradual perfusion over time independently or together. Administration may be intra-ocular, intravenously, intraarterial, intraperitoneally, intramuscularly, subcutaneously, intracavity, transdermally or infusion by, for example, osmotic pump. For in vitro studies the agents may be added or dissolved in an appropriate biologically acceptable buffer and added to a cell or tissue.

Compositions for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives may also be present such as, for example, antimicrobials, anti-oxidants, attenuating agents, growth factors and inert gases and the like.

The present invention includes various pharmaceutical compositions useful for ameliorating disease. The pharmaceutical compositions according to one embodiment of the invention are prepared by bringing an above compound, analogs, derivatives or salts thereof, or combinations of the above compounds and one or more pharmaceutically-active agents into a form suitable for administration to a subject using carriers, excipients and additives or auxiliaries. Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Preservatives include antimicrobial, anti-oxidants, attenuating agents and inert gases. Other pharmaceutically acceptable carriers include aqueous solutions, non-toxic excipients, including salts, preservatives, buffers and the like, as described, for instance, in Remington's Pharmaceutical Sciences, 20th ed. Williams and Wilkins (2000) and The British National Formulary 43rd ed. (British Medical Association and Royal Pharmaceutical Society of Great Britain, 2002; http://bnf.rhn.net), the contents of which are hereby incorporated by reference. The pH and exact concentration of the various components of the pharmaceutical compositions are adjusted according to routine skills in the art. See Goodman and Gilman's The Pharmacological Basis for Therapeutics (7th ed., 1985).

The pharmaceutical compositions are preferably prepared and administered in dose units. Solid dose units may be tablets, capsules and suppositories. For treatment of a subject, depending on activity of the compound, manner of administration, nature and severity of the disorder, age and body weight of the subject, different daily doses can be used. Under certain circumstances, however, higher or lower daily doses may be appropriate. The administration of the daily dose can be carried out both by single administration in the form of an individual dose unit or else several smaller dose units and also by multiple administration of subdivided doses at specific intervals.

The pharmaceutical compositions may be administered locally or systemically in a therapeutically effective dose. Amounts effective for this use will, of course, depend on the severity of the disease and the weight and general state of the subject. Typically, dosages used in vitro may provide useful guidance in the amounts useful for in situ administration of the pharmaceutical composition, and animal models may be used to determine effective dosages for treatment of the cytotoxic side effects. Various considerations are described, e.g., in Langer, Science, 249:1527, 1990.

Compositions for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, such as peanut oil, liquid paraffin or olive oil.

Aqueous suspensions normally contain the active materials in admixture with excipients suitable for the manufacture of aqueous suspension. Such excipients may be (1) suspending agent such as sodium carboxymethylcellulose, methyl cellulose, hydroxypropylmethylcellulose, sodium alginate, polyvinylpyrrolidone, gum tragacanth and gum acacia; (2) dispersing or wetting agents which may be (a) naturally occurring phosphatide such as lecithin; (b) a condensation product of an alkylene oxide with a fatty acid, for example, polyoxyethylene stearate; (c) a condensation product of ethylene oxide with a long chain aliphatic alcohol, for example, heptadecaethylenoxycetanol; (d) a condensation product of ethylene oxide with a partial ester derived from a fatty acid and hexitol such as polyoxyethylene sorbitol monooleate, or (e) a condensation product of ethylene oxide with a partial ester derived from fatty acids and hexitol anhydrides, for example polyoxyethylene sorbitan monooleate.

The pharmaceutical compositions may be in the form of a sterile injectable aqueous or oleagenous suspension. This suspension may be formulated according to known methods using those suitable dispersing or wetting agents and suspending agents which have been mentioned above. The sterile injectable preparation may also a sterile injectable solution or suspension in a non-toxic parenterally-acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

The above compounds may also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

The compounds may also be presented for use in the form of veterinary compositions, which may be prepared, for example, by methods that are conventional in the art. Examples of such veterinary compositions include those adapted for:

(a) oral administration, external application, for example drenches (e.g. aqueous
or non-aqueous solutions or suspensions); tablets or boluses; powders, granules or pellets for admixture with feed stuffs; pastes for application to the tongue;

(b) parenteral administration for example by subcutaneous, intramuscular or intravenous injection, e.g. as a sterile solution or suspension; or (when appropriate) by intramammary injection where a suspension or solution is introduced in the udder via the teat;

(c) topical applications, e.g. as a cream, ointment or spray applied to the skin;
or
(d) intravaginally, e.g. as a pessary, cream or foam.

EXAMPLES

The present invention is further described by the following non-limiting Examples.

Example 1

Scheme 1

Substituted 9-hydroxy-4H-pyrido[1,2-a]pyrimidin-4-ones can be prepared by the synthetic route depicted in Scheme 1. Starting from an ester intermediate 1-1, reaction with LDA at low temperature generates the enolate anion which is quenched with ethyl formate to afford the aldehyde 1-2. Heating the aldehyde to reflux with a 3-hydroxypyridinol 1-3 generates an ester 1-4. Cyclisation of 1-4 in boiling acetic acid provides after crystallization, the desired target compounds 1-5 (Scheme 1).

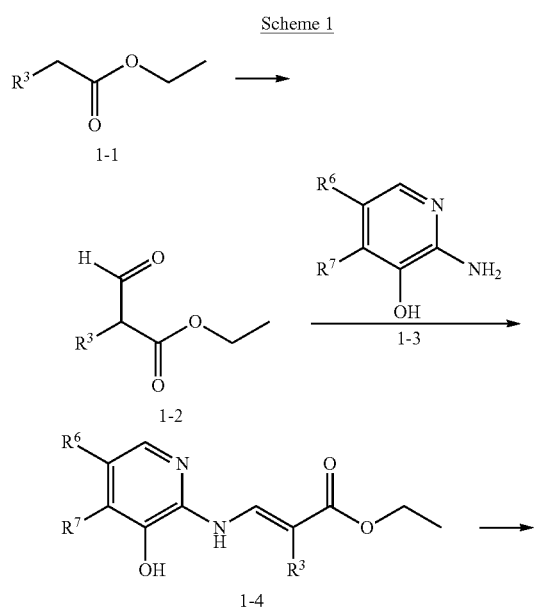

Scheme 1

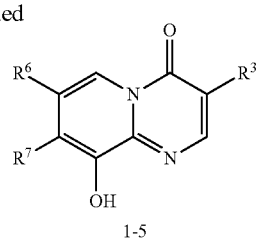

1-5 in which $R^3$ is $C_{1-4}$alkyl optionally interrupted with O, $C_{5-6}$cycloalkyl or benzyl optionally fused with a 5 membered O containing heterocyclyl;
$R^6$ is Cl or Br; and
$R^7$ is I.

Compound 1621

Ethyl-2-cyclohexyl-3-oxopropanoate (1-2)

Ethyl-2-cyclohexyl acetate (7.5 g, 44 mmol) was dissolved in anhydrous THF (20 mL) and then added to a solution of LDA (28.6 mL, 2.0 M solution in heptane/THF/ethylbenzene) at −78° C. After stirring at this temperature for 1 h, ethyl formate (4.8 mL, 59 mmol) was added and the reaction was warmed to rt over 3 h. The reaction was quenched carefully with $H_2O$ then THF was removed on a rotary evaporator. The mixture was then extracted with petroleum spirits 60-80° C. (×3). The aqueous layer was then acidified to pH 2 with conc. HCl and extracted into $CH_2Cl_2$ (×2). The organic extracts were dried over $Na_2SO_4$, filtered and concentrated to furnish the desired aldehyde 1-2 as an orange oil (5.65 g, 65%). $^1$H NMR (500 MHz, $CDCl_3$) δ 1.14 (m, 4H), 1.31 (m, 4H), 1.76 (m, 2H), 2.18 (m, 2H), 3.00 (m, 1H), 4.24 (m, 2H), 7.01 (d, J=12.5 Hz, 1H), 9.70 (dd, J=4, 1 Hz, 1H), 11.66 (d, J=12.5 Hz, 1H).

E:Z—Ethyl-2-cyclohexyl-3-(3-hydroxypyridin-2ylamino)acrylate (1-4)

The aldehyde 1-2 (4.0 g, 20.2 mmol) was dissolved in EtOH (100 mL) to which was added 2-amino-3-hydroxypyridine 1-3 (2.0 g, 18.2 mmol) and the reaction was heated to reflux for 3 h. Solvent was removed in vacuo to provide a brown solid (5.4 g, quantitative yield). Crude NMR showed a mixture of E:Z isomers 1-4 and the material was carried forward with no purification.

3-Cyclohexyl-9-hydroxy-4H-pyrido[1,2-a]pyrimidin-4-one (1-5) (1621)

The keto-enol mixture 1-4 (5.4 g, 18.6 mmol) was dissolved in glacial AcOH (100 mL) and the resulting dark brown solution was heated to reflux for 3 h. Solvent was removed in vacuo to give a yellow/brown solid. The crude material was dissolved in hot EtOH (100 mL) and left to stand overnight. The resulting yellow solid that formed was collected by filtration and dried to afford 3-Cyclohexyl-9-hydroxy-4H-pyrido[1,2-a]pyrimidin-4-one 1-5 as yellow plates (2.8 g, 62%). $^1$H NMR 500 MHz, $CDCl_3$) δ 1.31 (m, 1H), 1.47 (m, 4H), 1.78 (m, 1H), 1.87 (m, 2H), 1.97 (m, 2H), 2.93 (m, 1H), 7.03 (t, J=7.5 Hz, 1H), 7.08 (dd, J=7.5, 1.5 Hz, 1H), 8.13 (s, 1H), 8.55 (dd, J=7.5, 1.5 Hz, 1H). HPLC: $t_R$=9.39 min (98.1%), MS m/z 245.09 [M+H]$^+$

TABLE 1

| Compound | Structure | MW | Proton NMR | MS |
|---|---|---|---|---|
| 1235 | 8-chloro-9-hydroxy-3-propyl-4H-pyrido[1,2-a]pyrimidin-4-one | | | m/z 238.68 [M + H]+ |
| 1607 | 7-chloro-9-hydroxy-3-propyl-4H-pyrido[1,2-a]pyrimidin-4-one | 238.67 | ¹H (500 MHz, CDCl₃) δ 1.00 (t, J = 7.5 Hz, 3H), 1.70 (sext, J = 7.5 Hz, 2H), 2.64 (t, J = 7.5 Hz, 2H), 6.5 (br s, 1H), 7.08 (d, J = 2.0 Hz, 1H), 8.11 (s, 1H), 8.58 (d, J = 2.0 Hz, 1H) | m/z 239.01 [M + H]+ |
| 1621 | 3-cyclohexyl-9-hydroxy-4H-pyrido[1,2-a]pyrimidin-4-one | 244.30 | ¹H NMR 500 MHz, CDCl₃) δ 1.31 (m, 1H), 1.47 (m, 4H), 1.78 (m, 1H), 1.87 (m, 2H), 1.97 (m, 2H), 2.93 (m, 1H), 7.03 (t, J = 7.5 Hz, 1H), 7.08 (dd, J = 7.5, 1.5 Hz, 1H), 8.13 (s, 1H), 8.55 (dd, J = 7.5, 1.5 Hz, 1H) | m/z 245.01 [M + H]+ |
| 1622 | 7-chloro-3-cyclohexyl-9-hydroxy-4H-pyrido[1,2-a]pyrimidin-4-one | 278.31 | ¹H NMR (500 MHz, CDCl₃) δ 1.29 (m, 1H), 1.46 (m, 4H), 1.79 (m, 1H), 1.87 (m, 2H), 1.96 (m, 2H), 2.93 (m, 1H), 5.97 (br s, 1H), 7.06 (d, J = 2.0 Hz, 1H), 8.10 (s, 1H), 8.58 (d, J = 2.0 Hz, 1H) | m/z 279.0 [M + H]+ |
| 1623 | 3-cyclopentyl-9-hydroxy-4H-pyrido[1,2-a]pyrimidin-4-one | 230.26 | ¹H NMR (500 MHz, d6-DMSO) δ 1.66 (m, 4H), 1.78 (m, 2H), 1.95 (m, 2H), 3.14 (m, 1H), 7.14 (m, 2H), 8.23 (s, 1H), 8.46 (dd, J = 7.0, 1.5 Hz, 1H). | m/z 231.1 [M + H]+ |
| 1624 | 7-chloro-3-cyclopentyl-9-hydroxy-4H-pyrido[1,2-a]pyrimidin-4-one | 264.71 | ¹H NMR (500 MHz, d6-DMSO) δ 1.66 (m, 4H), 1.77 (m, 2H), 1.98 (m, 2H), 3.13 (m, 1H), 7.15 (d, J = 2.0 Hz, 1H), 8.22 (s, 1H), 8.45 (d, J = 2.0 Hz, 1H) | m/z 265.0 [M + H]+ |
| 1643 | 7-chloro-9-hydroxy-3-isopropyl-4H-pyrido[1,2-a]pyrimidin-4-one | 238.7 | ¹H NMR (500 MHz, d6-DMSO) δ 049 (d, J = 7.0 Hz, 6H), 2.37 (sept, J = 7.0 Hz, 1H), 6.28 (d, J = 2.0 Hz, 1H), 7.40 (s, 1H), 7.71 (d, J = 2.0 Hz, 1H). | m/z 239.1 [M + H]+ |

TABLE 1-continued

Compounds prepared according to Example 1 (Scheme 1)

| Compound | Structure | MW | Proton NMR | MS |
|---|---|---|---|---|
| 1599 | (structure) | 283.1 | ¹H NMR (500 MHz, d₆-DMSO) δ 0.90 (t, J = 7.5 Hz, 3H), 1.59 (sext, J = 7.5 Hz, 2H), 2.53 (t, J = 7.5 Hz, 2H), 7.24 (d, J = 1.5 Hz, 1H), 8.23 (s, 1H), 8.51 (d, J = 1.5 Hz, 1H) | m/z 283.0 [M + H]+ |
| 1611 | (structure) | 364.6 | ¹H NMR (500 MHz, CDCl₃) δ 1.00 (t, J = 7.5 Hz, 3H), 1.70 (sext, J = 7.5 Hz, 2H), 2.62 (t, J = 7.5 Hz, 2H), 5.31 (s, 1H), 8.08 (s, 1H), 8.65 (s, 1H) | m/z 364.9 [M + H]+ |
| 1650 | (structure) | 282.3 | ¹H NMR (500 MHz, d₆-DMSO) δ 6.60 (s, 2H), 6.99 (d, J = 8 Hz, 1H), 7.23-7.28 (m, 2H), 7.33 (dd, J = 1.5, 8.5 Hz, 1H), 7.43 (d, J = 1.5 Hz, 1H), 8.53 (s, 1H), 8.61 (dd, J = 1.5, 7.0 Hz, 1H). | m/z 283.0 [M + H]+ |
| 1674 | (structure) | 252.3 | ¹H NMR (500 MHz, d₆-DMSO) δ 3.40 (s, 2H), 7.18 (m, 3H), 7.25 (m, 4H), 8.32 (s, 1H), 8.46 (s, 1H) | m/z 253.1 [M + H]+ |
| 1675 | (structure) | 286.7 | ¹H NMR (500 MHz, d₆-DMSO) δ 3.90 (s, 2H), 7.16 (m, 2H), 7.27 (m, 4H), 8.32 (s, 1H), 8.44 (s, 1H) | m/z 287.1 [M + H]+ |
| 1685 | (structure) | 220.2 | ¹H NMR (400 MHz, d6-DMSO) δ 2.94 (t, J = 5.2 Hz, 2H), 3.36 (s, 3H), 3.69 (t, J = 5.2 Hz, 2H), 7.06 (t, J = 6.0 Hz, 1H), 7.11 (d, J = 6.0 Hz, 1H), 8.21 (s, 1H), 8.56 (d, J = 7.0 Hz, 1H). | m/z 221.2 [M + H]+ |
| 1686 | (structure) | 254.7 | ¹H NMR (400 MHz, d6-DMSO) δ 2.92 (t, J = 4.8 Hz, 2H), 3.46 (s, 3H), 3.72 (t, J = 4.8 Hz, 2H), 7.09 (d, J = 2.0 Hz, 1H), 7.11 (d, J = 6.0 Hz, 1H), 8.18 (s, 1H), 8.57 (d, J = 2.0 Hz, 1H). | m/z 255.1 [M + H]+ |

Example 2

Substituted aryl and heteroaryl 9-hydroxy-4H-pyrido[1,2-a]pyrimidin-4-ones can be prepared by taking a 9-hydroxy-4H-pyrido[1,2-a]pyrimidin-4-one 1-5 in which $R^7$ is H synthesized in Example 1 shown in Scheme 1 above and iodinating at the ortho position to the phenol using iodine and hydrogen peroxide to afford 2-1 (Scheme 2). After protection of the phenol to provide 2-2, a Suzuki coupling reaction can be carried out with $Pd(PPh_3)_4$ as catalyst and commercially available boronic acids $R^7B(OH)_2$ or boronate esters $R^7B(OR^5)_2$ to afford aryl and heteroaryl compounds 2-3. Deprotection of the isopropoxy group in 2-3 by the action of HBr gives the target compounds 2-4 (Scheme 2).

Scheme 2

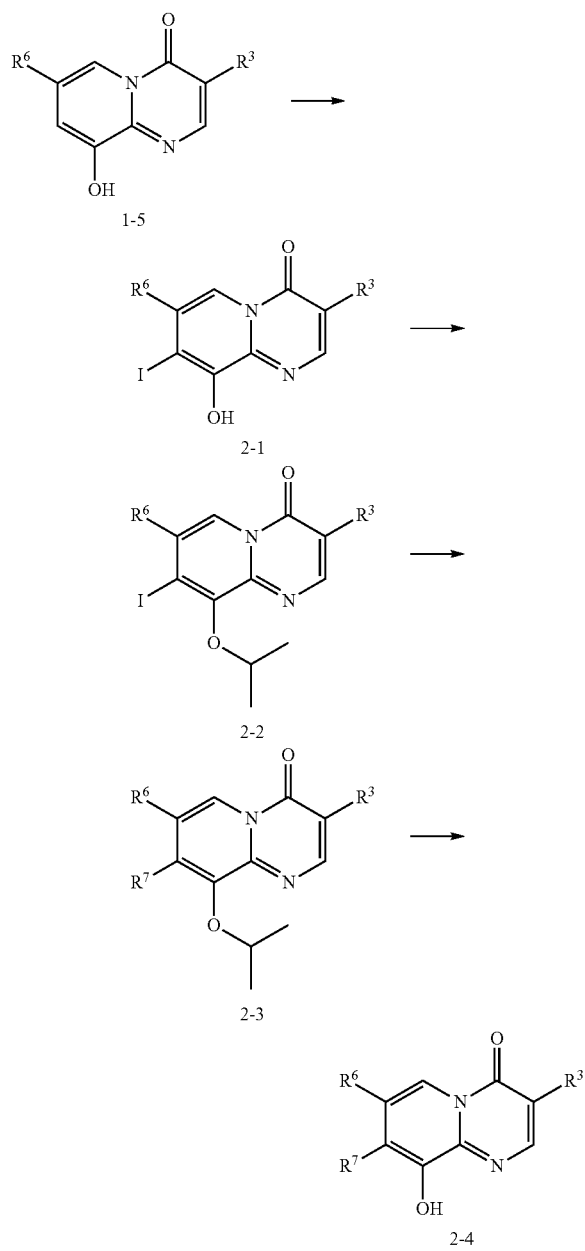

in which $R^3$ is $C_{1-4}$alkyl or $C(O)NHC_{1-4}$alkyl; $R^6$ is Cl; and $R^7$ is 5 or 6 membered optionally substituted heterocyclyl, optionally substituted phenyl or Compound 1629

7-Chloro-9-hydroxy-8-iodo-3-propyl-4H-pyrido[1,2-a]pyrimidin-4-one (2-1)

7-Chloro-9-hydroxy-3-propyl-4H-pyrido[1,2-a]pyrimidin-4-one 1-4 (500 mg, 2.1 mmol) was dissolved in EtOH (20 mL) and then treated with iodine (585 mg, 2.3 mmol) and 30% aq $H_2O_2$ (0.24 mL, 2.35 mmol) and the reaction was stirred for 48 h. The resulting precipitate was filtered, washed with EtOH and then dried giving the iodo compound 2-1 as a yellow powder (520 mg, 68%). $^1H$ NMR (500 MHz, $CDCl_3$) δ 1.00 (t, J=7.5 Hz, 3H), 1.70 (sext, J=7.5 Hz, 2H), 2.62 (t, J=7.5 Hz, 2H), 5.31 (s, 1H), 8.81 (s, 1H), 8.65 (s, 1H).

7-Chloro-8-iodo-9-isopropoxy-3-propyl-4H-pyrido[1,2-a]pyrimidin-4-one (2-2)

7-Chloro-9-hydroxy-8-iodo-3-propyl-4H-pyrido[1,2-a]pyrimidin-4-one (450 mg, 1.2 mmol) was dissolved in anhydrous DMF (10 mL) to which was then added $K_2CO_3$ (511 mg, 3.7 mmol) and 2-bromopropane (290 µL, 3.08 mmol) and the resulting dark mixture was stirred at 60° C. under argon o/n. The reaction was diluted with EtOAc (50 mL) and $H_2O$ (70 mL) and the EtOAc layer was separated. The aqueous layer was further extracted into EtOAc (×2) and the combined organic extracts were washed with brine, dried over $Na_2SO_4$, filtered and concentrated to afford the isopropyl ether 2-2 as a yellow solid (230 mg, 46%). $^1H$ NMR (500 MHz, $CDCl_3$) δ 0.99 (t, J=7.5 Hz, 3H), 1.44 (d, J=6.0 Hz, 6H), 1.69 (sext, J=7.5 Hz, 2H), 2.61 (t, J=7.5 Hz, 2H), 5.51 (sept, J=6.0 Hz, 1H), 8.15 (s, 1H), 8.92 (s, 1H).

7-Chloro-8-(pyridine-3-yl)-9-isopropoxy-3-propyl-4H-pyrido[1,2-a]pyrimidin-4-one (2-3)

7-Chloro-8-iodo-9-isopropoxy-3-propyl-4H-pyrido[1,2-a]pyrimidin-4-one 2-2 (100 mg, 0.25 mmol) 3-pyridyl boronic acid (37 mg, 0.30 mmol) were dissolved in DMF (5 mL) followed by the addition of 2M $K_2CO_3$ (0.5 mL, 1 mmol)). The solution was degassed via argon sparge/sonication then $Pd(PPh_3)_4$ (15 mg, 0.013 mmol) was added and the reaction was heated to 100° C. for 18 h. The reaction was diluted with EtOAc and filtered through celite rinsing with EtOAc. The solvent was removed in vacuo and the residue was purified by flash chromatography eluting with 40% EtOAc/petroleum ether 40-60° C., giving a gummy solid. A second column eluting with 10%-20% ether/$CH_2Cl_2$ afforded the desired pyridine 2-3 as a white solid (53 mg, 60%). $^1H$ NMR (500 MHz, $CDCl_3$) δ 1.01 (t, J=7.5 Hz, 3H), 1.05 (d, J=6.0 Hz, 6H), 1.72 (sext, J=7.5 Hz, 2H), 2.66 (t, J=7.5 Hz, 2H), 4.93 (sept, J=6.0 Hz, 1H), 7.45 (ddd, J=8, 5, 0.5 Hz, 1H), 7.77 (dt, J=8.0, 2.0 Hz, 1H), 8.23 (s, 1H), 8.68 (d, J=1.5 Hz, 1H), 8.71 (dd, J=5.0, 1.5 Hz, 1H), 9.02 (s, 1H).

7-Chloro-9-hydroxy-3-propyl-8-(pyridin-3-yl)-4H-pyrido[1,2-a]pyrimidine-4-one (2-4) (1629)

7-Chloro-8-(pyridine-3-yl)-9-isopropoxy-3-propyl-4H-pyrido[1,2-a]pyrimidin-4-one 2-3 (50 mg, 0.14 mmol) was added to 48% aq HBr (3 mL) and heated to 120° C. for 1.5 h. Upon cooling the resulting yellowish solution was neutralized with sat. aq. NaHCO₃. The aqueous layer was extracted into CH₂Cl₂ (×3) and the organic layer was dried over Na₂SO₄, filtered and concentrated to a afford 7-Chloro-9-hydroxy-propyl-8-(pyridin-3-yl)-4H-pyrido[1,2-a]pyrimidine-4-one (2-4) as a light green powder (38 mg, 86%). ¹H NMR (500 MHz, CDCl₃) δ 1.02 (t, J=7.5 Hz, 3H), 1.72 (sext, J=7.5 Hz, 2H), 2.67 (t, J=7.5 Hz, 2H), 7.47 (dd, J=7.5, 5.0 Hz, 1H), 7.84 (d, J=7.5 Hz, 1H), 8.14 (s, 1H), 8.71 (d, J=5.0 Hz, 1H), 8.74 (s, 1H), 8.75 (br s, 1H). HPLC: t$_R$=7.99 min (91.7%). MS: m/z 316.1 [M+H]+

TABLE 2

| Compounds prepared according to Example 2 (Scheme 2) | | | | |
|---|---|---|---|---|
| Compound | Structure | MW | NMR | MS |
| 1596 | | 281.31 | ¹H NMR (500 MHz, d6-DMSO δ 1.27 (d, J = 7.0 Hz, 6H), 3.14 (m, 1H), 7.48 (d, J = 7.0 Hz, 1H), 7.54 (m, 1H), 8.20 (d, J = 8.0 Hz, 1H), 8.25 (s, 1H), 8.50 (d, J = 8.0 Hz, 1H), 8.60 (d, J = 4 Hz, 1H), 9.00 (s, 1H) | m/z 282.1 [M + H]⁺ |
| 1597 | | 326.39 | ¹H NMR (500 MHz, d6-DMSO) δ 0.88 (d, J = 6.5 Hz, 6H), 1.28 (d, J = 7.0 Hz, 6H), 2.17 (m, 1H), 3.14 (m, 1H), 4.02 (d, J = 7.5 Hz, 2H), 7.63 (d, J = 7.5 Hz, 1H), 8.21 (d, J = 7.5 Hz, 1H)m, 8.44 (s, 1H), 8.46 (d, J = 7.5 Hz, 1H). | m/z 327.1 [M + H]⁺ |
| 1600 | | 299.32 | ¹H NMR (500 MHz, d6-DMSO) δ 1.27 (d, J = 7.0 Hz, 6H), 2.19 (s, 3H), 2.35 (s, 3H), 3.14 (m, 1H), 7.22 (d, J = 7.5 Hz, 1H), 0, 8.24 (s, 1H), 8.48 (d, J = 7.5 Hz, 1H). | m/z 300.1 [M + H]⁺ |
| 1601 | | 312.37 | ¹H NMR (500 MHz, d6-DMSO) δ 0.85 (d, J = 7.0 Hz, 3H), 1.26 (d, J = 7.0 Hz, 6H), 3.11 (sept, J = 7.0 Hz, 1H), 4.15 (t, J = 7.0 Hz, 2H), 7.61 (d, J = 7.5 Hz, 1H), 8.18 (s, 1H), 8.20 (s, 1H), 8.43 (s, 1H), 8.45 (d, J = 7.5 Hz, 1H). | m/z 313.1 [M + H]⁺ |
| 1602 | | 284.31 | ¹H NMR (500 MHz, CDCl₃) δ 1.34 (d, J = 7.0 Hz, 6H), 3.30 (sept, J = 7.0 Hz, 1H), 3.93 (s, 3H), 6.49 (s, 1H), 7.03 (d, J = 7.5 Hz, 1H), 7.61 (s, 1H), 8.17 (s, 1H), 8.58 (d, J = 7.5 H, 1H). | m/z 285.1 [M + H]⁺ |
| 1603 | | 299.32 | ¹H NMR (500 MHz, d6-DMSO) δ 0.91 (t, J = 7.5 Hz, 6H), 1.81 (m, 2H), 2.19 (s, 3H), 2.35 (s, 3H), 7.29 (d, J = 7.5 Hz, 1H), 0, 8.26 (s, 1H), 8.51 (d, J = 7.5 Hz, 1H) | m/z 300.2 [M + H]⁺ |

TABLE 2-continued

Compounds prepared according to Example 2 (Scheme 2)

| Compound | Structure | MW | NMR | MS |
|---|---|---|---|---|
| 1629 | 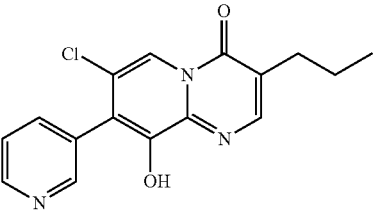 [SMILES: CCCc1cnc2c(O)c(-c3cccnc3)c(Cl)cn2c1=O] | 315.75 | ¹H NMR (500 MHz, CDCl₃) δ 1.02 (t, J = 7.5 Hz, 3H), 1.72 (sext, J = 7.5 Hz, 2H), 2.67 (t, J = 7.5 Hz, 2H), 7.47 (dd, J = 7.5, 5.0 Hz, 1H), 7.84 (d, J = 7.5 Hz, 1H), 8.14 (s, 1H), 8.71 (d, J = 5.0 Hz, 1H), 8.74 (s, 1H), 8.75 (br s, 1H) | m/z 316.1 [M + H]⁺ |
| 1630 | 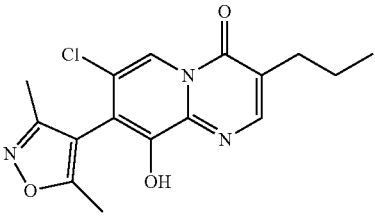 [SMILES: CCCc1cnc2c(O)c(-c3c(C)noc3C)c(Cl)cn2c1=O] | 333.7 | ¹H NMR (500 MHz, CDCl₃) δ 1.02 (t, J = 7.5 Hz, 3H), 1.72 (sext, J = 7.5 Hz, 2H), 2.23 (s, 3H), 2.36 (s, 3H), 2.66 (t, J = 7.5 Hz, 2H), 8.13 (s, 1H), 8.72 (s, 1H) | m/z 334.1 [M + H]⁺ |
| 1633 | 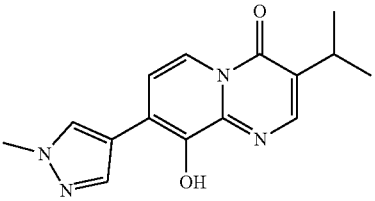 [SMILES: CC(C)c1cnc2c(O)c(-c3cnn(C)c3)ccn2c1=O] | 284.3 | ¹H NMR (500 MHz, d6-DMSO) δ 1.26 (d, J = 7.0 Hz, 6H), 3.11 (m, 1H), 3.93 (s, 3H), 7.61 (d, J = 8.0 Hz, 1H), 8.16 (s, 1H), 8.19 (s, 1H), 8.41 (s, 1H), 8.45 (d, J = 8.0 Hz, 1H)' | m/z 285.1 [M + H]⁺ |
| 1639 | 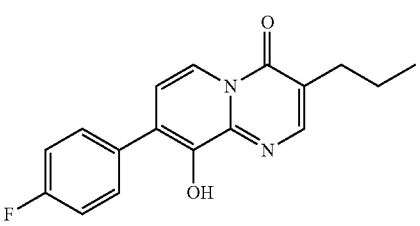 [SMILES: CCCc1cnc2c(O)c(-c3ccc(F)cc3)ccn2c1=O] | 298.3 | ¹H NMR (500 MHz, d6-DMSO) δ 0.92 (t, J = 7.5 Hz, 3H), 1.61 (q, J = 7.5 Hz, 2H), 2.55 (t, J = 7.5 Hz, 2H), 7.34 (app t, J = 8.5 Hz, 2H), 7.41 (d, J = 7.5 Hz, 1H), 7.86 (m, 2H), 8.26 (s, 1H), 8.48 (d, J = 7.5 Hz, 1H) | m/z 299.1 [M + H]⁺ |
| 1641 | 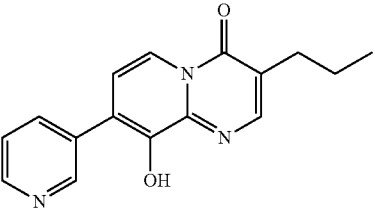 [SMILES: CCCc1cnc2c(O)c(-c3cccnc3)ccn2c1=O] | 281.3 | ¹H NMR (500 MHz, CDCl₃) δ 0.92 (t, J = 7.0 Hz, 3H), 1.62 (q, J = 7.0 Hz, 2H), 2.57 (t, J = 7.0 Hz, 2H), 7.66 (d, J = 7.5 Hz, 1H), 8.07 (m, 1H), 8.24 (s, 1H), 8.37 (d, J = 7.5 Hz, 1H), 8.85 (d, J = 5.5 Hz, 1H), 8.91 (d, J = 8.0 Hz, 1H), 9.51 (s, 1H). | m/z 282.1 [M + H]⁺ |
| 1648 | 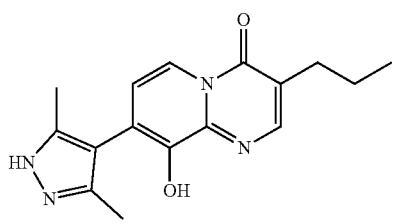 [SMILES: CCCc1cnc2c(O)c(-c3c(C)n[nH]c3C)ccn2c1=O] | 298.3 | ¹H NMR (500 MHz, d6-DMSO) δ 0.91 (t, J = 7.5 Hz, 3H), 1.60 (sext, J = 7.5 Hz, 2H), 2.13 (s, 6H), 2.54 (t, J = 7.5 Hz, 2H), 7.15 (d, J = 7.0 Hz, 1H), 8.23 (s, 1H), 8.44 (d, J = 7.0 Hz, 1H). | m/z 299.2 [M + H]⁺ |
| 1651 | 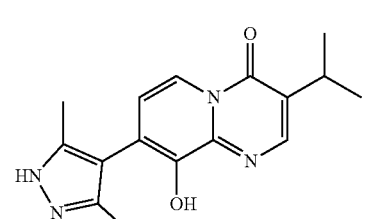 | 298.3 | ¹H NMR (500 MHz, d6-DMSO) δ 1.26 (d, J = 6.5 Hz, 6H), 2.14 (s, 6H), 3.13 (sept, J = 6.5 Hz, 1H), 7.16 (d, J = 7.5 Hz, 1H), 8.22 (s, 1H), 8.47 (d, J = 7.5 Hz, 1H). | m/z 299.1 [M + H]⁺ |

TABLE 2-continued

Compounds prepared according to Example 2 (Scheme 2)

| Compound | Structure | MW | NMR | MS |
|---|---|---|---|---|
| 1652 | 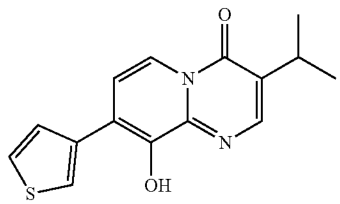 [SMILES: CC(C)c1cnc2c(O)c(-c3ccsc3)ccn2c1=O] | 286.4 | ¹H NMR (500 MHz, d6-DMSO) δ 1.33 (d, J = 7.0 Hz, 6H), 3.26 (sept, J = 7.0 Hz, 1H), 7.35 (d, J = 7.5 Hz, 1H), 7.46 (dd, J = 4.0, 2.0 Hz, 1H), 7.19 (d, J = 4.0 Hz, 1H), 8.12 (s, 1H), 8.16 (s, 1H), 8.56 (d, J = 7.5 Hz, 1H). | m/z 287.0 [M + H]⁺ |
| 1653 | 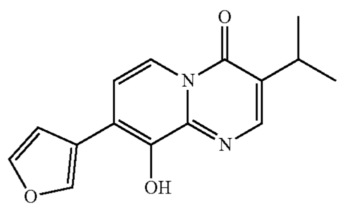 [SMILES: CC(C)c1cnc2c(O)c(-c3ccoc3)ccn2c1=O] | 270.3 | ¹H NMR (500 MHz, d6-DMSO) δ 1.32 (d, J = 7.0 Hz, 6H), 3.26 (sept, J = 7.0 Hz, 1H), 6.93 (d, J = 2.0 Hz, 1H), 7.22 (d, J = 7.5 Hz, 1H), 7.57 (t, J = 2.0 Hz, 1H), 8.15 (s, 1H), 8.30 (s, 1H), 8.56 (d, J = 7.5 Hz, 1H). | m/z 271.1 [M + H]⁺ |
| 1654 | 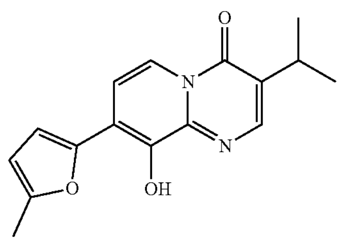 [SMILES: Cc1ccc(-c2ccn3c(=O)c(C(C)C)cnc3c2O)o1] | 284.3 | ¹H NMR (400 MHz, CDCl₃) δ 1.32 (d, J = 7.2 Hz, 6H), 3.26 (sept, J = 7.2 Hz, 1H), 6.23 (d, J = 3.2 Hz, 1H), 7.23 (d, J = 3.2 Hz, 1H), 7.57 (d, J = 8.0 Hz, 1H), 8.13 (s, 1H), 8.54 (d, J = 8.0 Hz, 1H). | m/z 285.1 [M + H]⁺ |
| 1655 | 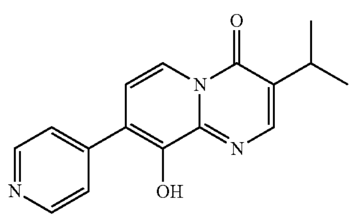 [SMILES: CC(C)c1cnc2c(O)c(-c3ccncc3)ccn2c1=O] | 281.3 | ¹H NMR (500 MHz, d6-DMSO) δ 1.27 (d, J = 6.5 Hz, 6H), 3.12 (sept, J = 6.5 Hz, 1H), 7.61 (d, J = 7.0 Hz, 1H), 8.16 (s, 1H), 8.17 (br m, 2H), 8.31 (d, J = 7.0 Hz, 1H), 8.73 (d, J = 6.0 Hz, 1H) | m/z 282.1 [M + H]⁺ |
| 1659 | 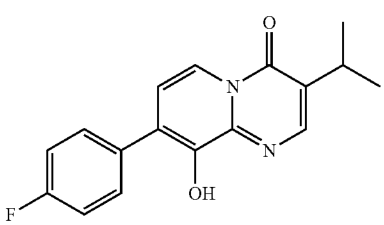 [SMILES: CC(C)c1cnc2c(O)c(-c3ccc(F)cc3)ccn2c1=O] | 298.3 | ¹H NMR (400 MHz, d6-DMSO) δ 0.91 (t, J = 7.2 Hz, 3H), 1.36 (sext, J = 7.2 Hz, 2H), 1.51 (quin, J = 7.6 Hz, 2H), 3.35 (m, 2H), 7.45 (d, J = 7.2 Hz, 1H), 8.60 (d, J = 7.2 Hz, 1H), 8.96 (s, 1H), 9.01 (m, 1H). | m/z 299.2 [M + H]⁺, 282.3 [M − 17]⁺ |
| 1660 | 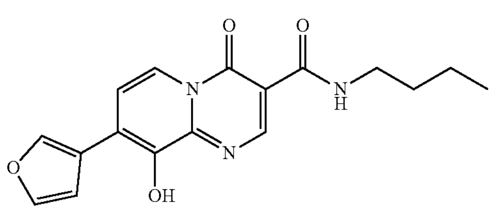 | 355.4 | ¹H NMR (400 MHz, d6-DMSO) δ 0.91 (t, J = 7.6 Hz, 3H), 1.36 (m, 2H), 1.51 (m, 2H), 3.36 (m, 2H), 7.36 (m, 2H), 7.66 (d, J = 7.2 Hz, 1H), 7.90 (m, 2H), 8.70 (d, J = 7.2 Hz, 1H), 8.99 (m, 1H), 9.02 (s, 1H). | m/z 356.1 [M + H]⁺ |
| 1668 | 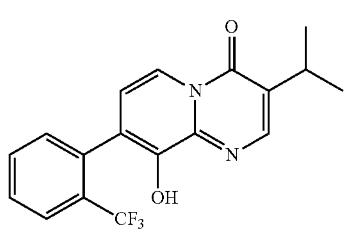 [SMILES: CC(C)c1cnc2c(O)c(-c3ccccc3C(F)(F)F)ccn2c1=O] | 348.3 | ¹H NMR (400 MHz, d6-DMSO) δ 1.28 (d, J = 7.0 Hz, 6H), 3.16 (sept, J = 7.0 Hz, 1H), 7.11 (d, J = 7.5 Hz, 1H), 7.46 (d, J = 7.5 Hz, 1H), 7.67 (t, J = 7.5 Hz, 1H), 7.75 (t, J = 7.5 Hz, 1H), 7.87 (d, J = 7.5 Hz, 1H), 8.26 (s, 1H), 8.50 (d, J = 7.5 Hz, 1H) | m/z 349.1 [M + H]⁺ |

TABLE 2-continued

Compounds prepared according to Example 2 (Scheme 2)

| Compound | Structure | MW | NMR | MS |
|---|---|---|---|---|
| 1671 | 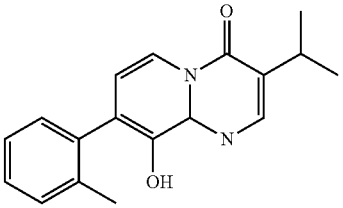 [SMILES: Cc1ccccc1C1=C(O)C2NC=C(C(C)C)C(=O)N2C=C1] | 296.4 | ¹H NMR (500 MHz, d6-DMSO) δ 1.28 (d, J = 7.0 Hz, 6H), 2.17 (s, 3H), 3.15 (sept, J = 7.0 Hz, 1H), 7.13 (d, J = 7.5 Hz, 1H), 7.24 (d, J = 7.0 Hz, 1H), 7.28 (m, 1H), 7.32 (m, 2H), 8.25 (s, 1H), 8.50 (d, J = 7.5 Hz, 1H). | |
| 1680 | 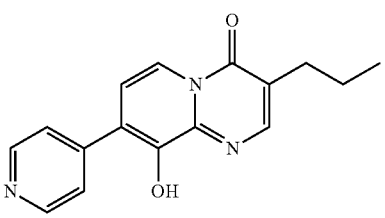 [SMILES: CCCc1cnc2c(O)c(-c3ccncc3)ccn2c1=O] | 281.3 | ¹H NMR (400 MHz, d6-DMSO) δ 0.92 (t, J = 7.2 Hz, 3H), 1.62 (m, 2H), 2.56 (m, 2H), 7.53 (d, J = 7.6 Hz, 1H), 7.98 (d, J = 6.0 Hz, 2H), 8.23 (s, 1H), 8.40 (d, J = 7.6 Hz, 1H), 8.71 (d, J = 6.0 Hz, 2H). | m/z 282.1 [M + H]⁺ |
| 1681 | 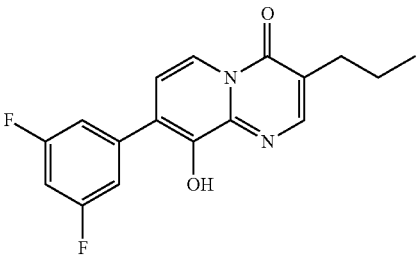 [SMILES: CCCc1cnc2c(O)c(-c3cc(F)cc(F)c3)ccn2c1=O] | 316.3 | ¹H NMR (400 MHz, d6-DMSO) δ 0.92 (t, J = 7.2 Hz, 3H), 1.62 (m, 2H), 2.56 (m, 2H), 7.31 (m, 1H), 7.49 (d, J = 7.6 Hz, 1H), 7.61 (m, 2H), 8.26 (s, 1H), 8.42 (d, J = 7.6 Hz, 1H) | m/z 317.1 [M + H]⁺ |
| 1683 | 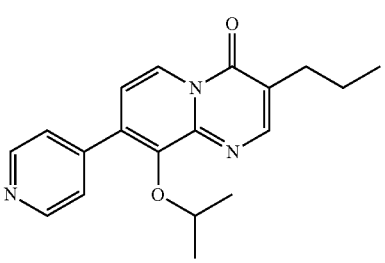 [SMILES: CCCc1cnc2c(OC(C)C)c(-c3ccncc3)ccn2c1=O] | 323.4 | ¹H NMR (400 MHz, CDCl₃) δ 0.937 (t, J = 7.2 Hz, 3H), 1.04 (s, 3H), 1.04 (d, J = 3.2 Hz, 6H), 1.66 (m, 2H), 2.59 (t, J = 7.2 Hz, 2H), 4.82 (s, 1H), 7.04 (d, J = 7.2 Hz, 1H), 7.55 (dd, J = 4.4, 1.6 Hz, 2H), 8.19 (s, 1H), 8.69 (dd, J = 4.4, 1.6 Hz, 2H), 8.82 (d, J = 7.2 Hz, 1H). | m/z 324.2 [M + H]⁺ |
| 1684 | 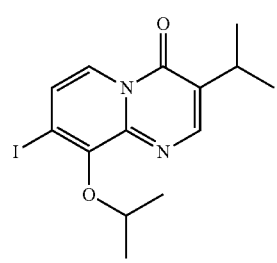 [SMILES: CC(C)Oc1c(I)ccn2c(=O)c(C(C)C)cnc12] | 372.2 | ¹H NMR (500 MHz, d6-DMSO) δ 1.24 (d, J = 4.0 Hz, 6H), 1.32 (s, 6H), 3.07 (m, 1H), 5.31 (m, 1H), 7.57 (d, J = 7.5 Hz, 1H), 8.23 (s, 1H), 8.42 (d, J = 7.5 Hz, 1H) | m/z 373.1 [M + H]⁺ |

Example 3

Substituted methylamino compounds can be prepared from 9-hydroxy-4H-pyrido[1,2-a]pyrimidin-4-ones synthesized in Scheme 1 above, adapting a procedure from *Chemistry of Heterocyclic Compounds*, 1992, 28, 1425-1431. Reaction of commercially available aminals with 9-hydroxy-4H-pyrido[1,2-a]pyrimidin-4-ones 1-5 provided the desired compounds 3-1 (Scheme 3).

Scheme 3

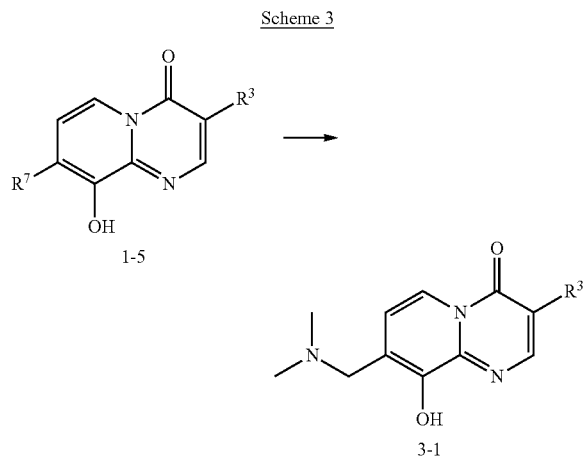

in which $R^3$ is $C_{5-6}$cycloalkyl, $C_{1-4}$alkyl optionally interrupted with O or benzyl; $R^7$ is $CH_2NR^{10}R^{10}$ in which $R^9$ and $R^{10}$ are $C_{1-2}$alkyl or together with the N to which they are attached from morpholinyl.

Compound 1627

3-Cyclopentyl-8-(dimethylamino)methyl-9-hydroxy-4H-pyrido[1,2-a]pyrimidin-4-one (3-1)

A solution of cyclopentyl-9-hydroxy-4H-pyrido[1,2-a]pyrimidin-4-one (137 mg, 0.60 mmol) 1-5 in anhydrous toluene (4 mL) was treated with N,N,N,N-tetramethylmethylenediamine (240 ML, 1.76 mmol) for 4 h. The reaction was cooled, concentrated and the resulting solid was crystallized from hot acetonitrile to afford the desired amine 3-1 as a pale green solid (50 mg, 29%). $^1$H NMR (500 MHz, d6-DMSO) δ 1.71 (m, 4H), 1.84 (m, 2H), 1.66 (m, 2H), 2.07 (m, 2H), 2.41 (s, 6H), 3.23 (m, 1H), 3.72 (s, 2H), 6.84 (d, J=7.5 Hz, 1H), 8.26 (s, 1H), 8.57 (d, J=7.5 Hz, 1H). HPLC: tR=7.64 min (92.6%). MS: m/z 288.1 [M+H]$^+$.

TABLE 3

Compounds prepared according to Example 3 (Scheme 3)

| Compound | Structure | MW | NMR | MS |
|---|---|---|---|---|
| 1627 | 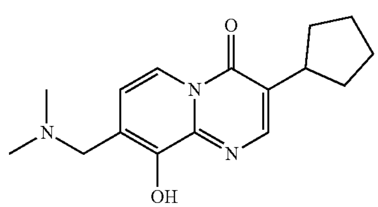 [SMILES: CN(C)Cc1ccn2c(=O)c(C3CCCC3)cnc2c1O] | 287.4 | $^1$H NMR (500 MHz, d6-DMSO) δ 1.71 (m, 4H), 1.84 (m, 2H), 1.66 (m, 2H), 2.07 (m, 2H), 2.41 (s, 6H), 3.23 (m, 1H), 3.72 (s, 2H), 6.84 (d, J = 7.5 Hz, 1H), 8.26 (s, 1H), 8.57 (d, J = 7.5 Hz, 1H) | m/z 288.1 [M + H]$^+$ |
| 1631 | 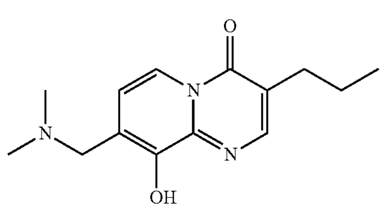 [SMILES: CCCc1cnc2c(O)c(CN(C)C)ccn2c1=O] | 261.3 | $^1$H NMR (500 MHz, CDCl$_3$) δ 0.99 (t, J = 7.5 Hz, 3H), 1.70 (sext, J = 7.5 Hz, 2H), 2.41 (s, 6H), 2.64 (t, J = 7.5 Hz, 2H), 3.73 (s, 2H), 6.85 (d, J = 7.5 Hz, 1H), 8.21 (s, 1H), 8.57 (d, J = 7.5 Hz, 1H); | m/z 262.2 [M + H]$^+$ |
| 1632 | 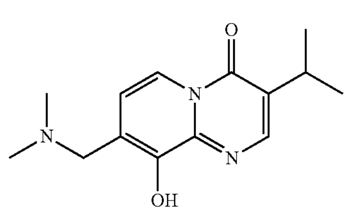 [SMILES: CC(C)c1cnc2c(O)c(CN(C)C)ccn2c1=O] | 261.3 | $^1$H NMR (500 MHz, d6-DMSO) δ 1.32 (d, J = 7.0 Hz, 6H), 3.27 (m, 1H), 3.73 (s, 2H), 6.85 (d, J = 7.5 Hz, 1H), 8.24 (s, 1H), 8.57 (d, J = 7.5 Hz, 1H). | m/z 262.2 [M + H]$^+$ |

TABLE 3-continued

Compounds prepared according to Example 3 (Scheme 3)

| Compound | Structure | MW | NMR | MS |
|---|---|---|---|---|
| 1640 | 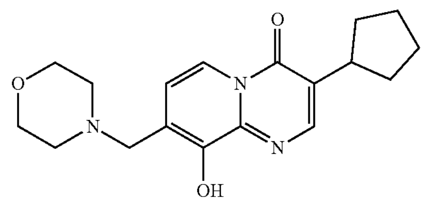 [SMILES: O=c1c(C2CCCC2)cnc2c(O)c(CN3CCOCC3)ccn12] | 329.3 | ¹H NMR (500 MHz, CDCl3) δ 1.71 (m, 4H), 1.84 (m, 2H), 2.08 (m, 2H), 2.62 (m, 4H), 3.26 (quintet, 1H), 3.78 (m, 6H), 6.94 (d, J = 7.5 Hz, 1H), 8.22 (s, 1H), 8.56 (d, J = 7.5 Hz, 1H). | m/z 330.2 [M + H]⁺ |
| 1642 | 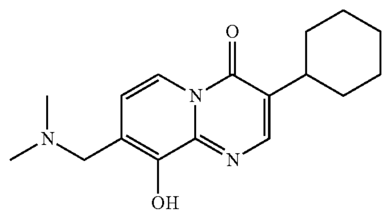 [SMILES: CN(C)Cc1ccn2c(=O)c(C3CCCCC3)cnc2c1O] | 301.4 | ¹H NMR (500 MHz, CDCl₃) δ 1.27 (m, 1H), 1.48 (m, 4H), 1.77 (m, 1H), 1.85 (m, 2H), 1.95 (m, 2H), 2.40 (s, 6H), 2.92 (m, 1H), 3.72 (s, 2H), 6.83 (d, J = 7.5 Hz, 1H), 8.21 (s, 1H), 8.56 (d, J = 7.5 Hz, 1H). | m/z 302.2 [M + H]⁺ |
| 1645 | 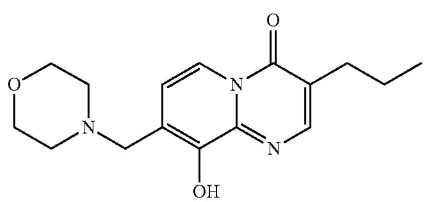 [SMILES: CCCc1cnc2c(O)c(CN3CCOCC3)ccn2c1=O] | 303.4 | ¹H NMR (500 MHz, CDCl₃) δ 0.98 (t, J7.5 Hz, 3H), 1.69 (sext, J = 7.5 Hz, 2H), 2.62 (m, 6H), 3.77 (s, 6H), 6.94 (d, J = 7.0 Hz, 1H), 8.18 (s, 1H), 8.56 (d, J = 7.0 Hz, 1H). | m/z 304.2 [M + H]⁺ |
| 1647 | 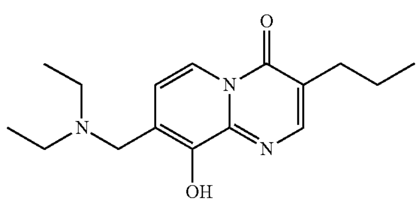 [SMILES: CCCc1cnc2c(O)c(CN(CC)CC)ccn2c1=O] | 289.4 | ¹H NMR (400 MHz, CDCl₃) δ 0.98 (t, J = 7.2 Hz, 3H), 1.18 (t, J = 7.2 Hz, 6H), 1.69 (sext, J = 7.2 Hz, 2H), 2.63 (t, J = 7.2 Hz, 2H), 2.71 (q, J = 7.2 Hz, 4H), 3.87 (s, 2H), 6.76 (d, J = 7.2 Hz, 1H), 8.22 (s, 1H), 8.55 (d, J = 7.2 Hz, 1H). | m/z 290.2 [M + H]⁺ |
| 1656 | 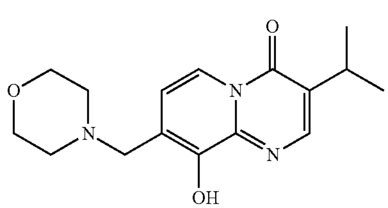 [SMILES: CC(C)c1cnc2c(O)c(CN3CCOCC3)ccn2c1=O] | 303.4 | ¹H NMR (500 MHz, d6-DMSO) δ 1.31 (d, J = 7 Hz, 6H), 2.61 (m, 4H), 3.27 (sept, J = 7 Hz, 1H), 3.76 (m, 6H), 6.95 (d, J = 7.5 Hz, 1H), 8.20 (s, 1H), 8.56 (d, J = 7.5 Hz, 1H) | m/z 304.2 [M + H]⁺ |
| 1679 | 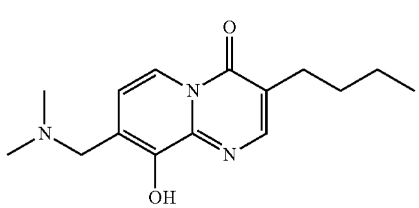 [SMILES: CCCCc1cnc2c(O)c(CN(C)C)ccn2c1=O] | 275.4 | ¹H NMR (400 MHz, CDCl₃) δ 0.94 (t, J = 7.2 Hz, 3H), 1.39 (sext, J = 7.2 Hz, 2H), 1.62 (quin, J = 7.2 Hz, 2H), 2.41 (s, 6H), 2.85 (t, J = 7.2 Hz, 1H), 3.73 (s, 2H), 6.83 (d, J = 7.2 Hz, 1H), 8.22 (s, 1H), 8.56 (d, | m/z 276.2 [M + H]⁺ |

TABLE 3-continued

Compounds prepared according to Example 3 (Scheme 3)

| Compound | Structure | MW | NMR | MS |
|---|---|---|---|---|
|  |  |  | J = 7.2 Hz, 1H), |  |
| 1691 | 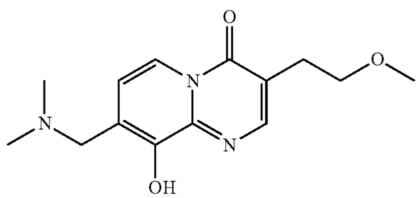 | 277.3 | $^1$H NMR (400 MHz, d6-DMSO) δ 2.76 (s, 6H), 2.82 (t, J = 6.5 Hz, 2H), 3.24 (s, 3H), 3.56 (t, J = 6.5 Hz, 2H), 4.39 (s, 2H), 7.47 (d, J = 7.0 Hz, 1H), 8.28 (s, 1H), 8.48 (d, J = 7.0 Hz, 1H). | m/z 278.2 [M + H]$^+$ |
| 1693 | 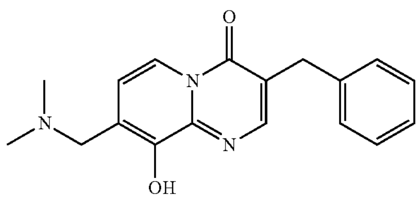 [SMILES: CN(C)Cc1ccn2c(=O)c(Cc3ccccc3)cnc2c1O] | 309.4 | $^1$H NMR (500 MHz, d6-DMSO) δ 2.22 (s, 6H), 3.58 (s, 2H), 3.88 (s, 2H), 7.22 (m, 6H), 8.30 (s, 1H), 8.42 (s, J = 5.0 Hz, 1H) | m/z 310.2 [M + H]$^+$ |
| 1706 | 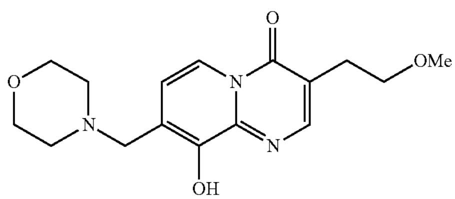 [SMILES: COCCc1cnc2c(O)c(CN3CCOCC3)ccn2c1=O] | 319.4 | $^1$H NMR (400 MHz, d6-DMSO) δ 2.62 (s, 4H), 2.92 (t, J = 6.8 Hz, 2H), 3.65 (s, 3H), 3.67 (t, J = 6.8 Hz, 2H), 3.68 (m, 4H), 3.78 (s, 2H), 6.97 (d, J = 7.6 Hz, 1H), 8.25 (s, 1H), 8.56 (d, J = 7.6 Hz, 1H). | m/z 320.2 [M + H]$^+$ |

Example 4

Substituted triazole compounds can be prepared from compounds 1-5 in Scheme 1. Protection of 1-4 to give 4-1 followed by Sonagashira coupling provides trimethylsilyacetylene compounds 4-2. Removal of the silane group under basic conditions affords the acetylenes 4-3. Compound 4-3 is allowed to react with a known azide in the presence of a Cu(II) catalyst. Subsequent 1,3-dipolar cycloaddition (Click chemistry) proceeds smoothly to generate substituted triazoles 4-4. Finally, deprotection of 4-4 affords the target compounds 4-5 (Scheme 4). Note: azides are prepared according to a literature procedure described in Synthesis 1997, 4, 413-414 (scheme 4).

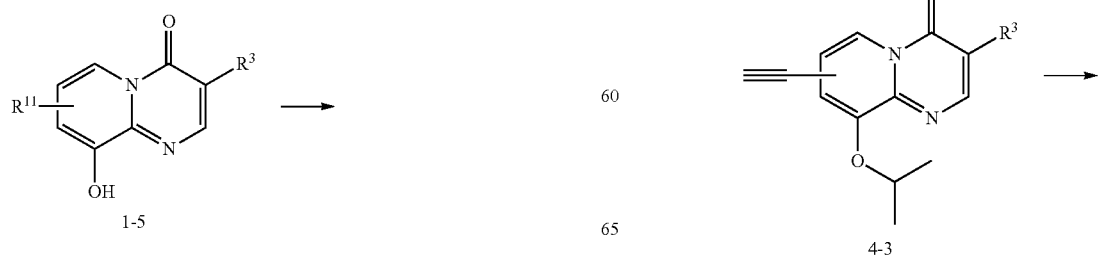

Scheme 4

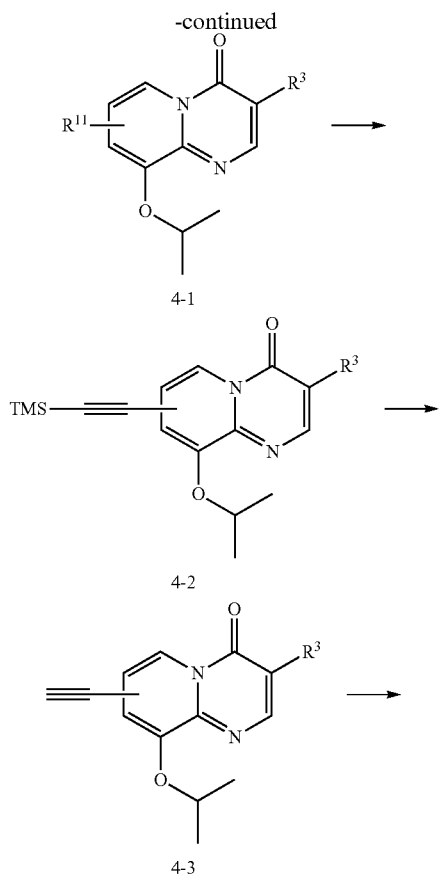

-continued

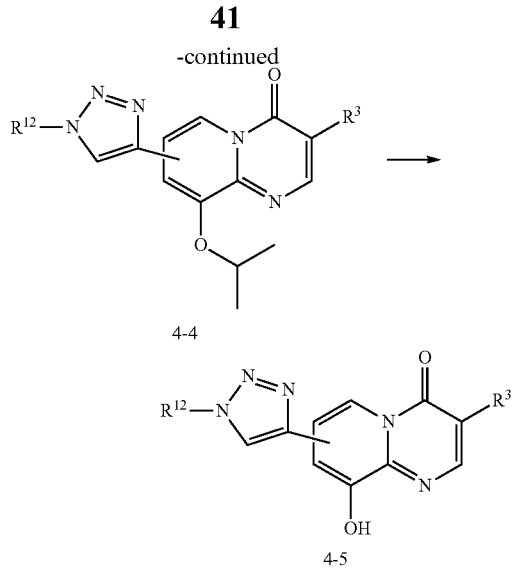

4-4

4-5 in which R³ is C₁₋₄alkyl;
R¹¹ is Br; and
R¹² is benzyl or cyclopentyl.

Compound 1616

7-Bromo-9-isopropoxy-3-propyl-4H-pyrido[1,2-a]pyrimidin-4-one (4-1)

7-Bromo-9-hydroxy-3-propyl-4H-pyridon[1,2-a]pyrimidin-4-one 1-5 (2.0 g, 7.1 mmol) was dissolved in anhydrous DMF (30 mL) then treated with $K_2CO_3$ (2.93 g, 2.1 mmol) followed by 2-brompropane (1.65 mL, 17.7 mmol) and the reaction was stirred at 60° C. o/n. Volatiles were removed in vacuo and the residue was taken up in $H_2O$ (50 mL) and EtOAc (50 mL). The EtOAc layer was separated and the aqueous layer was further extracted into EtOAc (2×50 mL). The combined organic layers were washed with brine, dried over $Na_2SO_4$, filtered, concentrated and purified by flash chromatography eluting with 10% EtOAc/petroleum spirits 40-60° C. to afford the isopropyl ether 4-1 as a brown oil (1.50 g, 65%). ¹H NMR (500 MHz, $CDCl_3$) δ0.98 (t, J=7.5 Hz, 3H), 1.53 (d, J=6.0 Hz, 6H), 1.68 (sext, J=7.5 Hz, 2H), 2.63 (t, J=7.5 Hz, 2H), 4.73 (sept, J=6.0 Hz, 1H), 6.96 (d, J=1.5 Hz, 1H), 8.24 (s, 1H), 8.80 (d, J=1.5 Hz, 1H).

9-Isopropoxy-3-propyl-7-((trimethylsoliyl)ethynyl)-4H-pyrido[1,2-a]pyrimidin-4-one (4-2)

7-Bromo-9-isopropoxy-3-propyl-4H-pyrido[1,2-a]pyrimidin-4-one 4-1 (1.45 g, 4.5 mmol) was dissolved in anhydrous THF (60 mL) and diisopropylamine (5 mL, 35.7 mmol). The solution was degassed via argon sparge and sonication then the following reagents were introduced into the reaction vessel. $PdCl_2(PPh_3)_2$ (188 mg, 0.27 mmol), CuI (17 mg, 0.09 mmol) and TMS acetylene (1 mL, 7.08 mmol) then the reaction was heated to 70° C. for 2 h. The reaction was filtered through a small pad of silica gel washing with EtOAc. The filtrate was concentrated and the residue was purified by flash chromatography eluting with petroleum spirits 40-60° C.-40% EtOAc/petroleum spirits 40-60° C. to provide the silane 4-2 as a yellow solid (1.40 g, 92%). ¹H NMR (500 MHz, $CDCl_3$) δ 0.29 (s, 9H), 0.98 (t, J=7.5 Hz, 3H), 1.52 (d, J=6.0 Hz, 6H), 1.68 (sext, J=7.5 Hz, 2H), 2.62 (t, J=7.5 Hz, 2H), 4.75 (sept, J=6.0 Hz, 1H), 6.85 (d, J=1.5 Hz, 1H), 8.22 (s, 1H), 8.79 (d, J=1.5 Hz, 1H).

7-Ethynyl-9-isopropoxy-3-propyl-4H-pyrido[1,2-a]pyrimidin-4-one (4-3)

9-Isopropoxy-3-propyl-7-((trimethylsoliyl)ethynyl)-4H-pyrido[1,2-a]pyrimidin-4-one 4-2 (1.40 g, 4.1 mmol) was dissolved in MeOH (20 mL), then $K_2CO_3$ (622 mg, 4.5 mmol) was added to the reaction. After stirring at rt for 15 min, the reaction diluted with ether (20 mL) and $H_2O$ (20 mL). The organic layer was separated and the aqueous layer was further extracted into ether (2×20 mL). Combined organic layers were washed with brine, dried over $Na_2SO_4$, filtered and concentrated to afford the acetylene 4-3 as an orange solid (950 mg, 86%). ¹H NMR (500 MHz, $CDCl_3$) δ0.98 (t, J=7.5 Hz, 3H), 1.53 (d, J=6.0 Hz, 6H), 1.68 (sext, J=7.5 Hz, 2H), 2.63 (t, J7.5 Hz, 2H), 3.20 (s, 1H), 4.74 (sept, J=6.0 Hz, 1H), 6.87 (d, J=1.5 Hz, 1H), 8.23 (s, 1H), 8.83 (s, J=2.0 Hz, 1H).

7-(1-Benzyl-1H-1,2,3-triazol-4-yl)-9-isopropoxy-3-propyl-4H-pyrido[1,2-a]pyrimidin-4-one (4-4)

7-Ethynyl-9-isopropoxy-3-propyl-4H-pyrido[1,2-a]pyrimidin-4-one (4-3) (200 mg, 0.74 mmol) was dissolved in EtOH (5 mL), then benzyl azide (125 mg, 0.94 mmol) in EtOH (5 mL) was added followed by $H_2O$ (10 mL). To the reaction was then added $CuSO_4.5H_2O$ (123 µL, 0.3M aqueous solution, 5 mol %), and sodium ascorbate (148 µL, 1M aqueous solution, 20 mol %) and the reaction was stirred in the dark for 24 h. The reaction was diluted with $H_2O$ and extracted into $CH_2Cl_2$ (×3). The organic layer was washed with brine, dried over $Na_2SO_4$, filtered, concentrated and purified by flash chromatography eluting with 10-40% EtOAc/petroleum spirits 40-60° C. to furnish the triazole 4-4 as a white solid (308 mg, quantitative yield). ¹H NMR (500 MHz, $CDCl_3$) δ0.98 (t, J=7.5 Hz, 3H), 1.56 (d, J=6.0 Hz, 6H), 1.68 (sext, J=7.5 Hz, 2H), 2.63 (t, J=7.5 Hz, 2H), 4.92 (sept, J=6.0 Hz, 1H), 5.62 (s, 2H), 7.38 (m, 5H), 7.72 (d, J=1.0 Hz, 1H), 7.83 (s, 1H), 8.25 (s, 1H), 8.86 (d, J=2.0 Hz, 1H).

7-(1-Benzyl-1H-1,2,3-triazol-4-yl)-9-hydroxy-3-propyl-4H-pyrido[1,2-a]pyrimidin-4-one (4-5)
(1616)

7-(1-Benzyl-1H-1,2,3-triazol-4-yl)-9-isopropoxy-3-propyl-4H-pyrido[1,2-a]pyrimidin-4-one 4-4 (300 mg, 0.74 mmol) was added to 48% aqueous HBr (4 mL) and the mixture was heated to reflux for 1 h. After cooling the reaction was neutralized with sat.aq. $NaHCO_3$ then extracted into $CH_2Cl_2$ (×3). The organic layer was washed with brine, dried over $Na_2SO_4$, filtered and concentrated to afford the product 4-5 as an off-white powder (256 mg, 95%). ¹H NMR (500 MHz, $CDCl_3$) δ1.00 (t, J=7.5 Hz, 3H), 1.70 (sext, J=7.5 Hz, 2H), 2.64 (t, J=7.5 Hz, 2H), 5.61 (s, 2H), 7.39 (m, 5H), 7.72 (d, J=1.5 Hz, 1H), 7.79 (s, 1H), 8.11 (s, 1H), 8.85 (d, J=1.5 Hz, 1H). HPLC $t_R$=11.13 min (93.5%). MS: m/z 362.1 [M+H]⁺.

TABLE 4

Compounds prepared according to Example 4 (Scheme 4)

| Compound | Structure | MW | ¹H NMR | MS |
|---|---|---|---|---|
| 1606 | 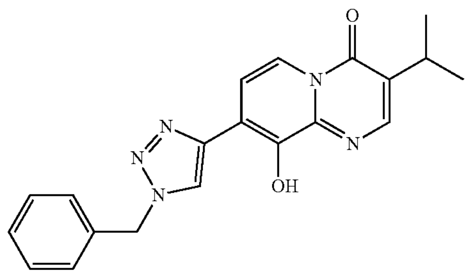 [SMILES: CC(C)c1cnc2c(O)c(-c3cn(Cc4ccccc4)nn3)ccn2c1=O] | 361.4 | ¹H NMR (500 MHz, $d_6$-DMSO) δ 1.26 (d, J = 6.5 Hz, 6H), 3.13 (sept, J = 7.0 Hz, 1H), 5.75 (s, 2H), 7.31-7.41 (m, 5H), 7.96 (d, J = 7.5 Hz, 1H), 8.21 (s, 1H), 8.52 (d, J = 8.0 Hz, 1H), 8.70 (s, 1H) | m/z 362.1 $[M + H]^+$ |
| 1615 | 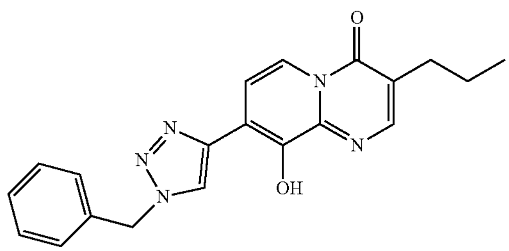 [SMILES: CCCc1cnc2c(O)c(-c3cn(Cc4ccccc4)nn3)ccn2c1=O] | 361.4 | ¹H NMR (500 MHz, $d_6$-DMSO) δ 0.92 (t, J = 7.5 Hz, 3H), 1.61 (sext, J = 7.5 Hz, 2H), 2.54 (t, J = 7.5 Hz, 2H), 5.75 (s, 2H), 7.37 (m, 4H), 7.96 (d, J = 7.5 Hz, 1H), 8.24 (s, 1H), 8.52 (d, J = 7.5 Hz, 1H), 8.70 (s, 1H). | m/z 362.1 $[M + H]^+$ |
| 1616 | 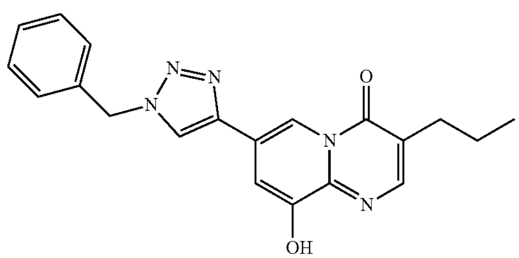 [SMILES: CCCc1cnc2c(O)cc(-c3cn(Cc4ccccc4)nn3)cn2c1=O] | 361.4 | ¹H NMR (500 MHz, $CDCl_3$) δ 1.00 (t, J = 7.5 Hz, 3H), 1.70 (sext, J = 7.5 Hz, 2H), 2.64 (t, J = 7.5 Hz, 2H), 5.61 (s, 2H), 7.39 (m, 5H), 7.72 (d, J = 1.5 Hz, 1H), 7.79 (s, 1H), 8.11 (s, 1H), 8.85 (d, J = 1.5 Hz, 1H) | m/z 362.1 $[M + H]^+$ |
| 1617 | 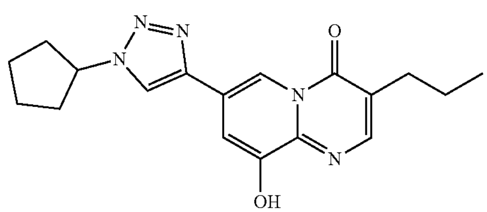 [SMILES: CCCc1cnc2c(O)cc(-c3cn(C4CCCC4)nn3)cn2c1=O] | 339.4 | ¹H NMR (500 MHz, $CDCl_3$): δ 1.01 (t, J = 7.5 Hz, 3H), 1.72 (sext, J = 7.5 Hz, 2H), 1.78-1.87 (m, 2H), 1.92-2.01 (m, 2H), 2.09-2.18 (m, 2H), 2.29-2.39 (m, 2H), 2.66 (t, J = 7.5 Hz, 2H), 5.02 (quint, J = 7.0 Hz, 1H), 7.76 (d, J = 1.5 Hz, 1H), 7.90 (s, 1H), 8.13 (s, 1H), 8.90 (d, J = 1.5 Hz, 1H); | m/z 340.1 $[M + H]^+$ |
| 1626 | 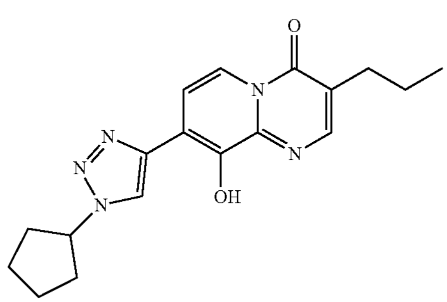 [SMILES: CCCc1cnc2c(O)c(-c3cn(C4CCCC4)nn3)ccn2c1=O] | 339.4 | ¹H NMR (500 MHz, $d_6$-DMSO) δ 0.94 (t, J = 7.0 Hz, 3H), 1.62 (m, 2H), 1.73 (m, 2H), 1.86 (m, 2H), 2.04 (m, 2H), 2.23 (m, 2H), 2.56 (t, J = 7.0 Hz, 3H), 5.15 (m, 1H), 8.01 (d, J = 7.5 Hz, 1H), 8.61 (d, J = 7.0 Hz, 1H), 8.25 (s, 1H), 8.61 (d, J = 7.5 Hz, 1H), 8.73 (s, 1H) | m/z 340.1 $[M + H]^+$ |

Example 5

A range of 9-hydroxy-4-oxo-4H-pyrido[1,2-a]pyrimidine carboxamides can be prepared by condensation of 3-hydroxy-2-amino pyridinols 1-3 with diethyl(ethoxymethylene) malonate to afford intermediate 5-1. Subsequent ring closure in boiling acetic acid provides the ethyl ester 5-2. Hydrolysis with 2N NaOH gives acid 5-3, followed by conversion to acid chloride 5-4 is achieved using thionyl chloride. Target compounds 5-5 are then synthesized by stirring acid chloride 5-4 with the appropriate amine (Scheme 5).

Scheme 5

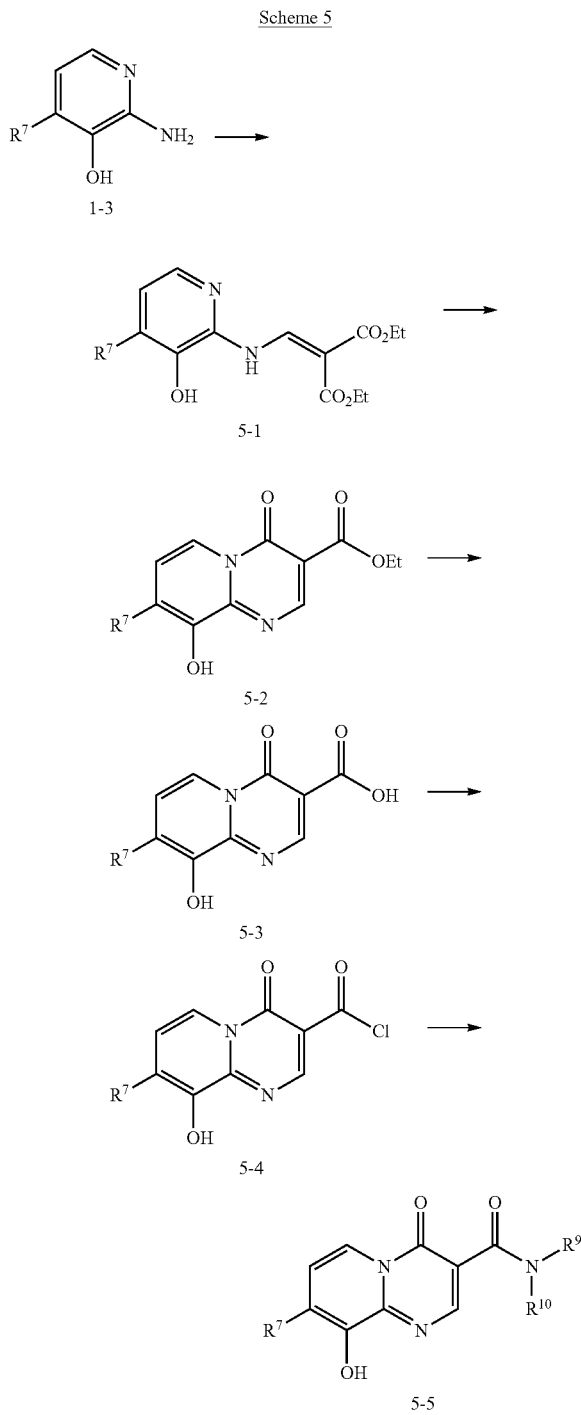

in which

R[7] is H or methyl;

R[9] is H;

R[10] is $C_{3-8}$alkyl optionally interrupted with O, $(CH_2)_{1-2}$ 5 or 6 membered N-containing heterocyclyl, $(CH_2)_{0-1}$ $C_{3-6}$cycloalkyl or $CH_2$ optionally substituted phenyl optionally fused with a 5 membered O containing heterocyclyl; or R[9] and R[10] together with the N to which they are attached form a 5 or 6 membered ring.

Compound 1460

Diethyl 2-((3-hydroxypyridin-2-ylamino)methylene)malonate (5-1)

2-Amino-3-hydroxypyridine (1-3) (20.0 g, 0.18 mol) and diethyl 2-(ethoxymethylene)malonate (55.0 mL, 0.27 mol) were stirred together in a flask at 130° C. for 40 min. The pyridine went into solution on heating after which a new yellow solid precipitated out of solution. The reaction was cooled and the solid was recrystallised (EtOH) and air dried affording the product 5-1 as a yellow solid (39.0 g, 77%). $^1$H NMR ($d_6$-DMSO, 500 MHz) δ1.20 (m, 6H), 4.17 (q, J=6.5 Hz, 2H), 4.22 (q, J=6.5 Hz, 2H), 7.10 (t, J=7.0 Hz, 1H), 7.32 (d, J=7.0 Hz, 1H), 7.87 (d, J=2.1 Hz, 1H), 9.13 (d, J=12.5 Hz, 1H), 10.88 (bs, 1H), 11.10 (d, J=12.5 Hz, 1H).

Ethyl-9-hydroxy-4-oxo-4H-pyrido[1,2-a]pyrimidine-3-carboxylate (5-2)

Diethyl-2-((3-hydroxypyridine-2-ylamin)methylene)malonate 5-1 (47.7 g, 0.17 mol) was heated to reflux in acetic acid (400 mL) for 4.5 h. The reaction was concentrated under reduced pressure to afford a yellow solid. Recrystalisation (ethanol) gave the desired product 5-2 as a pale yellow solid (30.6 g, 76%). $^1$H NMR ($d_6$-DMSO, 500 MHz) δ1.30 (t, J=7.0 Hz 3H), 4.26 (q, J=7 Hz, 2H), 7.41 (t, J=8.5 Hz, 1H), 7.49 (d, J=8.5 Hz, 1H), 7.63 (d, J=8.5 Hz, 1H), 7.80 (s, 1H).

9-Hydroxy-4-oxo-4H-pyrido[1,2-a]pyrimidine-3-carboxylic acid (5-3)

The ester (5-2) (5.0 g, 0.02 mol) was suspended in ethanol (400 mL) to which was added a 2N aqueous solution of sodium hydroxide (192 mL, 0.38 mol). The reaction was heated at 40° C. for 3 h in which time a bright yellow precipitate was evident in the reaction mixture. The ethanol was removed under reduced pressure and the aqueous solution was extracted with ethyl acetate (150 mL). The aqueous solution was acidified to pH 3 using 10% aqueous HCl solution and left for 17 h in the fridge. The reaction was filtered and the yellow solid was washed with water (20 mL) and dried under reduced pressure to give the title compound 5-3 as its HCl salt (4.17 g, 86%). $^1$H NMR ($D_2O$, 400 MHz) δ 2.74 (bs, 1H), 7.35 (br s, 2H), 8.61 (br s, 1H).

9-Hydroxy-4-oxo-4H-pyrido[1,2-a]pyrimidine-3-carbonyl chloride (5-4)

9-Hydroxy-4-oxo-4H-pyrido[1,2-a]pyrimidine-3-carboxylic acid (5-3) (4.3 g, 19.5 mmol) was heated to 80° C. in thionyl chloride for 2.5 h. The volatiles were removed in vacuo. Excess thionyl chloride was removed by azeotroping with toluene. The resulting 9-Hydroxy-4-oxo-4H-pyrido[1,2-a]pyrimidine-3-carbonyl chloride 5-4 was isolated in quantitative yield as a beige solid.

N-cyclohexyl-9-hydroxy-4-oxo-4H-pyrido[1,2-a]pyrimidine-3-carboxamide (5-5) (1460)

9-Hydroxy-4-oxo-4H-pyrido[1,2-a]pyrimidine-3-carboxylic acid (5-3) (4.3 g, 19.5 mmol) was heated to 80° C. in thionyl chloride for 2.5 h. The volatiles were removed in vacuo. Excess thionyl chloride was removed by azeotroping with toluene. The resulting acid chloride was isolated as a beige solid. The acid chloride (3.9 g, 17.4 mmol) was suspended in CH₂Cl₂ (65 mL) and cooled to 0° C. DIEA (4.0 mL) and cyclohexylamine (4.5 mL) were added and the reaction was stirred at rt for 2 days. Added 1M HCl until pH 3 followed by the addition of EtOH (65 mL). The suspension was filtered and the filtrate was concentrated to a volume of (10 mL). The solution was cooled and a green solid was collected by filtration washing with MeOH/H₂O (2:1) (×3) to afford the desired N-cyclohexyl-9-hydroxy-4-oxo-4H-pyrido[1,2-a]pyrimidine-3-carboxamide 5-4 (1.21 g, 24%). $^1$H NMR (400 MHz, d6-DMSO) δ1.30 (m, 4H), 1.39 (m, 1H), 1.39 (m, 2H), 1.87 (m, 1H), 3.86 (m, 1H), 7.48 (t, J=7.2 Hz, 1H), 7.53 (d, J=7.2 Hz, 1H), 8.71 (d, J=6.8 Hz, 1H), 8.99 (s, 1H). MS: m/z 288.1 [M+H]+.

TABLE 5

Compounds prepared according to Example 5 (Scheme 5)

| Compound | Structure | MW | $^1$H NMR | MS |
|---|---|---|---|---|
| 1394 | 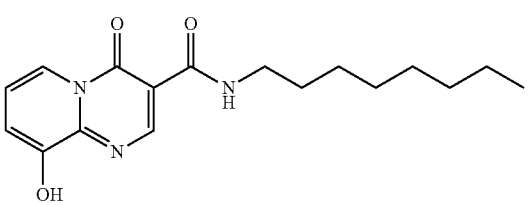 [SMILES: CCCCCCCCNC(=O)c1cnc2c(O)cccn2c1=O] | 317.4 | $^1$H NMR (400 MHz, d6-DMSO) δ 0.82 (m, 3H), 1.95 (m, 12H), 3.45 (m, 2H), 1.79 (m, 2H), 7.24 (m, 1H), 7.33 (d, J = 6.8 Hz, 1H), 8.68 (d, J = 6.8 Hz, 1H), 8.96 (br s, 1H), 9.24 (s, 1H). | m/z 316.2 [M + H]+ |
| 1422 | 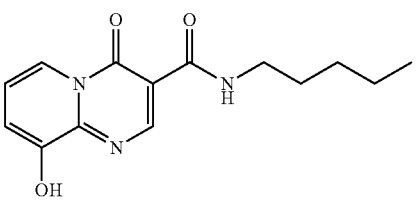 [SMILES: CCCCCNC(=O)c1cnc2c(O)cccn2c1=O] | 275.3 | $^1$H NMR (400 MHz, d6DMSO) δ 80.82 (s, 3H), 1.22 (m, 4H), 1.50 (m, 2H), 3.21 (m, 2H), 7.40 (s, 2H), 8.62 (s, 1H), 8.99 (s, 2H), 10.94 (br s, 1H). | m/z 276.2 [M + H]+ |
| 1423 | 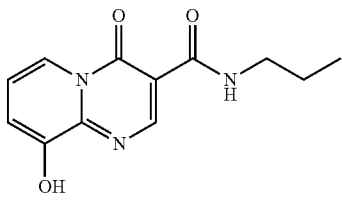 [SMILES: CCCNC(=O)c1cnc2c(O)cccn2c1=O] | 247.3 | $^1$H NMR (400 MHz, d6DMSO) δ 0.82 (m, 3H), 1.24 (q, J = 7.0 Hz, 2H), 3.29 (t, J = 7.0 Hz, 2H), 3.22 (m, 2H), 4.51 (s, 2H), 7.37 (m, 2H), 8.97 (s, 1H), 9.00 (m, 1H). | m/z 248.1 [M + H]+ |
| 1425 | 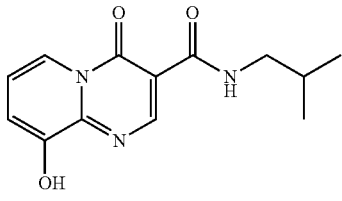 [SMILES: CC(C)CNC(=O)c1cnc2c(O)cccn2c1=O] | 261.3 | $^1$H NMR (400 MHz, d6-DMSO) δ 0.88 (s, 6H), 1.79 (m, 1H), 3.09 (m, 2H), 7.40 (s, 1H), 8.63 (s, 1H), 8.99 (s, 1H), 9.02 (s, 1H), 10.95 (s, 1H) | m/z 262.1 [M + H]+ |
| 1426 | 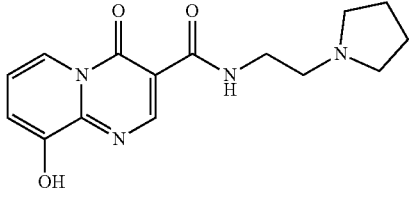 [SMILES: O=C(NCCN1CCCC1)c1cnc2c(O)cccn2c1=O] | 302.3 | $^1$H NMR (400 MHz, d6-DMSO) δ 1.70 (m, 4H), 2.61 (m, 4H), 2.77 (m, 2H), 3.51 (m, 2H), 7.20 (m, 2H), 8.38 (s, 1H), 8.82 (s, 1H), 9.02 (s, 1H). | m/z 303.2 [M + H]+ |
| 1427 | 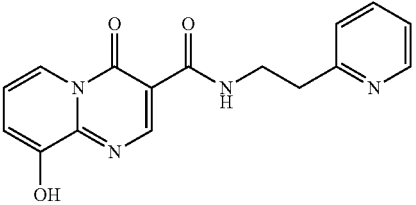 [SMILES: O=C(NCCc1ccccn1)c1cnc2c(O)cccn2c1=O] | 310.3 | $^1$H NMR (400 MHz, d6-DMSO) δ 2.99 (m, 2H), 3.68 (m, 2H), 7.18 (t, J = 7.2 Hz, 1H), 7.25 (d, J = 7.2 Hz, 1H), 7.41 (s, 1H), 7.63 (m, 1H), 8.40 (s, 1H), 8.60 (s, 1H), 8.97 (s, 1H), 9.05 (m, 1H) | No molecular ion observed |

TABLE 5-continued

Compounds prepared according to Example 5 (Scheme 5)

| Compound | Structure | MW | ¹H NMR | MS |
|---|---|---|---|---|
| 1428 | 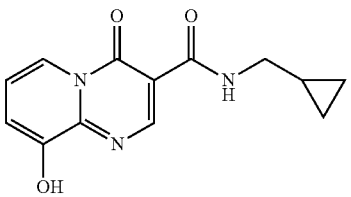 [SMILES: O=C(NCC1CC1)c1cnc2c(O)cccn2c1=O] | 259.3 | ¹H NMR (400 MHz, CDCl₃) δ 0.22 (m, 2H), 0.41 (m, 2H), 1.00 (m, 1H), 3.21 (m, 2H), 7.21 (m, 2H), 8.61 (s, 1H), 9.00 (s, 1H), 9.19 (s, 1H). | m/z 260.1 [M + H]⁺ |
| 1429 | 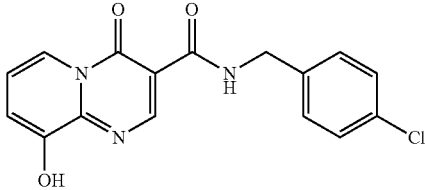 [SMILES: O=C(NCc1ccc(Cl)cc1)c1cnc2c(O)cccn2c1=O] | 329.7 | ¹H NMR (400 MHz, d6-DMSO) δ 4.55 (d, J = 6.0 Hz, 2H), 7.40 (m, 4H), 7.52 (t, J = 7.61, 1H), 7.61 (d, J = 7.6 Hz, 1H), 8.73 (d, J = 6.8 Hz, 1H), 8.95 (s, 1H), 9.38 (t, J = 6.0 Hz, 1H) | m/z 330.1 [M + H]⁺ |
| 1431 | 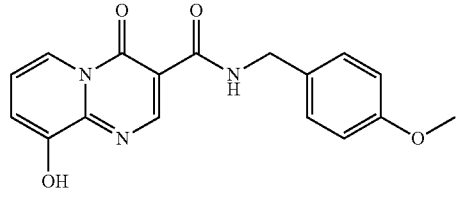 [SMILES: COc1ccc(CNC(=O)c2cnc3c(O)cccn3c2=O)cc1] | 325.3 | ¹H NMR (400 MHz, d6-DMSO) δ 3.72 (s, 3H), 4.49 (d, J = 6.0 Hz, 2H), 6.89 (d, J = 4.4 Hz, 2H), 7.27 (d, J = 4.4 Hz, 2H), 7.51 (t, J = 7.6 Hz, 1H), 7.57 (d, J = 7.6 Hz, 1H), 8.70 (d, J = 7.6 Hz, 2H), 8.98 (s, 1H), 9.27 (br s, 1H) | m/z 330.1 [M + H]⁺ |
| 1432 | 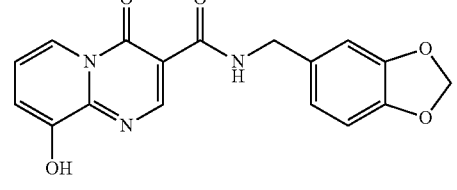 | 339.3 | ¹H NMR (400 MHz, d6-DMSO) δ 4.46 (d, J = 5.6 Hz, 2H), 5.97 (s, 2H), 6.83 (d, J = 8.0 Hz, 1H), 6.86 (d, J = 8.0 Hz, 1h), 6.92 (s, 1H), 7.46 (m, 2H), 8.69 (d, J = 6.4 Hz, 1H), 9.02 (s, 1H), 9.33 (t, J = 5.6 Hz, 1H) | m/z 340.1 [M + H]⁺ |
| 1433 | 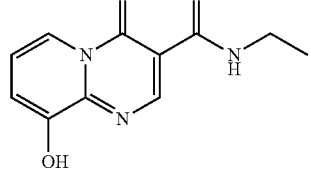 | 223.2 | ¹H NMR (400 MHz, d6-DMSO) δ 1.15 (t, J = 7.2 Hz, 3H), 3.38 (q, J = 7.2 Hz, 2H), 7.46 (m, 2H), 8.70 (m, 1H), 8.96 (t, J = 5.6 Hz, 1H), 9.00 (s, 1H), 10.97 (br s, 1H) | m/z 234.1 [M + H]⁺ |
| 1436 | 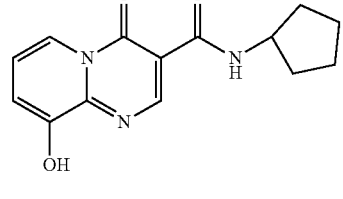 | 273.3 | ¹H NMR (400 MHz, d6-DMSO) δ 1.47 (m, 2H), 1.59 (m, 2H), 1.69 (m, 2H), 1.93 (m, 2H), 4.24 (m, 1H), 7.03 (d, J = 7.6 Hz, 1H), 7.29 (t, J = 7.2 Hz, 1H), 8.32 (d, J = 6.8 Hz, 1H), 8.88 (s, 1H), 9.13 (d, J = 7.6 Hz, 1H) | m/z 274.1 [M + H]⁺ |
| 1437 | 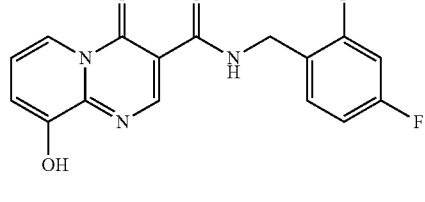 | 331.3 | ¹H NMR (400 MHz, d6-DMSO) δ 4.53 (d, J = 5.6 Hz, 2H), 7.00 (t, J = 7.2 Hz, 1H), 7.19 (m, 1H), 7.45 (m, 3H), 8.67 (d, J = 7.2 Hz, 1H), 8.91 (m, 1H), 9.37 (br m, 1H) | m/z 332.1 [M + H]⁺ |

TABLE 5-continued

Compounds prepared according to Example 5 (Scheme 5)

| Compound | Structure | MW | ¹H NMR | MS |
|---|---|---|---|---|
| 1440 | 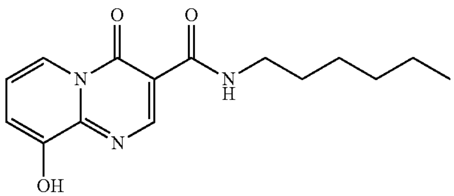 [SMILES: CCCCCCNC(=O)c1cnc2c(O)cccn2c1=O] | 289.3 | ¹H NMR (400 MHz, d6-DMSO) δ 0.84 (m, 3H), 1.25 (m, 6H), 1.52 (m, 2H), 7.42 (m, 2H), 8.70 (m, 1H), 9.01 (m, 2H), 11.00 (br s, 1H) | m/z 290.1 [M + H]+ |
| 1441 | 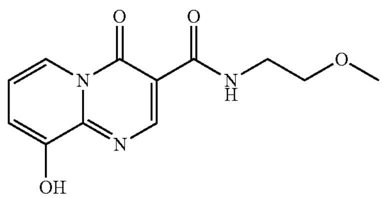 [SMILES: COCCNC(=O)c1cnc2c(O)cccn2c1=O] | 263.3 | ¹H NMR (400 MHz, d6-DMSO) δ 3.21 (s, 3H), 3.49 (m, 4H), 7.41 (m, 2H), 8.65 (m, 1H), 9.01 (s, 1H), 9.17 (m, 1H). | m/z 290.1 [M + H]+ |
| 1445 | 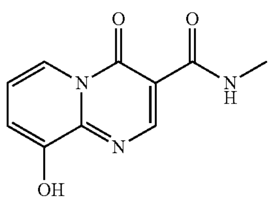 [SMILES: CNC(=O)c1cnc2c(O)cccn2c1=O] | 219.2 | ¹H NMR (400 MHz, d6-DMSO) δ 2.87 (d, J = 4.4 Hz, 3H), 7.40 (m, 2H), 8.69 (d, J = 5.6 Hz, 1H), 8.87 (d, J = 4.4 Hz, 1H), 8.99 (s, 1H), 10.98 (br s, 1H) | m/z 220.1 [M + H]+ |
| 1446 | 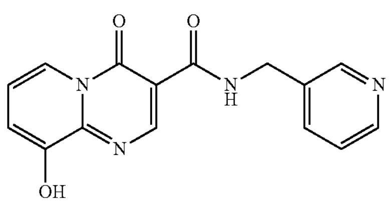 [SMILES: O=C(NCc1cccnc1)c1cnc2c(O)cccn2c1=O] | 296.3 | ¹H NMR (400 MHz, d6-DMSO) δ 4.59 (d, J = 6.0 Hz, 2H), 7.35 (m, 1H), 7.45 (m, 2H), 7.75 (d, J = 8.0 Hz, 1H), 8.45 (d, J = 4.4 Hz, 1H), 8.58 (s, 1H), 8.70 (m, 1H), 9.01 (s, 1H), 8.47 (br t, J = 6.0 Hz, 1H). | m/z 297.1 [M + H]+ |
| 1447 | 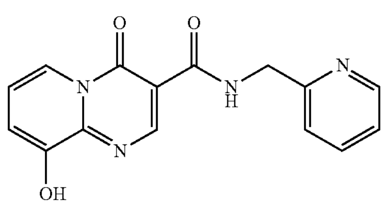 [SMILES: O=C(NCc1ccccn1)c1cnc2c(O)cccn2c1=O] | 296.3 | ¹H NMR (400 MHz, d6-DMSO) δ 4.89 (d, J = 6.0 Hz, 2H), 7.50 (t, J = 7.2 Hz, 1H), 7.58 (d, J = 7.2 Hz, 1H), 7.80 (m, 2H), 8.35 (t, J = 7.1 Hz, 1H), 8.76 (m, 2H). | m/z 297.1 [M + H]+ |
| 1450 | 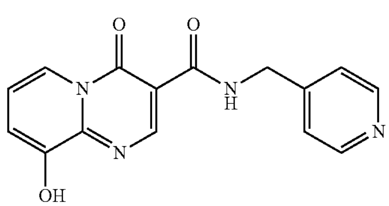 [SMILES: O=C(NCc1ccncc1)c1cnc2c(O)cccn2c1=O] | 296.3 | ¹H NMR (400 MHz, d6-DMSO) δ 4.81 (d, J = 4.8 Hz, 2H), 7.52 (m, 2H), 7.89 (d, J = 5.2 Hz, 2H), 8.75 (d, J = 6.8 Hz, 1H), 8.80 (d, J = 4.2 Hz, 2H), 8.98 (s, 1H), 9.66 (br s, 1H). | m/z 297.1 [M + H]+ |
| 1452 | 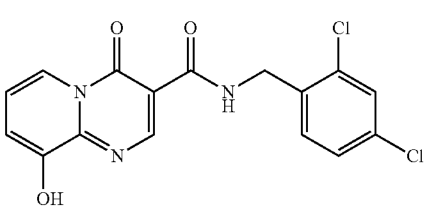 [SMILES: O=C(NCc1ccc(Cl)cc1Cl)c1cnc2c(O)cccn2c1=O] | 364.2 | ¹H NMR (400 MHz, d6-DMSO) δ 4.61 (d, J = 6.0 Hz, 2H), 7.41 (s, 2H), 7.46 (m, 2H), 8.72 (d, J = 7.5 Hz, 1H), 9.00 (s, 1H), 9.49 (t, J = 6.0 Hz, 1H) | m/z 364.0 [M + H]+ |

TABLE 5-continued

Compounds prepared according to Example 5 (Scheme 5)

| Compound | Structure | MW | ¹H NMR | MS |
|---|---|---|---|---|
| 1453 | 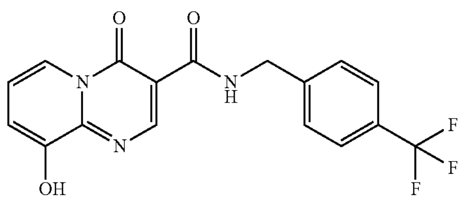 [SMILES: O=C(NCc1ccc(C(F)(F)F)cc1)c1cnc2c(O)cccn2c1=O] | 363.3 | ¹H NMR (400 MHz, d6-DMSO) δ 4.64 (d, J = 6.0 Hz, 2H), 7.39 (m, 2H), 7.58 (d, J = 4.0 Hz, 2H), 7.71 (d, J = 4.0 Hz, 2H), 8.68 (d, J = 7.5 Hz, 1H), 9.00 (s, 1H), 9.43 (t, J = 6.0 Hz, 1H) | m/z 364.1 [M + H]⁺ |
| 1454 | 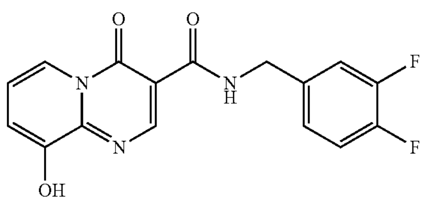 [SMILES: O=C(NCc1ccc(F)c(F)c1)c1cnc2c(O)cccn2c1=O] | 331.3 | ¹H NMR (400 MHz, d6-DMSO) δ 4.54 (d, J = 6.0 Hz, 2H), 7.20 (m, 1H), 7.41 (m, 4H), 8.70 (d, J = 6.0 Hz, 1H), 9.01 (s, 1H), 9.45 (t, J = 6.0 Hz, 1H). | m/z 332.1 [M + H]⁺ |
| 1461 | 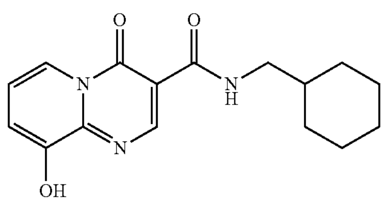 [SMILES: O=C(NCC1CCCCC1)c1cnc2c(O)cccn2c1=O] | 301.4 | ¹H NMR (400 MHz, d6-DMSO) δ 0.96 (m, 2H), 1.11 (m, 3H), 1.42 (m, 1H), 1.60 (m, 5H), 3.20 (t, J = 6.0 Hz, 2H), 7.43 (t, J = 7.2 Hz, 1H), 7.53 (d, J = 7.2 Hz, 1H), 8.75 (d, J = 7.2 Hz, 1H), 8.99 (s, 1H), 9.02 (t, J = 6.0 Hz, 1H). | m/z 302.1 [M + H]⁺ |
| 1462 | 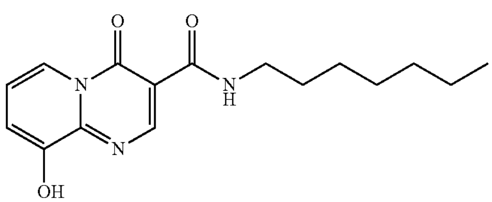 [SMILES: CCCCCCCNC(=O)c1cnc2c(O)cccn2c1=O] | 305.4 | ¹H NMR (400 MHz, d6-DMSO) δ 0.85 (t, J = 4.2 Hz, 3H), 1.25 (m, 8H), 1.53 (t, J = 6.0 Hz, 2H), 3.33 (m, 2H), 7.51 (t, J = 6.8 Hz, 1H), 7.60 (d, J = 6.8 Hz, 1H), 8.73 (d, J = 6.8 Hz, 1H), 8.92 (t, J = 6.0 Hz, 1H), 8.94 (s, 1H) | m/z 306.2 [M + H]⁺ |
| 1532 | 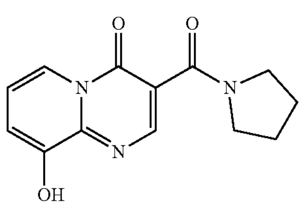 [SMILES: O=C(c1cnc2c(O)cccn2c1=O)N1CCCC1] | 259.26 | ¹H NMR (400 MHz, d6-DMSO) δ 1.88 (m, 4H), 3.56 (m, 4H), 7.35 (bs, 2H), 8.36 (bs, 1H), 8.57 (bs, 1H). | m/z 260.2 [M + H]⁺ |
| 1533 | 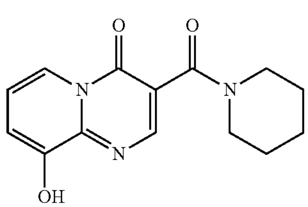 [SMILES: O=C(c1cnc2c(O)cccn2c1=O)N1CCCCC1] | 273.29 | ¹H NMR (400 MHz, d6-DMSO) δ 1.54 (m, 6H), 3.21 (m, 2H), 3.59 (m, 2H), 7.12 (bs, 2H), 8.29 (bs, 1H), 8.51 (bs, 1H). | m/z 274.3 [M + H]⁺ |
| 1649 | 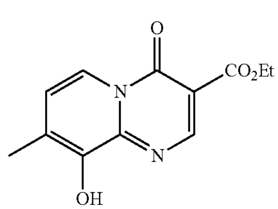 [SMILES: CCOC(=O)c1cnc2c(O)c(C)ccn2c1=O] | 248.2 | ¹H NMR (500 MHz, d₆-DMSO) δ 1.29 (t, J = 7 Hz, 3H), 3.30 (s, 3H), 4.26 (q, J = 7 Hz, 2H), 7.77 (d, J = 8.5 Hz, 1H), 8.07 (d, J = 8.5 Hz, 1H), 8.82 (s, 1H), 8.98 (s, 1H). | m/z 248.9 [M − H]⁺ |

Example 6

2-Methylamino substituted pyrimidones can be prepared according to Scheme 6. Taking aniline 1-3 and heating with ethyl chloroacetoacetate in PPA following the procedure of Ferrarini, P. L *II Farmaco* 1995, 50(1), p 69-72 generates after work-up the desired chloromethyl derivative 6-1. Substitution of the chloro substituent with a variety of amines generates the target amino compounds 6-2 (Scheme 6).

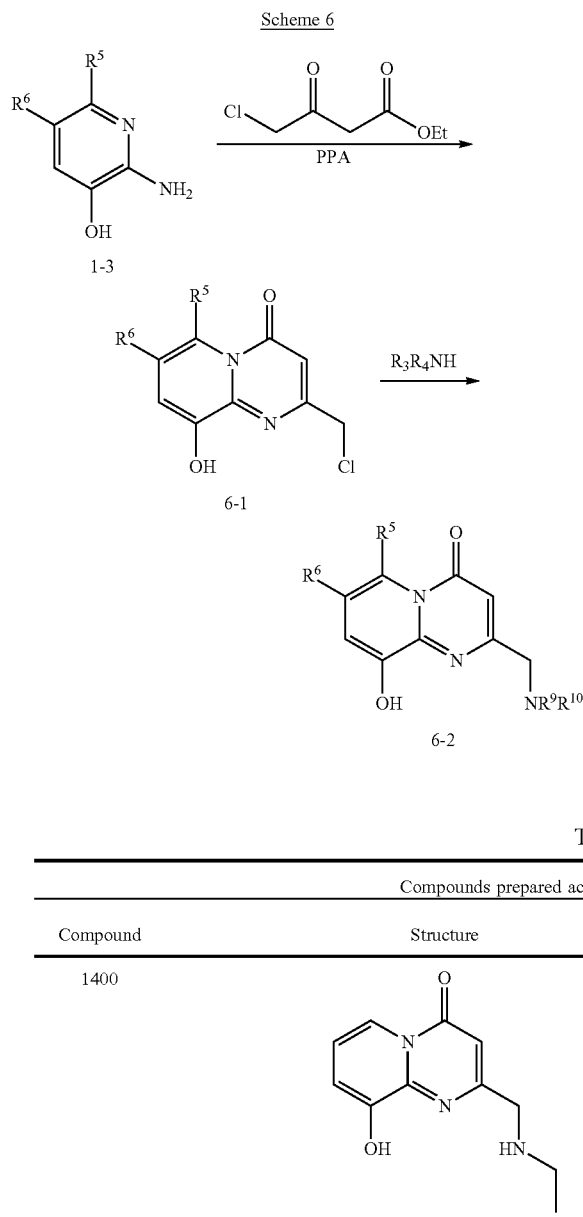

Scheme 6 in which $R^5$ is H or methyl;
$R^6$ is H or Cl;
$R^9$ and $R^{10}$ are independently selected from H, $C_{1-8}$alkyl, CN, $(CH_2)_{0-2}$ $C_{3-6}$ cycloalkyl, $CH_2$ optionally substituted phenyl or $(CH_2)_{0-3}$ optionally substituted N containing 5 or 6 membered heterocyclyl; or
$R^9$ and $R^{10}$ together with the N to which they are attached from an optionally substituted 5 or 6 membered ring.

Compound 1408

2-(Chloromethyl)-9-hydroxy-4H-pyrido[1,2-a]pyrimidin-4-one (6-1)

2-Amino-3-hydroxy pyridine (5.1 g, 46.3 mmol) was heated together with Ethyl chloroacetoacetate (6.0 mL, 44.1 mmol) in polyphosphoric acid (60 g) at 110° C. for 2 h. The reaction was cooled then ice was added. Then 2N NaOH was carefully added until pH 4. The resulting beige precipitate was collected by filtration and dried to afford the 2-(chloromethyl)-9-hydroxy-4H-pyrido[1,2-a]pyrimidin-4-one 6-1 (4.73 g, 49%) as a light brown solid. $^1$H NMR (400 MHz, d6-DMSO) δ4.62 (s, 2H), 6.43 (s, 1H), 7.20 (m, 2H), 8.40 (d, J=6.8 Hz, 1H).

9-Hydroxy-2-((isobutylamino)methyl)-4H-pyrido[1,2-a]pyrimidin-4-one hydrogen chloride (6-2)

To 2-(chloromethyl)-9-hydroxy-4H-pyrido[1,2-a]pyrimidin-4-one (6-1) (206 mg, 0.978 mmol) in anhydrous MeOH (5 mL) at 0° C. was added isobutylamine (0.5 mL, 5.03 mmol). The mixture was then stirred at rt overnight. Solvent was removed in vacuo and EtOH (5 mL) and conc. HCl (1 mL) were added. The product precipitated out and was collected by filtration washing with cold ethanol. The resulting 9-hydroxy-2-((isobutylamino)methyl)-4H-pyrido[1,2-a]pyrimidin-4-one hydrogen chloride 6-2 was isolated as a beige solid (82 mg, 30%). $^1$H NMR (400 MHz, DMSO) δ0.93 (t, J=7.0 Hz, 3H), 1.64 (m, 2H), 2.85 (m, 2H), 4.20 (s, 2H), 6.39 (s, 1H), 7.22 (t, J=7.2 Hz, 1H), 7.31 (d, J=7.2 Hz, 1H), 8.42 (d, J=7.2 Hz, 1H), 9.03 (br s, 2H), 10.2 (br s, 1H). MS: m/z 248.1 [M+H]$^+$.

TABLE 6

Compounds prepared according to Example 6 (Scheme 6)

| Compound | Structure | MW | $^1$H NMR | MS |
|---|---|---|---|---|
| 1400 | 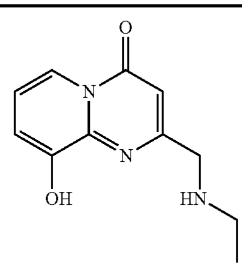 | 219.24 | $^1$H NMR (400 MHz, DMSO) δ 1.23 (t, J = 7.2 Hz, 1H), 2.99 (m, 2H), 4.23 (s, 2H), 6.42 (s, 1H), 7.27 (d, J = 7.2 Hz, 1H), 7.33 (d, J = 7.2 Hz, 1H), 9.21 (br s, 2H), 10.2 (s, 1H) | m/z 220.1 [M + H]$^+$ |
| 1401 | 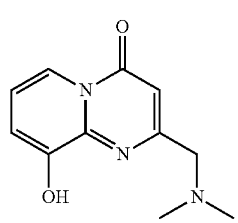 [SMILES: CN(C)Cc1cc(=O)n2cccc(O)c2n1] | 219.24 | $^1$H NMR (400 MHz, DMSO) δ 2.78 (s, 3H), 2.79 (s, 3H), 4.39 (s, 2H), 6.41 (s, 1H), 7.26 (t, J = 7.2 Hz, 1H), 7.30 (d, J = 7.2 Hz, 1H), 8.42 (d, J = 7.2 Hz, 1H), 10.2 (s, 1H), 10.7 (s, 1H) | m/z 220.1 [M + H]$^+$ |

TABLE 6-continued

Compounds prepared according to Example 6 (Scheme 6)

| Compound | Structure | MW | ¹H NMR | MS |
|---|---|---|---|---|
| 1402 | 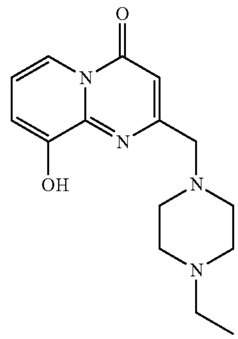 [SMILES: CCN1CCN(Cc2cc(=O)n3cccc(O)c3n2)CC1] | 288.35 | ¹H NMR (400 MHz, DMSO) δ 1.24 (t, J = 7.0 Hz, 3H), 3.13 (m, 2H), 3.33 (br m, 3H), 3.51 (br m, 5 H), 4.02 (br s, 2H), 7.25 (t, J = 6.8 Hz, 1H), 7.30 (d, J = 7.2 Hz, 1H), 8.47 (d, J = 6.8 Hz, 1H). | m/z 289.2 [M + H]⁺ |
| 1403 | 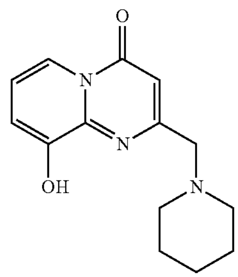 [SMILES: O=c1cc(CN2CCCCC2)nc2c(O)cccn12] | 259.30 | ¹H NMR (400 MHz, DMSO) δ 1.43 (m, 2H), 1.75 (s, 2H), 2.01 (m, 2H), 2.97 (m, 2H), 3.42 (m, 2H), 6.49 (s, 1H), 7.28 (t, J = 7.6 Hz, 1H), 7.33 (d, J = 7.6 Hz, 1H), 8.45 (d, J = 7.6 Hz, 1H), 10.4 (br s, 1H), 10.6 (br s, 1H). | m/z 260.1 [M + H]⁺ |
| 1404 | 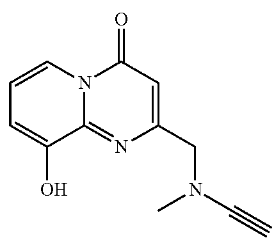 | 243.3 | ¹H NMR (400 MHz, DMSO) δ 2.45 (s, 2H), 2.92 (s, 3H), 3.13 (s, 1H), 3.62 (s, 1H), 6.43 (s, 1H), 7.24 (t, J = 7.2 Hz, 1H), 7.34 (d, J = 7.2 Hz, 1H), 8.43 (d, J = 7.2 Hz, 1H). | m/z 244.1 [M + H]⁺ |
| 1405 | 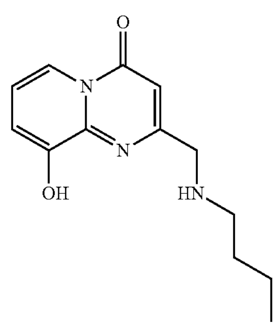 [SMILES: CCCCNCc1cc(=O)n2cccc(O)c2n1] | 247.3 | ¹H NMR (400 MHz, DMSO) δ 0.89 (t, J = 7.6 Hz, 3H), 1.33 (m, 2H), 1.67 (m, 2H), 2.97 (m, 2H), 4.28 (s, 2H), 6.46 (s, 1H), 7.31 (t, J = 7.6 Hz, 1H), 7.37 (d, J = 7.6 Hz, 1H), 8.48 (d, J = 7.2 Hz, 1H), 9.21 (br s, 2H), 10.2 (br s, 1H). | m/z 248.1 [M + H]⁺ |
| 1406 | 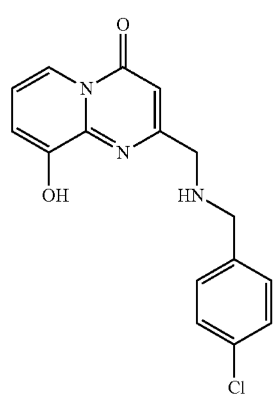 [SMILES: O=c1cc(CNCc2ccc(Cl)cc2)nc2c(O)cccn12] | 315.8 | ¹H NMR (400 MHz, d6-DMSO) δ 3.77 (s, 2H), 4.83 (s, 2H), 6.45 (s, 1H), 7.18 (m, 2H), 7.37 (m, 4H), 8.38 (d, J = 7.2 Hz, 1H). | m/z 316.1 [M + H]⁺ |

TABLE 6-continued

Compounds prepared according to Example 6 (Scheme 6)

| Compound | Structure | MW | ¹H NMR | MS |
|---|---|---|---|---|
| 1407 | 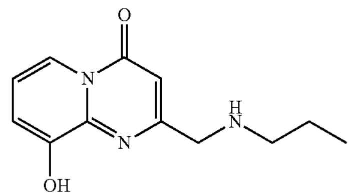 [SMILES: CCCNCc1cc(=O)n2cccc(O)c2n1] | 233.3 | ¹H NMR (400 MHz, DMSO) δ 0.93 (t, J = 7.0 Hz, 3H), 1.64 (m, 2H), 2.85 (m, 2H), 4.20 (s, 2H), 6.39 (s, 1H), 7.22 (t, J = 7.2 Hz, 1H), 7.31 (d, J = 7.2 Hz, 1H), 8.42 (d, J = 7.2 Hz, 1H), 9.03 (br s, 2H), 10.2 (br s, 1H). | m/z 220.1 [M + H]⁺ |
| 1408 | 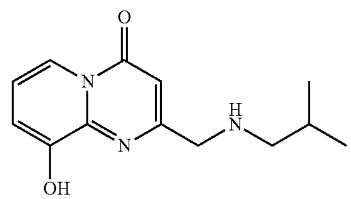 [SMILES: CC(C)CNCc1cc(=O)n2cccc(O)c2n1] | 247.3 | ¹H NMR (400 MHz, DMSO) δ 0.95 (t, J = 7.0 Hz, 6H), 1.99 (m, 1H), 2.89 (m, 2H), 4.21 (s, 2H), 6.42 (s, 1H), 7.24 (t, J = 7.0 Hz, 1H), 7.37 (d, J = 7.2 Hz, 1H), 8.42 (d, J = 7.0 Hz, 1H), 9.18 (br s, 2H), 10.2 (br s, 1H). | m/z 248.1 [M + H]⁺ |
| 1409 | 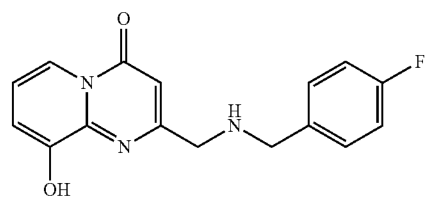 [SMILES: O=c1cc(CNCc2ccc(F)cc2)nc2c(O)cccn12] | 299.3 | ¹H NMR (400 MHz, DMSO) δ 4.21 (br m, 4H), 6.39 (s, 1H), 7.24 (m, 4H), 7.58 (m, 2H), 8.40 (d, J = 7.2 Hz, 1H), 9.75 (br s, 2H), 10.2 (br s, 1H), | m/z 300.1 [M + H]⁺ |
| 1410 | 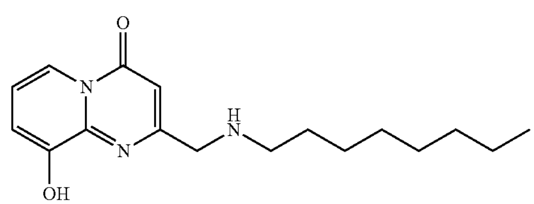 [SMILES: CCCCCCCCNCc1cc(=O)n2cccc(O)c2n1] | 303.4 | ¹H NMR (400 MHz, DMSO) δ 0.88 (t, J = 7.0 Hz, 2H), 1.19 (m, 10H), 2.95 (b s, 2H), 4.21 (s, 2H), 6.40 (s, 1H), 7.23 (t, J = 7.0 Hz, 1H), 7.35 (d, J = 7.0 Hz, 1H), 8.41 (d, J = 7.0 Hz, 1H), 9.16 (br s, 2H), 10.2 (br s, 1H) | m/z 304.2 [M + H]⁺ |
| 1411 | 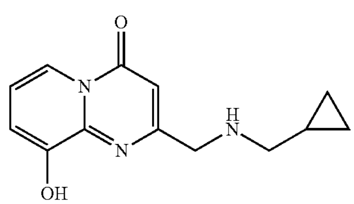 [SMILES: O=c1cc(CNCC2CC2)nc2c(O)cccn12] | 245.3 | ¹H NMR (400 MHz, DMSO) δ 0.21 (m, 2H), 0.52 (m, 2H), 1.05 (m, 1H), 2H), 2.90 (s, 2H), 4.21 (s, 2H), 6.39 (s, 1H), 7.21 (t, J = 7.0 Hz, 1H), 7.32 (d, J = 7.0 Hz, 1H), 8.41 (d, J = 7.0 Hz, 1H), 9.40 (br s, 2H), 10.2 (br s, 1H). | m/z 246.1 [M + H]⁺ |
| 1412 | 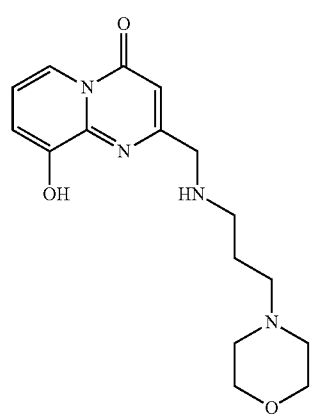 [SMILES: O=c1cc(CNCCCN2CCOCC2)nc2c(O)cccn12] | 318.4 | ¹H NMR (400 MHz, D2O) δ 2.11 (m, 2H), 3.11 (br m, 6H), 3.59 (br m, 2H), 3.66 (br m, 2H) 3.92 (br m, 2H), 4.24 (s, 2H), 6.37 (s, 1H), 7.15 (t, J = 7.6 Hz, 1H), 7.24 (d, J = 7.6 Hz, 1H), 8.36 (d, J = 7.6 Hz, 1H). | m/z 319.2 [M + H]⁺ |

TABLE 6-continued

Compounds prepared according to Example 6 (Scheme 6)

| Compound | Structure | MW | ¹H NMR | MS |
|---|---|---|---|---|
| 1413 | 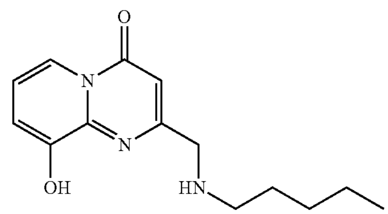 [SMILES: CCCCCNCc1cc(=O)n2cccc(O)c2n1] | 261.3 | ¹H NMR (400 MHz, d6 DMSO) δ 0.93 (t, J = 7 Hz, 3H), 1.22 (m, 4H), 1.61 (m, 2H), 2.97 (m, 2H), 4.21 (s, 2H), 6.41 (s, 1H), 7.23 (t, J = 7.0 Hz, 1H), 7.28 (d, J = 7 Hz, 1H), 8.42 (d, J = 7 Hz, 1H), 9.00 (br s, 2H). | m/z 262.1 [M + H]⁺ |
| 1414 | 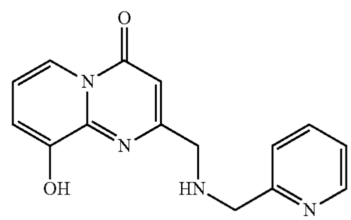 [SMILES: O=c1cc(CNCc2ccccn2)nc2c(O)cccn12] | 282.3 | ¹H NMR (400 MHz, d6 DMSO) δ 4.23 (s, 2H), 4.38 (s, 2H), 6.40 (s, 1H), (t, J = 7 Hz, 3H), 1.22 (m, 4H), 1.61 (m, 2H), 2.97 (m, 2H), 4.21 (s, 2H), 6.41 (s, 1H), 7.23 (t, J = 7.2 Hz, 1H), 7.35 (d, J = 7.2 Hz, 1H), 7.41 (d, J = 7.0 Hz, 1H), 7.82 (m, 1H), 8.43 (d, J = 7.2 Hz, 1H), 8.63 (s, 1H), 9.79 (br s, 2H). | m/z 283.1 [M + H]⁺ |
| 1415 | 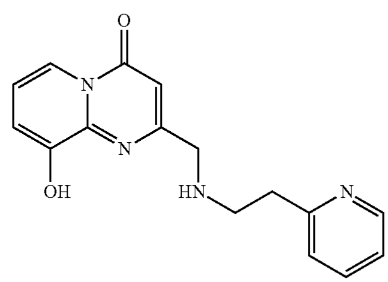 [SMILES: O=c1cc(CNCCc2ccccn2)nc2c(O)cccn12] | 296.3 | ¹H NMR (400 MHz, d6 DMSO) δ 3.20 (t, J = 7.0 Hz, 2H), 3.39 (t, J = 7.0 Hz, 2H), 4.25 (s, 2H), 6.40 (s, 1H), 7.22 (m, 4H), 7.66 (t, J = 7.2 Hz, 1H), 8.42 (d, J = 7.2 Hz, 2H) | m/z 297.2 [M + H]⁺ |
| 1416 | 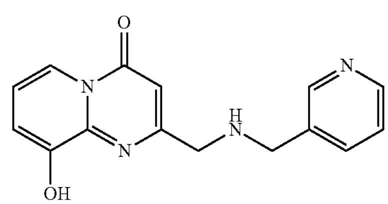 [SMILES: O=c1cc(CNCc2cccnc2)nc2c(O)cccn12] | 288.3 | ¹H NMR (400 MHz, D20) δ 2.13 (br s, 4H), 3.69 (m, 2H), 3.42 (m, 4H), 3.75 (m, 2H), 4.51 (s, 2H), 6.58 (s, 1H), 7.36 (t, J = 7.2 Hz, 1H), 7.45 (d, J = 7.2 Hz, 1H), 8.57 (d, J = 7.2 Hz, 1H). | m/z 289.2 [M + H]⁺ |
| 1417 | 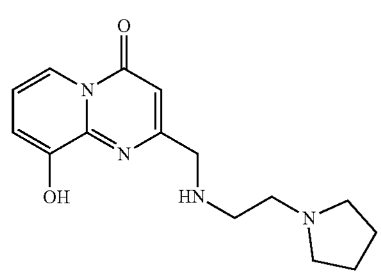 [SMILES: O=c1cc(CNCCN2CCCC2)nc2c(O)cccn12] | 288.3 | ¹H NMR (400 MHz, D20) δ 2.12 (m, 4H), 3.42 (m, 4H), 3.66 (m, 2H), 3.76 (m, 2H), 4.51 (s, 2H), 6.58 (s, 1H), 7.36 (t, J = 7.2 Hz, 1H), 7.45 (d, J = 7.2 Hz, 1H), 8.57 (d, J = 7.2 Hz, 1H). | m/z 289.2 [M + H]⁺ |
| 1418 | 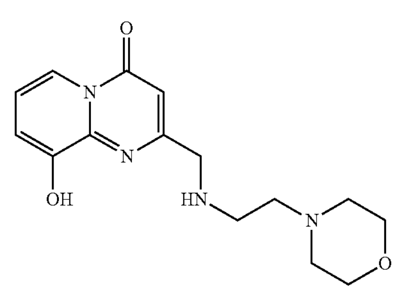 [SMILES: O=c1cc(CNCCN2CCOCC2)nc2c(O)cccn12] | 304.3 | ¹H NMR (400 MHz, D20) δ 2.79 (m, 5H), 3.01 (m, 2H), 3.37 (m, 2H), 3.80 (m, 4H), 4.37 (m, 2H), 6.57 (s, 1H), 7.34 (t, J = 7.2 Hz, 1H), 7.40 (d, J = 7.2 Hz, 1H), 8.44 (d, J = 7.2 Hz, 1H). | m/z 305.2 [M + H]⁺ |

TABLE 6-continued

Compounds prepared according to Example 6 (Scheme 6)

| Compound | Structure | MW | ¹H NMR | MS |
|---|---|---|---|---|
| 1435 | 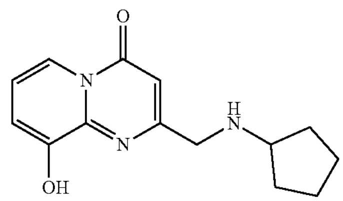 [SMILES: O=c1cc(CNC2CCCC2)nc2c(O)cccn12] | 259.3 | ¹H NMR (400 MHz, d6-DMSO) δ 1.43 (m, 2H), 1.69 (m, 4H), 1.95 (m, 2H), 3.48 (m, 1H), 4.21 (s, 2H), 6.41 (s, 1H), 7.25 (t, J = 7.2 Hz, 1H), 7.37 (d, J = 7.2 Hz, 1H), 8.40 (d, J = 7.2 Hz, 1H), 9.38 (br s, 2H), 10.21 (br s, 1H). | m/z 260.3 [M + H]⁺ |
| 1438 | 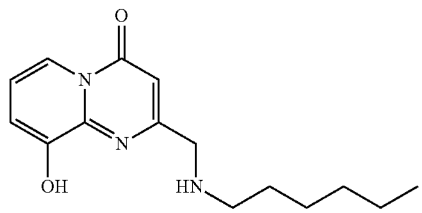 [SMILES: CCCCCCNCc1cc(=O)n2cccc(O)c2n1] | 275.4 | ¹H NMR (400 MHz, d4-MeOH) δ 0.91 (s, 3H), 1.23 (m, 6H), 1.57 (m, 2H), 2.61 (t, J = 7.2 Hz, 2H), 3.82 (s, 2H), 6.20 (s, 1H), 6.79 (s, 1H), 7.02 (t, J = 7.2 Hz, 1H), 8.03 (d, J = 7.2 Hz, 1H). | m/z 276.3 [M + H]⁺ |
| 1439 | 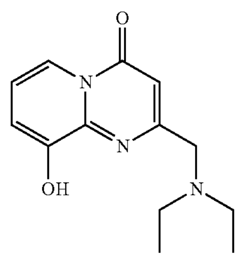 [SMILES: CCN(CC)Cc1cc(=O)n2cccc(O)c2n1] | 247.3 | ¹H NMR (400 MHz, d4-MeOD) δ 1.22 (t, J = 7.2 Hz, 6H), 3.02 (q, J = 7.2 Hz, 4H), 4.14 (s, 2H), 6.34 (s, 1H), 7.00 (d, J = 6.8 Hz, 1H), 7.17 (t, J = 6.8 Hz, 1H), 8.25 (d, J = 6.8 Hz, 1H). | m/z 248.3 [M + H]⁺ |
| 1442 | 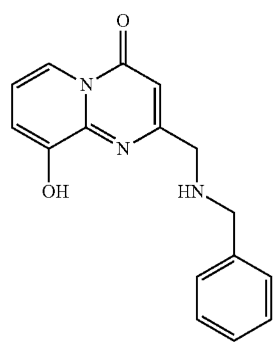 [SMILES: O=c1cc(CNCc2ccccc2)nc2c(O)cccn12] | 281.3 | ¹H NMR (400 MHz, d6-DMSO) δ 4.19 (s, 2H), 6.38 (s, 1H), 7.22 (t, J = 7.2 Hz, 1H), 7.35 (m, 4H), 7.52 (m, 2H), 8.41 (d, J = 7.2 Hz, 1H), 9.66 (br s, 2H), 10.15 (br s, 1H). | m/z 282.1 [M + H]⁺ |
| 1443 | 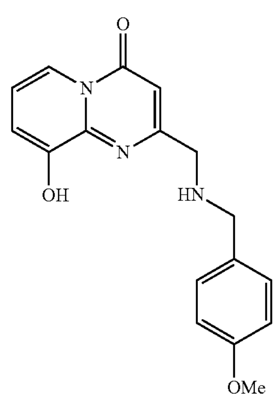 [SMILES: COc1ccc(CNCc2cc(=O)n3cccc(O)c3n2)cc1] | 311.3 | ¹H NMR (400 MHz, d6-DMSO) δ 3.64 (s, 3H), 4.02 (s, 2H), 4.03 (s, 2H), 6.35 (s, 1H), 6.83 (d, J = 4.8 Hz, 2H), 7.22 (d, J = 7.2 Hz, 1H), 7.33 (d, J = 7.2 Hz, 1H), 7.42 (d, J = 4.8 Hz, 2H), 8.40 (d, J = 7.2 Hz, 1H), 9.74 (br s, 2H), 10.15 (br s, 1H) | m/z 312.1 [M + H]⁺ |

TABLE 6-continued

Compounds prepared according to Example 6 (Scheme 6)

| Compound | Structure | MW | ¹H NMR | MS |
|---|---|---|---|---|
| 1444 | (9-hydroxy-4-oxo-4H-pyrido[1,2-a]pyrimidin-2-yl)methyl-(2,4-difluorophenyl)amine | 303.3 | ¹H NMR (400 MHz, d6-DMSO) δ 4.23 (s, 2H), 6.06 (s, 1H), 6.20 (s, 1H), 6.57 (t, J = 7.6 Hz, 1H), 7.77 (t, J = 7.6 Hz, 1H), 7.05 (d, J = 7.2 Hz, 1H), 7.19 (d, J = 7.2 Hz, 1H), 8.40 (d, J = 7.2 Hz, 1H), 10.35 (br s, 1H) | m/z 304.4 [M + H]⁺ |
| 1448 | (9-hydroxy-4-oxo-4H-pyrido[1,2-a]pyrimidin-2-yl)methyl-(pyridin-3-yl)amine | 268.3 | ¹H NMR (400 MHz, d6-DMSO) δ 4.20 (s, 1H), 6.24 (s, 1H), 6.35 (br s, 1H), 6.51 (m, 3H), 7.02 (m, 2H), 7.14 (s, 1H), 7.19 (s, 1H), 8.39 (s, 1H). | m/z 267.1 [M − H]⁺ |
| 1449 | (9-hydroxy-4-oxo-4H-pyrido[1,2-a]pyrimidin-2-yl)methyl-phenylamine | 267.3 | ¹H NMR (400 MHz, d6-DMSO) δ 4.29 (s, 2H), 6.32 (s, 1H), 6.40 (br s, 1H), 6.55 (t, J = 7.5 Hz, 1H), 6.62 (d, J = 7.5 Hz, 1H), 7.07 (t, J = 7.5 Hz, 2H), 7.19 (t, J = 7.5 Hz, 1H), 7.25 (d, J = 7.5 Hz, 1H), 8.43 (d, J = 7.5 Hz, 1H). | m/z 267.9 [M − H]⁺ |
| 1451 | (9-hydroxy-4-oxo-4H-pyrido[1,2-a]pyrimidin-2-yl)methyl-(4-fluorophenyl)amine | 285.3 | ¹H NMR (400 MHz, d6-DMSO) δ 4.20 (s, 2H), 6.23 (s, 1H), 6.56 (m, 2H), 6.83 (d, J = 7.5 Hz, 1H), 7.15 (d, J = 7.5 Hz, 1H), 7.21 (d, J = 7.5 Hz, 1H), 8.39 (s, 1H) | m/z 285.9 [M + H]⁺ |
| 1455 | (9-hydroxy-4-oxo-4H-pyrido[1,2-a]pyrimidin-2-yl)methyl-(4-trifluoromethylbenzyl)amine | 349.3 | ¹H NMR (400 MHz, d6-DMSO) δ 4.21 (s, 2H), 4.30 (s, 2H), 6.39 (s, 1H), 7.21 (t, J = 6.8 Hz, 1H), 7.29 (d, J = 6.8 Hz, 1H), 7.76 (m, 4H), 8.40 (d, J = 6.8 Hz, 1H), 9.95 (br s, 2H), 10.19 (s, 1H). | m/z 350.1 [M + H]⁺ |

TABLE 6-continued

Compounds prepared according to Example 6 (Scheme 6)

| Compound | Structure | MW | ¹H NMR | MS |
|---|---|---|---|---|
| 1456 | 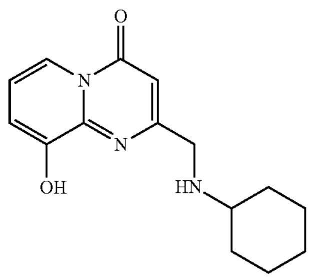 [SMILES: O=c1cc(CNC2CCCCC2)nc2c(O)cccn12] | 273.3 | ¹H NMR (400 MHz, d6-DMSO) δ 1.05 (m, 4H), 1.33 (m, 2H), 1.58 (m, 1H), 1.73 (m, 2H), 2.02 (m, 2H), 3.00 (m, 1H), 4.22 (s, 2H), 6.43 (s, 1H), 7.24 (d, J = 7.5 Hz, 1H), 7.35 (d, J = 7.5 Hz, 1H), 8.43 (s, 1H). | m/z 274.1 [M + H]⁺ |
| 1457 | 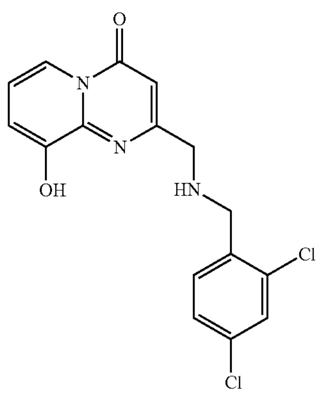 [SMILES: O=c1cc(CNCc2ccc(Cl)cc2Cl)nc2c(O)cccn12] | 350.2 | ¹H NMR (400 MHz, d6-DMSO) δ 3.64 (s, 2H), 4.61 (s, 2H), 6.42 (s, 2H), 7.19 (m, 2H), 7.38 (m, 1H), 7.55 (s, 1H), 7.58 (m, 1H), 8.41 (s, 1H). | m/z 351.1 [M + H]⁺ |
| 1458 | 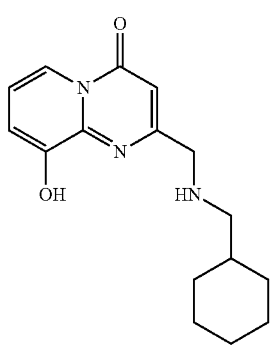 [SMILES: O=c1cc(CNCC2CCCCC2)nc2c(O)cccn12] | 287.4 | ¹H NMR (400 MHz, d6-DMSO) δ 0.88 (m, 2H), 1.09 (m, 4H), 1.65 (m, 6H), 2.89 (s, 2H), 4.20 (s, 2H), 6.41 (s, 1H), 7.22 (t, J = 6.8 Hz, 1H), 7.29 (d, J = 6.8 Hz, 1H), 8.42 (d, J = 6.8 Hz, 1H), 9.16 (s, 2H), 10.18 (s, 1H). | m/z 288.2 [M + H]⁺ |
| 1459 | 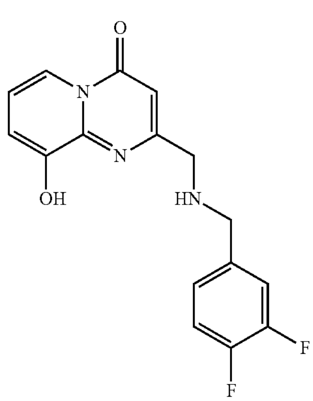 [SMILES: O=c1cc(CNCc2ccc(F)c(F)c2)nc2c(O)cccn12] | 317.3 | ¹H NMR (400 MHz, d6-DMSO) δ 3.92 (s, 2H), 4.17 (d, J = 6.0 Hz, 2H), 6.38 (s, 1H), 7.39 (m, 4H), 7.73 (t, J = 6.8 Hz, 1H), 8.41 (s, 1H), 8.55 (br s, 2H), 10.02 (br s, 1H). | m/z 318.1 [M + H]⁺ |

TABLE 6-continued

Compounds prepared according to Example 6 (Scheme 6)

| Compound | Structure | MW | ¹H NMR | MS |
|---|---|---|---|---|
| 1463 | 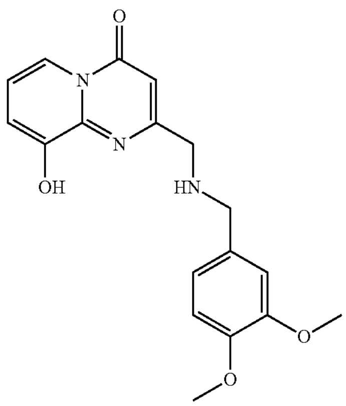 [SMILES: COc1ccc(CNCc2cc(=O)n3cccc(O)c3n2)cc1OC] | 341.4 | ¹H NMR (400 MHz, d6-DMSO) δ 3.65 (s, 3H), 3.66 (s, 3H), 3.67 (s, 2H), 4.60 (s, 2H), 6.38 (s, 1H), 6.81 (s, 2H), 6.96 (m, 2H), 7.09 (t, J = 7.2 Hz, 1H), 8.23 (d, J = 7.2 Hz, 1H). | m/z 342.2 [M + H]⁺ |
| 1464 | 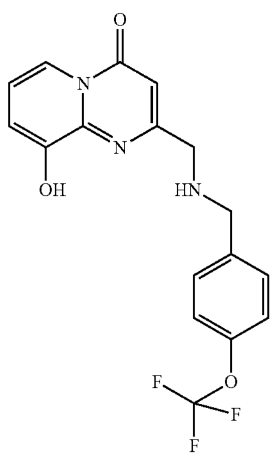 [SMILES: O=c1cc(CNCc2ccc(OC(F)(F)F)cc2)nc2c(O)cccn12] | 365.3 | ¹H NMR (400 MHz, d6-DMSO) δ 4.00 (d, J = 6.0 Hz, 2H), 4.62 (s, 2H), 6.44 (s, 1H), 7.19 (t, J = 7.2 Hz, 1H), 7.26 (d, J = 7.2 Hz, 1H), 7.35 (d, J = 7.6 Hz, 2H), 7.57 (d, J = 7.6 Hz, 2H), 8.37 (br s, 2H), 8.43 (d, J = 7.2 Hz, 1H) | m/z 366.1 [M + H]⁺ |
| 1466 | 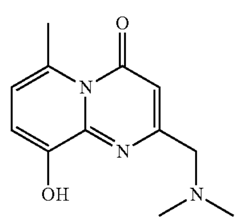 [SMILES: Cc1ccc(O)c2nc(CN(C)C)cc(=O)n12] | 233.3 | ¹H NMR (400 MHz, d6-DMSO) δ 2.77 (s, 3H), 2.79 (s, 6H), 4.25 (s, 2H), 6.80 (d, J = 7.2 Hz, 1H), 7.05 (d, J = 7.2 Hz, 1H), 9.60 (s, 1H), 10.37 (br s, 1H). | m/z 233.9 [M + H]⁺ |
| 1467 | 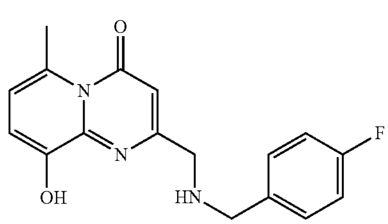 [SMILES: Cc1ccc(O)c2nc(CNCc3ccc(F)cc3)cc(=O)n12] | 313.3 | ¹H NMR (500 MHz, d6-DMSO) δ 2.77 (s, 3H), 3.65 (s, 2H), 4.58 (s, 2H), 6.29 (s, 1H), 6.75 (d, J = 7.2 Hz, 1H), 6.98 (d, J = 7.2 Hz, 1H), 7.08 (m, 2H), 7.33 (m, 2H). | No Molecular ion observed |
| 1468 | 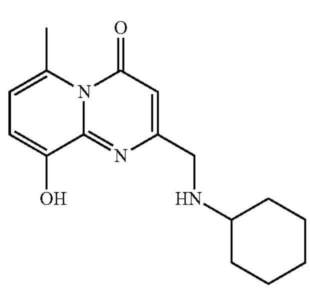 [SMILES: Cc1ccc(O)c2nc(CNC3CCCCC3)cc(=O)n12] | 287.4 | ¹H NMR (400 MHz, d6-DMSO) δ 1.11 (m, 3H), 1.97 (m, 2H), 1.55 (m, 1H), 1.63 (m, 2H), 2.01 (m, 2H), 2.81 (m, 3H), 2.99 (m, 1H), 4.14 (d, J = 6.0 Hz, 2H), 6.24 (s, 1H), 6.80 (d, J = 7.2 Hz, 1H), 7.05 (d, J = 7.2 Hz, 1H), 9.37 (br s, 2H), 9.71 (s, 1H). | m/z 288.1 [M + H]⁺ |

TABLE 6-continued

Compounds prepared according to Example 6 (Scheme 6)

| Compound | Structure | MW | ¹H NMR | MS |
|---|---|---|---|---|
| 1469 | 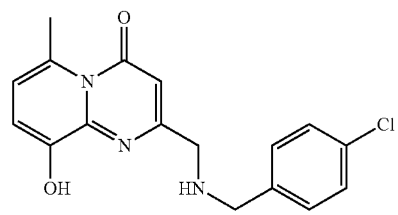 [SMILES: Cc1ccc(O)c2nc(CNCc3ccc(Cl)cc3)cc(=O)n12] | 329.8 | ¹H NMR (400 MHz, d6-DMSO) δ 2.79 (s, 3H), 3.62 (s, 2H), 4.77 (s, 2H), 6.27 (s, 1H), 6.72 (d, J = 7.2 Hz, 1H), 6.98 (d, J = 7.2 Hz, 1H), 7.33 (m, 4H). | No Molecular ion observed |
| 1470 | 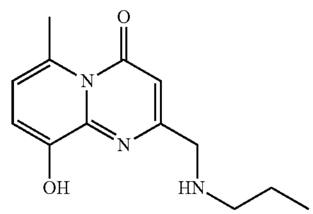 [SMILES: CCCNCc1cc(=O)n2c(C)ccc(O)c2n1] | 247.3 | ¹H NMR (400 MHz, d6-DMSO) δ 0.91 (t, J = 7.2 Hz, 3H), 1.61 (m, 2H), 2.79 (s, 3H), 2.81 (t, J = 7.2 Hz, 2H), 6.22 (s, 1H), 6.80 (d, J = 7.2 Hz, 1H), 7.04 (d, J = 7.2 Hz, 1H) | m/z 248.1 [M + H]⁺ |
| 1471 | 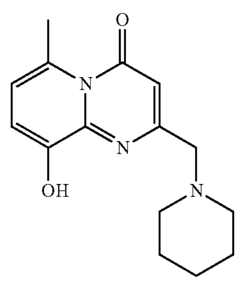 [SMILES: Cc1ccc(O)c2nc(CN3CCCCC3)cc(=O)n12] | 273.3 | ¹H NMR (400 MHz, d6-DMSO) δ 1.63 (m, 6H), 2.79 (s, 3H), 2.95 (m, 2H), 3.23 (m, 2H), 4.22 (s, 2H), 6.23 (s, 1H), 6.80 (d, J = 6.8 Hz, 1H), 7.03 (d, J = 6.8 Hz, 1H), 9.77 (s, 1H), 10.35 (br s, 1H) | m/z 274.2 [M + H]⁺ |
| 1476 | 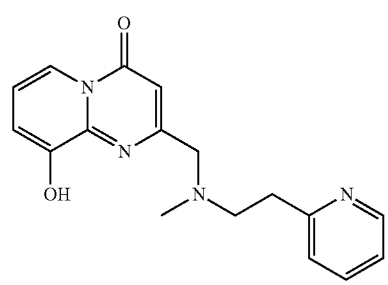 [SMILES: CN(CCc1ccccn1)Cc1cc(=O)n2cccc(O)c2n1] | 310.4 | ¹H NMR (400 MHz, d6-DMSO) δ 2.82 (s, 3H), 3.50 (s, 4H), 4.55 (s, 2H), 6.43 (s, 1H), 7.24 (m, 2H), 7.78 (t, J = 6.8 Hz, 1H), 7.89 (d, J = 6.8 Hz, 1H), 8.35 (t, J = 6.8 Hz, 1 Hz), 8.42 (d, J = 6.8 Hz, 1H), 8.73 (s, 1H). | m/z 311.1 [M + H]⁺ |
| 1478 | 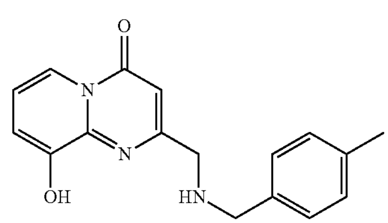 [SMILES: Cc1ccc(CNCc2cc(=O)n3cccc(O)c3n2)cc1] | 311.4 | ¹H NMR (400 MHz, d6-DMSO) δ 2.20 (s, 3H), 3.68 (s, 2H), 4.59 (s, 2H), 6.39 (s, 1H), 6.99 (d, J = 6.8 Hz, 1H), 7.10 (m, 4H), 7.19 (d, J = 8.2 Hz, 2H), 8.22 (d, J = 6.8 Hz, 1H). | No molecular ion observed |
| 1479 | 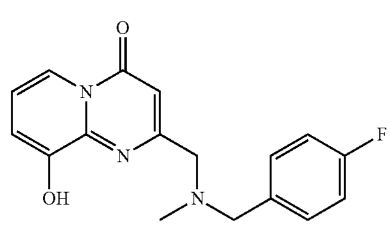 [SMILES: CN(Cc1ccc(F)cc1)Cc1cc(=O)n2cccc(O)c2n1] | 313.3 | ¹H NMR (500 MHz, d6-DMSO) δ 2.77 (s, 3H), 3.65 (s, 2H), 4.58 (s, 2H), 6.29 (s, 1H), 6.75 (d, J = 7.2 Hz, 1H), 6.98 (d, J = 7.2 Hz, 1H), 7.08 (m, 2H), 7.33 (m, 2H) | m/z 314.2 [M + H]⁺ |

TABLE 6-continued

Compounds prepared according to Example 6 (Scheme 6)

| Compound | Structure | MW | ¹H NMR | MS |
|---|---|---|---|---|
| 1485 | 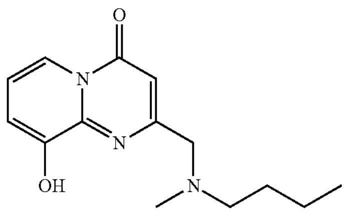 [SMILES: CCCCN(C)Cc1cc(=O)n2cccc(O)c2n1] | 261.3 | ¹H NMR (400 MHz, d6-DMSO) δ 0.92 (t, J = 7.2 Hz, 3H), 1.22 (m, 2H), 1.65 (m, 2H), 2.79 (s, 3H), 4.39 (br m, 2H), 3.05 (m, 2H), 7.21 (t, J = 7.2 Hz, 1H), 7.29 (d, J = 7.2 Hz, 1H), 8.42 (s, 1H), 9.98 (br s, 1H), 10.04 (s, 1H) | m/z 262.1 [M + H]⁺ |
| 1490 | 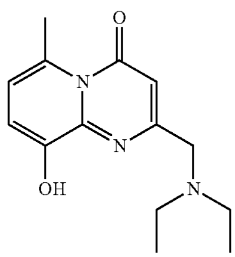 [SMILES: CCN(CC)Cc1cc(=O)n2c(C)ccc(O)c2n1] | 261.3 | ¹H NMR (400 MHz, d6-DMSO) δ 1.09 (t, J = 7.2 Hz, 6 Hz), 2.80 (s, 3H), 3.11 (m, 4H), 4.24 (s, 2H), 6.21 (s, 1H), 6.79 (d, J = 6.8 Hz, 1H), 7.03 (d, J = 6.8 Hz, 1H), 9.69 (s, 1H), 10.01 (br s, 1H) | m/z 262.1 [M + H]⁺ |
| 1491 | 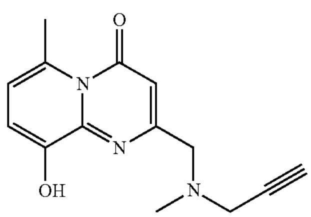 [SMILES: C#CCN(C)Cc1cc(=O)n2c(C)ccc(O)c2n1] | 257.3 | ¹H NMR (400 MHz, d6-DMSO) δ 2.79 (s, 3H), 3.90 (s, 1H), 4.16 (s, 2H), 4.38 (s, 2H). 6.28 (s, 1H), 6.80 (d, J = 7.2 Hz, 1H), 7.01 (d, J = 7.2 Hz, 1H), 9.59 (s, 1H), 11.02 (br s, 1H) | m/z 258.1 [M + H]⁺ |
| 1500 | 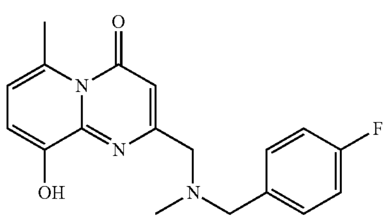 [SMILES: Cc1ccc(O)c2nc(CN(C)Cc3ccc(F)cc3)cc(=O)n12] | 327.4 | ¹H NMR (400 MHz, d6-DMSO) δ 2.76 (s, 3H), 2.80 (s, 3H), 4.21 (s, 2H), 4.38 (s, 2H), 6.81 (d, J = 6.8 Hz, 1H), 7.07 (d, J = 6.8 Hz, 1H), 7.21 (m, 2H), 7.60 (m, 2H), 9.68 (s, 1H), 10.59 (s, 1H) | m/z 328.5 [M + H]⁺ |
| 1503 | 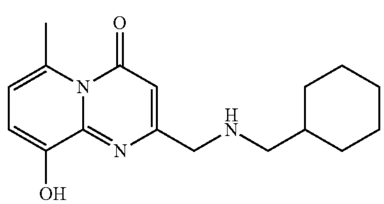 [SMILES: Cc1ccc(O)c2nc(CNCC3CCCCC3)cc(=O)n12] | 301.4 | ¹H NMR (400 MHz, d6-DMSO) δ 0.85 (m, 2H), 1.11 (m, 4H), 1.61 (m, 3H), 1.75 (m, 2H), 2.75 (m, 2H), 2.80 (s, 3H), 4.04 (s, 2H), 6.21 (s, 1H), 6.80 (d, J = 6.8 Hz, 1H), 7.05 (d, J = 6.8 Hz, 1H), 9.18 (br s, 2H), 9.60 (s, 1H) | m/z 302.7 [M + H]⁺ |
| 1504 | 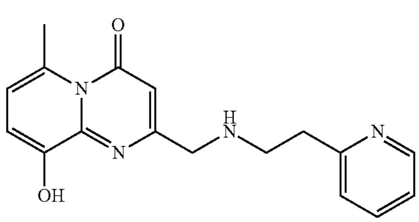 [SMILES: Cc1ccc(O)c2nc(CNCCc3ccccn3)cc(=O)n12] | 310.4 | ¹H NMR (400 MHz, d6-DMSO) δ 2.80 (s, 3H), 3.41 (m, 2H), 3.55 (m, 2H), 4.22 (s, 2H), 6.25 (s, 1H), 6.80 (d, J = 6.8 Hz, 1H), 7.06 (d, J = 6.8 Hz, 1H), 7.79 (t, J = 7.2 Hz, 1H), 7.94 (d, J = 7.2 Hz, 1H), 8.37 (d, J = 7.2 Hz, 1H), 8.77 (d, J = 6.8 Hz, 1H), 9.66 (br s, 1H). | m/z 311.7 [M + H]⁺ |

TABLE 6-continued

Compounds prepared according to Example 6 (Scheme 6)

| Compound | Structure | MW | ¹H NMR | MS |
|---|---|---|---|---|
| 1506 | 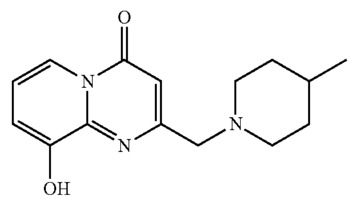 [SMILES: CC1CCN(Cc2cc(=O)n3cccc(O)c3n2)CC1] | 273.3 | ¹H NMR (400 MHz, d6-DMSO) δ 0.87 (m, 3H), 1.62 (m, 5 H), 3.01 (m, 2H), 3.43 (m, 2H), 4.35 (s, 2H), 6.21 (s, 1H), 8.41 (s, 1H), 10.10 (br s, 1H), 10.29 (br s, 1H) | m/z 274.3 [M + H]⁺ |
| 1508 | 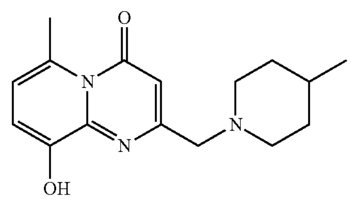 [SMILES: Cc1ccc(O)c2nc(CN3CCC(C)CC3)cc(=O)n12] | 287.4 | ¹H NMR (400 MHz, d6-DMSO) δ 0.90 (s, 3H), 1.63 (m, 5H), 2.81 (s, 3H), 2.95 (m, 2H), 3.39 (m, 2H), 4.21 (s, 2H), 6.23 (s, 1H), 6.80 (d, J = 6.8 Hz, 1H), 7.02 (d, J = 6.8 Hz, 1H), 9.76 (br s, 1H), 10.21 (br s, 1H). | m/z 288.4 [M + H]⁺ |
| 1515 | 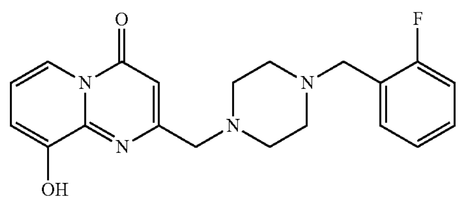 [SMILES: O=c1cc(CN2CCN(Cc3ccccc3F)CC2)nc2c(O)cccn12] | 368.4 | ¹H NMR (500 MHz, d6-DMSO) δ 3.71 (br m, 8H), 4.40 (s, 3H), 4.58 (s, 2H), 6.51 (s, 1H), 7.37 (m, 3H), 7.55 (m, 1H), 7.77 (m, 1H), 8.48 (d, J = 8.5 Hz, 1H), 10.28 (br s, 1H). | m/z 369.4 [M + H]⁺ |
| 1516 | 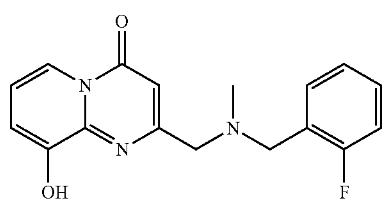 [SMILES: CN(Cc1cc(=O)n2cccc(O)c2n1)Cc1ccccc1F] | 313.3 | ¹H NMR (400 MHz, d6-DMSO) δ 2.81 (s, 3H), 4.22 (s, 2H), 6.39 (s, 1H), 7.25 (m, 4H), 7.42 (m, 1H), 7.71 (m, 1H), 8.43 (s, 1H), 10.2 (s, 1H), 10.65 (br s, 1H) | m/z 314.3 [M + H]⁺ |
| 1517 | 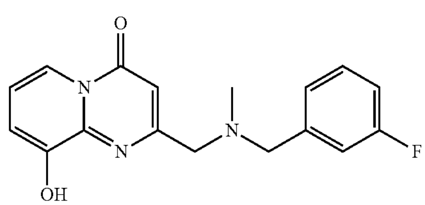 [SMILES: CN(Cc1cccc(F)c1)Cc1cc(=O)n2cccc(O)c2n1] | 313.3 | ¹H NMR (400 MHz, d6-DMSO) δ 2.81 (s, 3H), 4.35 (s, 2H), 4.44 (s, 2H), 6.38 (s, 1H), 7.23 (m, 3H), 7.39 (m, 2H), 7.57 (m, 1H), 8.43 (s, 1H), 10.26 (br s, 1H), 10.83 (br s, 1H) | m/z 314.3 [M + H]⁺ |
| 1518 | 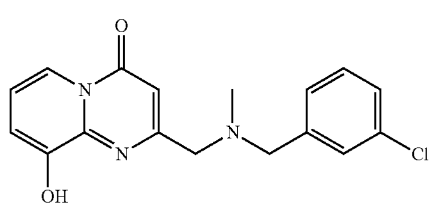 [SMILES: CN(Cc1cccc(Cl)c1)Cc1cc(=O)n2cccc(O)c2n1] | 329.8 | ¹H NMR (400 MHz, d6-DMSO) δ 2.80 (s, 3H), 4.37 (s, 2H), 4.43 (s, 2H), 6.35 (s, 1H), 7.38 (m, 3H), 7.59 (s, 1H), 7.77 (s, 1H), 8.41 (s, 1H), 10.25 (br s, 1H), 11.07 (br s, 1H) | m/z 330.3 [M + H]⁺ |
| 1519 | 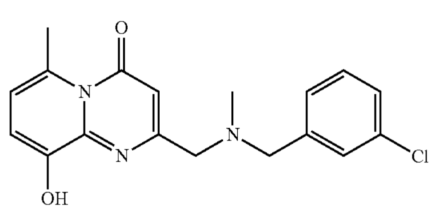 [SMILES: Cc1ccc(O)c2nc(CN(C)Cc3cccc(Cl)c3)cc(=O)n12] | 348.8 | ¹H NMR (400 MHz, d6-DMSO) δ 2.83 (s, 3H), 4.22 (s, 2H), 4.35 (s, 2H), 6.18 (s, 1H), 6.82 (d, J = 7.2 Hz, 1H), 7.10 (d, J = 7.2 Hz, 1H), 7.41 (m, 2H), 7.55 (m, 1H), 7.67 (s, 1H), 9.65 (s, 1H), 10.60 (br s, 1H). | m/z 344.3 [M + H]⁺ |

TABLE 6-continued

Compounds prepared according to Example 6 (Scheme 6)

| Compound | Structure | MW | ¹H NMR | MS |
|---|---|---|---|---|
| 1521 | (structure) | 287.4 | ¹H NMR (400 MHz, d6-DMSO) δ 1.12 (m, 1H), 1.20 (m, 2H), 1.51 (m, 4H), 1.76 (m, 2H), 2.10 (m, 2H), 2.75 (s, 3H), 3.20 (m, 1H), 4.21 (m, 1H), 4.56 (m, 1H), 6.43 (s, 1H), 7.24 (m, 2H), 8.41 (d, J = 6.8 Hz, 1H), 10.35 (br s, 1H), 10.43 (br s, 1H). | m/z 288.3 [M + H]⁺ |
| 1522 | (structure) | 382.4 | ¹H NMR (400 MHz, d6-DMSO) δ 2.84 (s, 3H), 3.51 (m, 8H), 4.32 (br s, 2H), 4.41 (s, 2H), 6.27 (s, 1H), 6.84 (d, J = 6.8 Hz, 1H), 7.11 (d, J = 6.8 Hz, 1H) 7.28 (m, 2H), 7.46 (m, 1H), 7.68 (m, 1H), 9.79 (br s, 1H). | m/z 383.4 [M + H]⁺ |
| 1523 | (structure) | 301.4 | ¹H NMR (400 MHz, d6-DMSO) δ 1.05 (m, 1H), 1.22 (m, 2H), 1.43 (m, 2H), 1.51 (m, 1H), 1.76 (m, 2H), 2.09 (m, 2H), 2.66 (s, 3H), 2.81 (s, 3H), 3.19 (m, 1H), 4.10 (m, 1H), 4.41 (m, 1H), 6.80 (d, J = 6.8 Hz, 1H), 7.09 (d, J = 6.8 Hz, 1H), 9.79 (s, 1H), 10.08 (br s, 1H). | m/z 302.4 [M + H]⁺ |
| 1525 | (structure) | 327.4 | ¹H NMR (400 MHz, d6-DMSO) δ 2.81 (s, 3H), 2.84 (s, 3H), 4.25 (s, 3H), 4.39 (s, 2H), 6.80 (d, J = 7.2 Hz, 1H), 7.11 (d, J = 7.2 Hz, 1H), 7.21 (m, 1H), 7.40 (s, 1H), 7.50 (m, 1H), 9.75 (s, 1H), 10.80 (br s, 1H). | m/z 328.4 [M + H]⁺ |
| 1527 | (structure) | 327.4 | ¹H NMR (400 MHz, d6-DMSO) δ 2.80 (s, 6H), 4.37 (s, 2H), 4.42 (s, 2H), 6.20 (s, 1H), 6.80 (s, 1H), 7.07 (s, 1H), 7.21 (m, 2H), 7.41 (m, 1H), 7.65 (m, 1H), 9.64 (s, 1H), 10.6 (br s, 1H). | m/z 328.3 [M + H]⁺ |
| 1531 | (structure) | 296.1 | ¹H NMR (400 MHz, d6-DMSO) δ 2.81 (s, 3H), 3.40 (s, 3H, obscured by solvent), 4.60 (s, 2H), 6.19 (s, 1H), 6.75 (m, 1H), 6.83 (m, 1H), 6.96 (m, 1H), 7.15 (m, 1H), 7.83 (m, 2H), 8.83 (s, 1H) | m/z 297.3 [M + H]⁺ |
| 1604 | (structure) | 253.7 | ¹H NMR (500 MHz, d6-DMSO) δ 2.30 (s, 3H), 2.48 (s, 3H), 3.52 (s, 2H), 6.43 (s, 1H), 7.17 (s, 1H), 8.38 (s, 1H). | m/z 254.0 [M + H]⁺ |

TABLE 6-continued
Compounds prepared according to Example 6 (Scheme 6)
| Compound | Structure | MW | ¹H NMR | MS |
|---|---|---|---|---|
| 1608 | 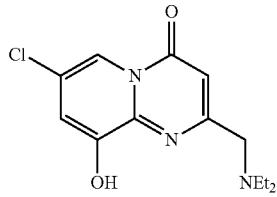 | 281.7 | ¹H NMR (500 MHz, d6-DMSO) δ 1.14 (t, J = 7.5 Hz, 3H), 2.90 (q, J = 7.5 Hz, 2H), 4.63 (s, 2H), 6.34 (s, 1H), 6.45 (d, J = 2.5 Hz, 1H), 7.86 (d, J = 2.5 Hz, 1H). | m/z 282.1 [M + H]⁺ |
| 1609 | 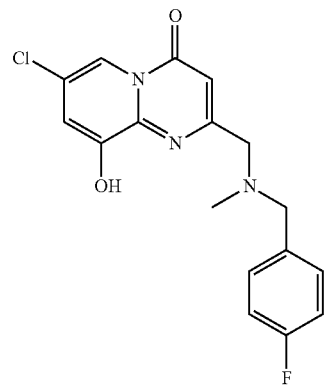 [SMILES: CN(Cc1ccc(F)cc1)Cc1cc(=O)n2cc(Cl)cc(O)c2n1] | 347.7 | ¹H NMR (500 MHz, d6-DMSO) δ 2.38 (s, 3H), 3.87 (s, 2H), 4.64 (s, 2H), 6.41 (s, 1H), 6.75 (s, 1H), 7.18 (app t, J = 9.0 Hz, 2H), 7.42 (m, 2H), 8.05 (s, 1H | m/z 348.1 [M + H]⁺ |
| 1610 | 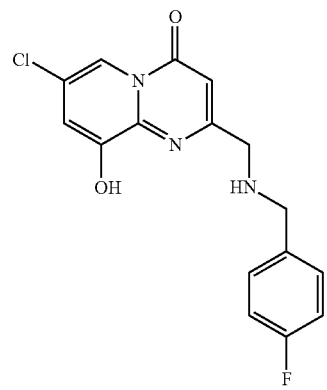 [SMILES: O=c1cc(CNCc2ccc(F)cc2)nc2c(O)cc(Cl)cn12] | 333.7 | ¹H NMR (500 MHz, d6-DMSO) δ 3.96 (s, 2H), 4.62 (s, 2H), 6.36 (s, 1H), 6.54 (d, J = 2.5 Hz, 1H), 7.19 (dd, J = 7.0, 2.5 Hz, 2H), 7.45 (m, 2H), 7.93 (d, J = 2.5 Hz, 1H). | m/z 334.0 [M + H]⁺ |
| 1612 | 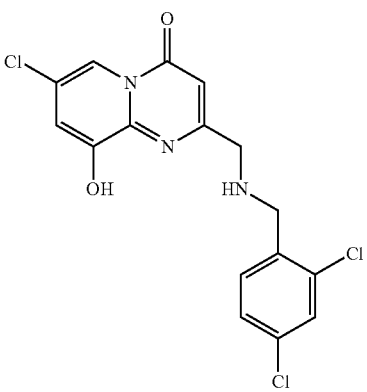 [SMILES: O=c1cc(CNCc2ccc(Cl)cc2Cl)nc2c(O)cc(Cl)cn12] | 384.6 | ¹H NMR (500 MHz, d6-DMSO) δ 3.94 (s, 2H), 4.64 (s, 2H), 6.45 (s, 1H), 6.82 (d, J = 2.0 Hz, 1H), 7.47 (dd, J = 9.5, 2.0 Hz, 1H), 7.19 (dd, J = 7.0, 2.5 Hz, 2H), 7.45 (m, 2H), 8.13 (d, J = 2.5 Hz, 1H). | m/z 386.9 [M + H]⁺ |

TABLE 6-continued

Compounds prepared according to Example 6 (Scheme 6)

| Compound | Structure | MW | ¹H NMR | MS |
|---|---|---|---|---|
| 1614 | 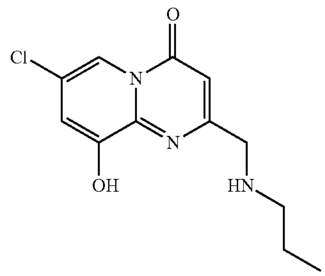 [SMILES: CCCNCc1cc(=O)n2cc(Cl)cc(O)c2n1] | 267.7 | ¹H NMR (500 MHz, d6-DMSO) δ 1.05 (d, J = 7.5 Hz, 3H), 1.81 (q, J = 7.5 Hz, 2H), 3.04 (t, J = 7.5 Hz, 2H), 4.23 (s, 2H), 6.32 (s, 1H), 8.80 (d, J = 2.5 1H), 8.17 (d, J = 2.5 Hz, 1H) | m/z 268.1 [M + H]⁺ |
| 1618 | 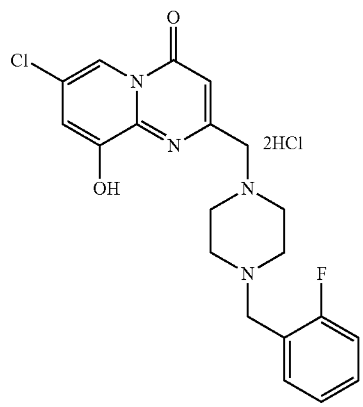 [SMILES: O=c1cc(CN2CCN(Cc3ccccc3F)CC2)nc2c(O)cc(Cl)cn12] | 402.9 | ¹H NMR (500 MHz, d6-DMSO) δ 3.52 (m, 4H), 4.19 (m, 2H), 4.43 (m, 2H), 6.62 (s, 1H), 7.28 (app t, J = 9.5 Hz, 1H), 7.33 (app t, J = 8.0 Hz, 1H), 7.44 (d, J = 2.0 Hz, 1H), 7.65 (m, 1H), 7.62 (app t, J = 8.0 Hz, 1H), 8.67 (d, J = 2.0 Hz, 1H) | m/z 403.1 [M + H]⁺ |
| 1634 | 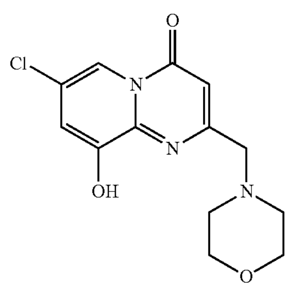 [SMILES: O=c1cc(CN2CCOCC2)nc2c(O)cc(Cl)cn12] | 295.7 | ¹H NMR (500 MHz, d6-DMSO) δ 3.35 (br m, 8H), 4.46 (s, 2H), 6.53 (s, 1H), 7.42 (d, J = 2.5 Hz, 1H), 8.46 (d, J = 2.5 Hz, 1H), 10.78 (br s, 1H), 10.85 (br s, 1H). | m/z 296.1 [M + H]⁺ |
| 1635 | 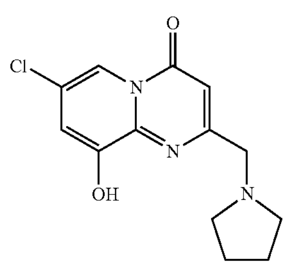 [SMILES: O=c1cc(CN2CCCC2)nc2c(O)cc(Cl)cn12] | 279.7 | ₁H NMR (500 MHz, d6-DMSO) δ 2.01 (d, J = 6.5 Hz, 4H), 3.07 (br s, 2H), 3.59 (br s, 2H), 4.46 (s, 2H), 6.50 (s, 1H), 7.45 (d, J = 2.0 Hz, 1H), 8.47 (d, J = 2.0 Hz, 1H), 10.73 (br s, 1H), 10.84 (br s, 1H). | m/z 280.1 [M + H]⁺ |

TABLE 6-continued

Compounds prepared according to Example 6 (Scheme 6)

| Compound | Structure | MW | ¹H NMR | MS |
|---|---|---|---|---|
| 1636 | 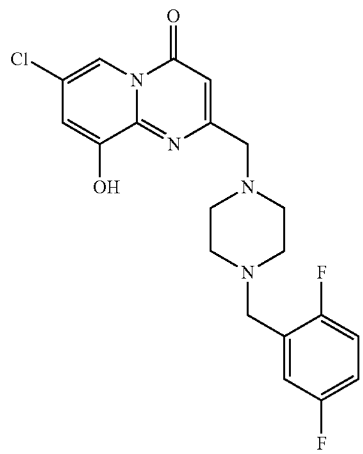 [SMILES: O=c1cc(CN2CCN(Cc3cc(F)ccc3F)CC2)nc2c(O)cc(Cl)cn12] | 420.8 | ¹H NMR (500 MHz, d6-DMSO) δ 3.49 (m, 4H), 4.15 (m, H), 4.47 (s, 2H), 6.54 (s, 1H), 7.34 (m, 2H), 7.44 (s, 1H), 7.55 (s, 1H), 8.46 (s, 1H), 10.70 (br s, 1H). | m/z 421.1 [M + H]⁺ |
| 1637 | 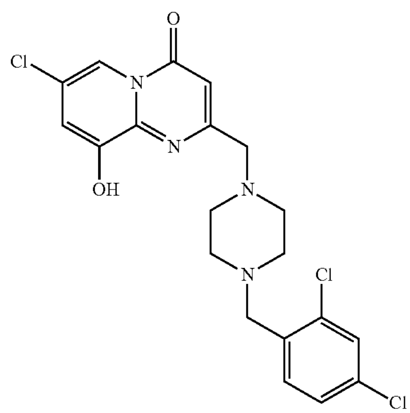 [SMILES: O=c1cc(CN2CCN(Cc3ccc(Cl)cc3Cl)CC2)nc2c(O)cc(Cl)cn12] | 453.8 | ¹H NMR (500 MHz, d6-DMSO) δ 2.68 (br s, 4H), 3.14 (br s, 4H), 3.67 (s, 2H), 4.63 (s, 2H), 6.55 (s, 1H), 6.88 (s, 1H), 7.33 (d, J = 6.5 Hz, 1H), 7.45 (m, 2H), 8.26 (s, 1H) | m/z 453.1 [M + H]⁺ |
| 1638 | 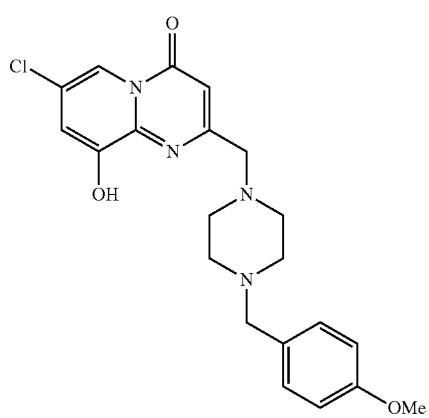 [SMILES: COc1ccc(CN2CCN(Cc3cc(=O)n4cc(Cl)cc(O)c4n3)CC2)cc1] | 414.9 | ¹H NMR (500 MHz, MeOD) δ 2.45 (m, 4H), 2.95 (m, 4H), 3.41 (s, 2H), 3.62 (s, 3H), 4.64 (s, 2H), 6.37 (s, 1H), 6.59 (d, J = 2.0 Hz, 1H), 6.87 (d, J = 8.5 Hz, 2H), 7.19 (d, J = 8.5 Hz, 2H), 7.95 (d, J = 2.0 Hz, 1H). | m/z 415.2 [M + H]⁺ |
| 1670 | 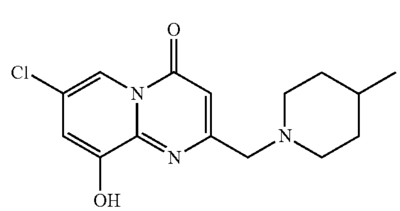 [SMILES: CC1CCN(Cc2cc(=O)n3cc(Cl)cc(O)c3n2)CC1] | 307.8 | ¹H NMR (500 MHz, d6 DMSO) δ 0.932 (m, 4H), 1.59 (m, 2H), 1.79 (m, 2H), 3.01 (m, 2H), 3.48 (m, 2H), 4.36 (s, 2H), 6.54 (s, 1H), 7.44 (s, 1H), 8.47 (s, 1H) | m/z 308.2 [M + H]⁺ |

TABLE 6-continued

Compounds prepared according to Example 6 (Scheme 6)

| Compound | Structure | MW | $^1$H NMR | MS |
|---|---|---|---|---|
| 1699 | 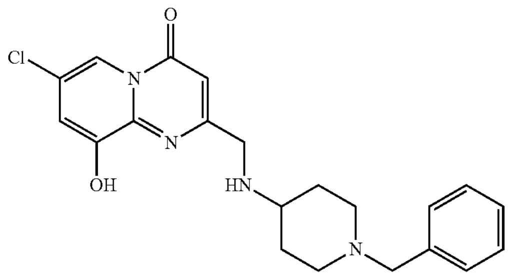 [SMILES: O=c1cc(CNC2CCN(Cc3ccccc3)CC2)nc2c(O)cc(Cl)cn12] | 398.9 | $^1$H NMR (400 MHz, d6-DMSO) δ 1.49 (m, 2H), 1.83 (m, 2H), 1.91 (m, 2H), 2.75 (m, 2H), 2.91 (m, 1H), 3.40 (s, 2H), 4.60 (s, 2H), 6.28 (s, 1H), 6.38 (d, J = 1.6 Hz, 1H), 7.23 (m, 5H), 7.80 (d, J = 1.6 Hz, 1H) | No molecular ion observed |
| 1707 | 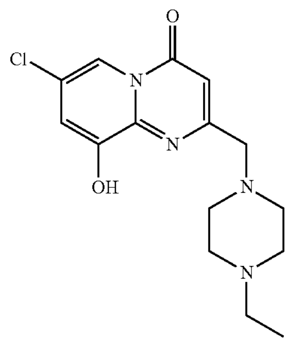 [SMILES: CCN1CCN(Cc2cc(=O)n3cc(Cl)cc(O)c3n2)CC1] | 322.8 | $^1$H NMR (400 MHz, d6-CDCl$_3$) δ 1.12 (m, J = 7.6 Hz, 3H), 2.47 (q, J = 7.6 Hz, 2H), 2.49 (m, 4H), 2.66 (m, 4H), 3.58 (s, 2H), 6.61 (s, 1H), 7.13 (d, J = 2.0 Hz, 1H), 8.56 (d, J = 2.0 Hz, 1H) | m/z 323.1 [M + H]$^+$ |

Example 7

7 and 8-Substituted alkynyl or ethyl pyrido-pyrimidinones 7-1 and 7-3 can be prepared from ethynyl intermediate 4-3, shown in Scheme 7. Removal of the isopropoxy ether with conc. HBr or boron trichloride generates target compound 7-1. Alternatively 4-3 can undergo reduction by the action of sodium borohydride in the presence of Palladium on Carbon to generate ethyl derivative 7-2. Protective group removal as for 4-3 yields target compound 7-3 (Scheme 7).

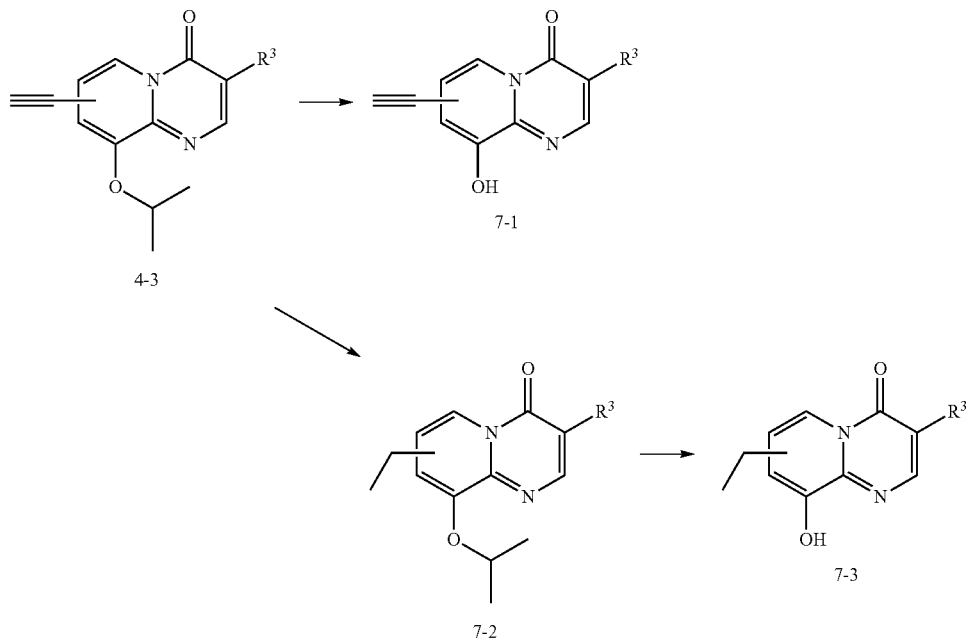

Scheme 7 in which R$^3$ is propyl.

Compound 1620

7-Ethynyl-9-hydroxy-3-propyl-4H-pyrido[1,2-a]pyrimidin-4-one (7-1)

7-Ethynyl-9-isopropoxy-3-propyl-4H-pyrido[1,2-a]pyrimidin-4-one 4-3 (150 mg, 0.55 mmol) was dissolved in anhydrous $CH_2Cl_2$ and cooled to 0° C. Boron trichloride (0.85 mL, 0.85 mmol, 1.0M solution in $CH_2Cl_2$) was added dropwise to the solution. The reaction was allowed to warm to rt for 3 h. The reaction was quenched with sat. aq. $NaHCO_3$ and the aqueous layer was extracted with $CH_2Cl_2$ (×3). The combined organic layers were washed with brine, dried over $Na_2SO_4$, filtered and concentrated to give a light yellow solid. The solid was dissolved in MeOH (10 mL) and concentrated on a rotary evaporator. The process was repeated three times. The resulting residue was then recrystallized from hot ethanol to afford 7-ethynyl-9-hydroxy-3-propyl-4H-pyrido[1,2-a]pyrimidin-4-one 7-1 as a white fluffy solid (32 mg, 25%). $^1$H NMR (500 MHz, d6-DMSO) δ0.90 (t, J=7.5 Hz, 3H), 1.59 (sext, J=7.5 Hz, 2H), 2.54 (t, J=7.5 Hz, 2H), 4.58 (s, 1H), 7.45 (s, 1H), 8.20 (s, 1H), 8.58 (d, J=1.5 Hz, 1H). HPLC: $t_R$=9.31 min (99%). MS: m/z 229.0 $[M+H]^+$.

7-Ethyl-9-isopropoxy-3-propyl-4H-pyrido[1,2-a]pyrimidin-4-one (7-2)

7-Ethynyl-9-isopropoxy-3-propyl-4H-pyrido[1,2-a]pyrimidin-4-one 4-3 (135 mg, 0.5 mmol) was dissolved in isopropanol (5 Ml) to which was then added AcOH (57 µL, 1.0 mmol) and 10% Pd/C (14 mg). To the mixture was added $NaBH_4$ (76 mg, 2.0 mmol) with effervescence observed and the reaction was stirred for 30 minutes. A further 38 mg of $NaBH_4$ was added and the reaction was allowed to stir for 30 minutes. The reaction was then quenched with 0.1M HCl until effervescence ceased. Sat. aq $NaHCO_3$ was added until slightly basic and the mixture was then filtered through a pad of celite washing with $CH_2Cl_2$. The aqueous layer was extracted into $CH_2Cl_2$ (×3). The combined extracts were dried over $Na_2SO_4$, filtered and concentrated to give the ethyl derivative 7-2 as light brown oil (130 mg, 95%). $^1$H NMR (500 MHz, d6-DMSO) δ0.98 (t, J=7.5 Hz, 3H), 1.32 (t, J=7.5 Hz, 3H), 1.52 (d, J=6.0 Hz, 6H), 1.69 (sext, J=7.5 Hz, 2H), 2.63 (t, J=7.5 Hz, 2H), 2.71 (dq, J=7.5, 1.0 Hz, 2H), 4.76 (sept, J=6.0 Hz, 1H), 6.83 (d, J=1.5 Hz, 1H), 8.25 (s, 1H), 8.52 (dt, J=1.5, 1.0 Hz, 1H).

7-Ethyl-9-hydroxy-3-propyl-4H-pyrido[1,2-a]pyrimidin-4-one (7-3) (1620)

7-Ethyl-9-isopropoxy-3-propyl-4H-pyrido[1,2-a]pyrimidin-4-one (7-2) (128 mg, 0.47 mmol) was dissolved in 48% HBr (3 mL) and then heated to reflux for 1 h. After cooling the reaction was basified with sat. aq $NaHCO_3$ and the aqueous layer was extracted into $CH_2Cl_2$ (×3). The combined organic layers were washed with brine, dried over $Na_2SO_4$, filtered and concentrated to provide 7-ethyl-9-hydroxy-3-propyl-4H-pyrido[1,2-a]pyrimidin-4-one 7-3 (101 mg, 93%) as a light green powder. $^1$H NMR (500 MHz, d6-DMSO) δ1.00 (t, J=7.5 Hz, 3H), 1.31 (t, J=7.5 Hz, 3H), 1.70 (sext, J=7.5 Hz, 2H), 2.64 (t, J=7.5 Hz, 2H), 2.71 (q, J=7.5 Hz, 2H), 7.02 (d, J=1.5 Hz, 1H), 8.10 (s, 1H), 8.40 (d, J=1.5 Hz, 1H). HPLC; $t_R$=8.80 min (98.1%). MS: m/z 233.0 $[M+H]^+$.

TABLE 7

Compounds prepared according to Example 7 (Scheme 7)

| Compound | Structure | MW | NMR | MS |
|---|---|---|---|---|
| 1613 | 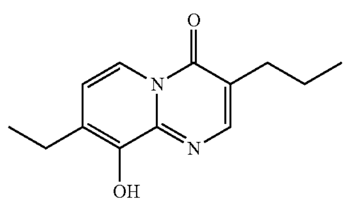 [SMILES: CCCc1cnc2c(O)c(CC)ccn2c1=O] | 232.3 | $^1$H NMR (500 MHz, d6-DMSO) δ 0.90 (t, J = 7.5 Hz, 3H), 1.18 (t, J = 7.5 Hz, 3H), 1.61 (m, 2H), 2.51 (m, 2H) 3.04 (t, J = 7.5 Hz, 2H), 7.19 (d, J = 7.0 Hz, 1H0, 8.21 (s, 1H), 8.44 (d, J = 7.0 Hz, 1H) | m/z 233.1 $[M + H]^+$ |
| 1619 | 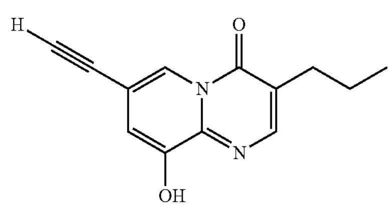 [SMILES: C#Cc1cc(O)c2ncc(CCC)c(=O)n2c1] | 228.3 | $^1$H NMR (500 MHz, d6-DMSO) δ 0.90 (t, J = 7.5 Hz, 3H), 1.59 (sext, J = 7.5 Hz, 2H), 2.54 (t, J = 7.5 Hz, 2H), 4.58 (s, 1H), 7.45 (s, 1H), 8.20 (s, 1H), 8.58 (d, J = 1.5 Hz, 1H) | m/z 229.1 $[M + H]^+$ |
| 1620 | 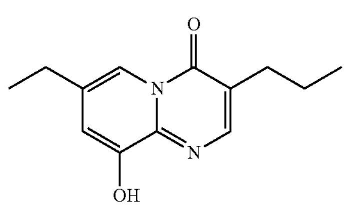 [SMILES: CCCc1cnc2c(O)cc(CC)cn2c1=O] | 232.3 | $^1$H (500 MHz, CDCl$_3$) δ 1.00 (t, J = 7.5 Hz, 3H), 1.31 (t, J = 7.5 Hz, 3H), 1.70 (sext, J = 7.5 Hz, 2H), 2.64 (t, J = 7.5 Hz, 2H), 2.71 (q, J = 7.5 Hz, 2H), 7.02 (d, J = 1.5 Hz, 1H), 8.10 (s, 1H), 8.40 (d, J = 1.5 Hz, 1H) | m/z 233.09 $[M + H]^+$ |

TABLE 7-continued

Compounds prepared according to Example 7 (Scheme 7)

| Compound | Structure | MW | NMR | MS |
|---|---|---|---|---|
| 1625 | 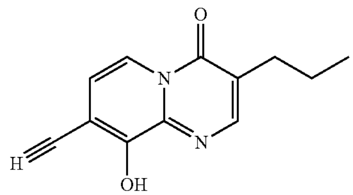 | 228.3 | $^1$H NMR (500 MHz, d6-DMSO) δ 0.92 (t, J = 7.0 Hz, 3H), 1.61 (m, 2H), 2.52 (m, 2H), 1.86 (m, 2H), 4.79 (s, 1H), 7.17 (d, J = 7.5 Hz, 1H), 8.24 (s, 1H), 8.34 (d, J = 7.5 Hz) | m/z 229.1 [M + H]$^+$ |

Example 8

8-Substituted aminomethyl carboxamide derivatives 8-1 can be prepared analogously to those aminomethyl compounds 3-1 synthesized in Scheme 3. The carboxamide 5-1 is heated with a commercially available aminal to provide target compounds 8-1 (Scheme 8).

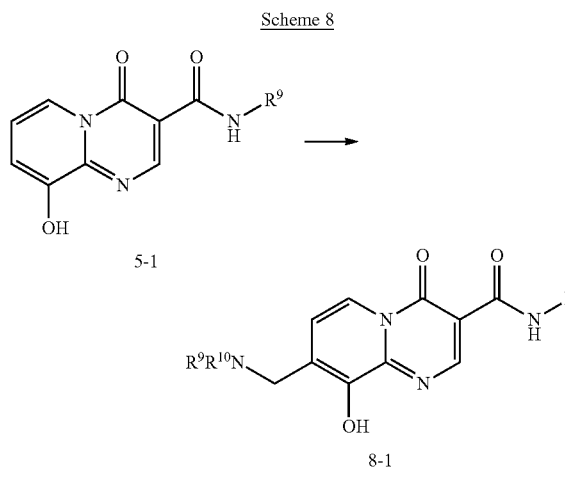

Scheme 8 in which $R^9$ and $R^{10}$ are independently selected from $C_{5-6}$cycloalkyl, $CH_2$ optionally substituted phenyl, $C_{1-4}$alkyl and phenyl fused with a 5 membered O containing heterocyclyl.

Compound 1628

N-cyclohexyl-8-((dimethylamino)methyl)-9-hydroxy-4-oxo-4H-pyrido[1,2-a]pyrimidine-3-carboxamide (8-1)(1628)

N-cyclohexyl-9-hydroxy-4-oxo-4H-pyrido[1,2-a]pyrimidine-3-carboxamide (181 mg, 0.63 mmol) was dissolved in toluene (6 mL) then heated with N,N,N,N-tetramethylmethylenediamine (500 µL, 3.67 mmol) at 85° C. for 3 h. The resulting yellow precipitate was collected, after cooling, by filtration. The crude product was washed with toluene to afford the carboxamide 8-1 as yellow solid (173 mg, 80%). $^1$H NMR (500 MHz, d6-DMSO) δ1.37 (m, 5H), 1.39 (m, 1H), 1.66 (m, 2H), 1.87 (m, 2H), 2.35 (s, 6H), 3.72 (s, 2H), 3.86 (m, 1H), 7.45 (d, J=7.0 Hz, 1H), 8.61 (d, J=7.0 Hz, 1H), 8.97 (s, 1H), 9.04 (d, J=8.0 Hz, 1H). HPLC: $t_R$=8.60 min (97.8%). MS: m/z 345.2[M+H]$^+$.

TABLE 8

Compounds prepared according to Example 8 (Scheme 8)

| Compound | Structure | MW | $^1$H NMR | MS |
|---|---|---|---|---|
| 1628 | 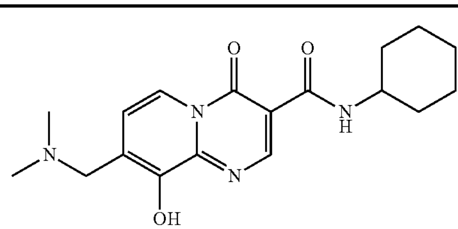 | 344.4 | $^1$H NMR (500 MHz, d6-DMSO) δ 1.37 (m, 5H), 1.39 (m, 1H), 1.66 (m, 2H), 1.87 (m, 2H), 2.35 (s, 6H), 3.72 (s, 2H), 3.86 (m, 1H), 7.45 (d, J = 7.0 Hz, 1H), 8.61 (d, J = 7.0 Hz, 1H), 8.97 (s, 1H), 9.04 (d, J = 8.0 Hz, 1H). | m/z 345.2 [M + H]$^+$ |
| 1644 | 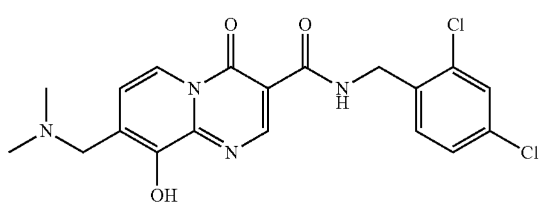 [SMILES: CN(C)Cc1ccn2c(=O)c(C(=O)NCc3ccc(Cl)cc3Cl)cnc2c1O] | 421.3 | $^1$H NMR (400 MHz, d6-DMSO) δ 2.31 (s, 6H), 3.74 (s, 2H), 4.61 (d, J = 6.0 Hz, 2H), 7.41 (s, 2H), 7.47 (d, J = 7.5 Hz, 1H), 7.63 (s, 1H), 8.63 (d, J = 7.5 Hz, 1H), 8.97 (s, 1H), 9.50 (t, J = 6.0 Hz, 1H). | m/z 421.1 [M + H]$^+$ |

TABLE 8-continued

Compounds prepared according to Example 8 (Scheme 8)

| Compound | Structure | MW | ¹H NMR | MS |
|---|---|---|---|---|
| 1658 | 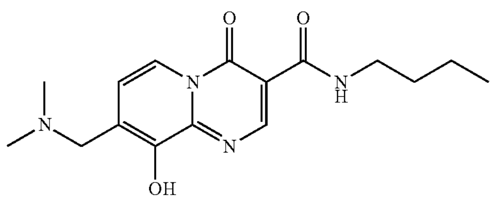 [SMILES: CCCCNC(=O)c1cnc2c(O)c(CN(C)C)ccn2c1=O] | 318.4 | ¹H NMR (400 MHz, d6-DMSO) δ 0.93 (t, J = 7.6 Hz, 3H), 1.37 (sext, J = 7.6 Hz, 2H), 1.51 (quin, J = 7.6 Hz, 2H), 3.37 (ABq, J = 5.6 Hz, 2H), 3.73 (s, 2H), 7.45 (d, J = 6.8 Hz, 1H), 8.61 (d, J = 6.8 Hz, 1H), 8.97 (s, 1H), 9.02 (t, J = 5.6 Hz, 1 Hz). | m/z 319.1 [M + H]⁺ |
| 1664 | 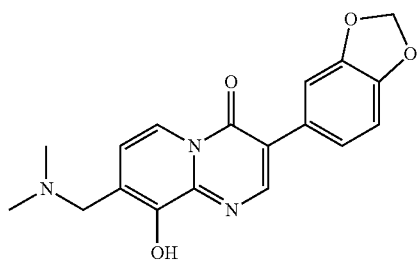 [SMILES: CN(C)Cc1ccn2c(=O)c(-c3ccc4c(c3)OCO4)cnc2c1O] | 339.4 | ¹H NMR (500 MHz, d6-DMSO) δ 2.26 (s, 6H), 3.63 (s, 2H), 6.04 (s, 2H), 6.99 (d, J = 8.5 Hz, 1H), 7.31 (m, 2H), 7.42 (s, 1H), 8.51 (s, 1H), 8.57 (d, J = 1.5, 7.0 Hz, 1H) | m/z 340.1 [M + H]⁺ |
| 1669 | 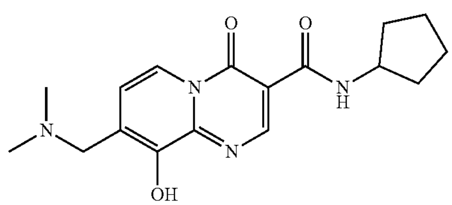 [SMILES: CN(C)Cc1ccn2c(=O)c(C(=O)NC3CCCC3)cnc2c1O] | 330.4 | ¹H NMR (500 MHz, d6-DMSO) δ 1.47 (m, 2H), 1.63 (m, 2H), 1.67 (m, 2H), 1.91 (m, 2H), 2.30 (s, 6H), 3.72 (s, 2H), 4.25 (sext, J = 7.0 Hz, 1H), 7.45 (d, J = 7.0 Hz, 1H), 8.59 (d, J = 7.0 Hz, 1H), 8.96 (s, 1H), 9.03 (d, J = 7.5 Hz, 1H) | m/z 331.1 [M + H]⁺ |
| 1682 | 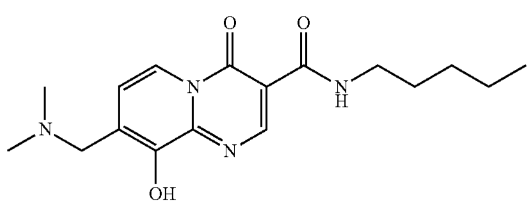 [SMILES: CCCCCNC(=O)c1cnc2c(O)c(CN(C)C)ccn2c1=O] | 332.4 | ¹H NMR (400 MHz, d6-DMSO) δ 0.87 (t, J = 6.8 Hz, 3H), 1.32 (m, 4H), 1.53 (t, J = 6.8 Hz, 2H), 2.23 (s, 6H), 3.33 (q, J = 6.4 Hz, 2H), 3.71 (s, 2H), 7.45 (d, J = 6.8 Hz, 1H), 8.61 (d, J = 6.8 Hz, 1H), 8.97 (s, 1H), 9.02 (t, J = 5.6 Hz, 1H). | m/z 333.2 [M + H]⁺ |
| 1710 | 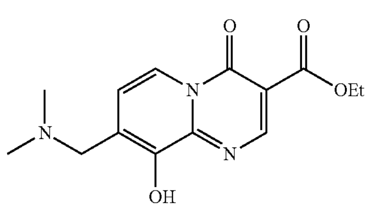 [SMILES: CCOC(=O)c1cnc2c(O)c(CN(C)C)ccn2c1=O] | 291.3 | ¹H NMR (500 MHz, CDCl₃) δ 1.27 (t, J = 7.0 Hz, 3H), 2.45 (s, 6H), 3.83 (s, 2H), 4.43 (q, J = 7.0 Hz, 2H), 7.04 (d, J = 7.0 Hz, 1H), 8.79 (d, J = 7.0 Hz, 1H), 9.05 (s, 1H). | m/z 292.1 [M + H]⁺ |
| 1712 | 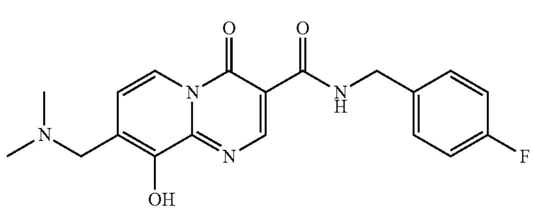 [SMILES: CN(C)Cc1ccn2c(=O)c(C(=O)NCc3ccc(F)cc3)cnc2c1O] | 370.4 | ¹H NMR (400 MHz, CDCl₃) δ 2.44 (s, 6H), 3.83 (s, 2H), 4.65 (d, J = 6.0 Hz, 2H), 7.02 (app t, J = 8.4 Hz, 2H), 7.08 (d, J = 7.6 Hz, 1H), 7.35 (m, 2H), 8.69 (d, J = 7.6 Hz, 1H), 9.36 (s, 1H), 3.93 (br t, J = 6.0 Hz, 1H). | m/z 371.2 [M + H]⁺ |

Example 9a

8 Substituted aryl and heteroaryl 3-carboxamide derivatives can be prepared according to Scheme 9a. Carboxamide 9-1 can be ortho iodinated to give intermediate 9-2 which is then protected to afford compound 9-3. Suzuki coupling conditions are then employed to produce aryl or heteroaryl compounds 9-4. Finally, deprotection affords the target compounds 9-5.

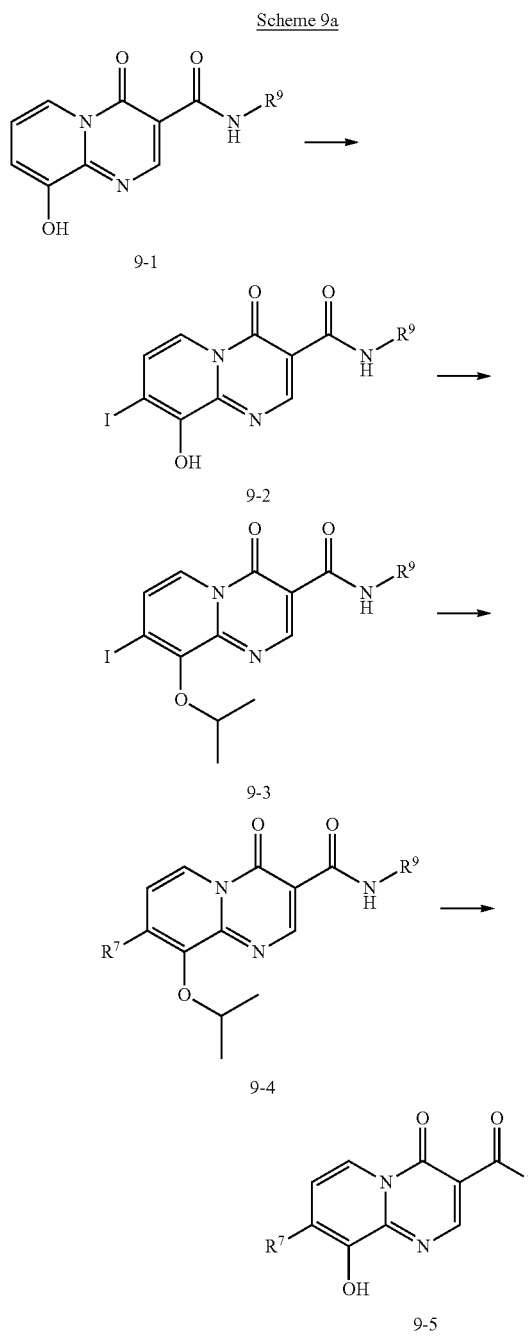

Scheme 9a in which $R^7$ is optionally substituted 5 membered N-containing heterocyclyl or optionally substituted phenyl; $R^9$ is butyl.

PB1657

N-butyl-9-hydroxy-8-iodo-4-oxo-4H-pyrido[1,2-a]pyrimidine-3-carboxamide 9-2

To a solution of N-butyl-9-hydroxy-4-oxo-4H-pyrido[1,2-a]pyrimidine-3-carboxamide (80 mg, 0.31 mmol) in EtOH (5 mL) was added iodine (90 mg, 0.34 mmol) followed by 30% aqueous hydrogen peroxide (34 μL). The reaction was allowed to stir at rt for 3 days at which time N-butyl-9-hydroxy-8-iodo-4-oxo-4H-pyrido[1,2-a]pyrimidine-3-carboxamide 9-2 had precipitated out of solution and was collected by filtration (71 mg, 60% yield). $^1$H NMR (400 MHz, d6-DMSO) δ0.91 (t, J=7.0 Hz, 3H), 1.35 (m, 2H), 1.49 (m, 2H), 3.2 (m, 2H, obscured), 7.81 (d, J=8.0 Hz, 1H), 8.40 (d, J=8.0 Hz, 1H), 8.96 (br s, 1H), 8.98 (s, 1H).

N-butyl-9-isopropxy-8-iodo-4-oxo-4H-pyrido[1,2-a]pyrimidine-3-carboxamide 9-3

N-butyl-9-hydroxy-8-iodo-4-oxo-4H-pyrido[1,2-a]pyrimidine-3-carboxamide 9-2 (1.49 g, 38.5 mmol) was dissolved in DMF (50 mL) and treated with $K_2CO_3$ (2.12 g, 154 mmol) followed by 2-bromopropane (5 mL). The reaction was heated to 50° C. for 17 h, cooled and concentrated to dryness. The residue was taken up in EtOAc and $H_2O$ and the aqueous layer was extracted into EtOAc (×2). The combined organic layers were washed with $H_2O$, brine, dried over $Na_2SO_4$, filtered and concentrated to provide N-butyl-9-isopropxy-8-iodo-4-oxo-4H-pyrido[1,2-a]pyrimidine-3-carboxamide 9-3 (1.41 g, 85% yield). $^1$H NMR (400 MHz, CDCl$_3$) δ0.98 (t, J=7.6 Hz, 3H), 1.44 (m, 9H), 1.62 (m, 2H), 3.49 (m, 2H), 5.44 (m, 1H), 7.63 (d, J=7.6 Hz, 1H), 8.63 (d, J=7.6 Hz, 1H), 8.95 (br s, 1H), 9.28 (s, 1H).

N-butyl-8-(3,5-di methyl isoxazol-4-yl)-9-isopropoxy-4-oxo-4H-pyrido[1,2-a]pyrimidine-3-carboxamide (9-4)

A solution of N-butyl-9-isopropxy-8-iodo-4-oxo-4H-pyrido[1,2-a]pyrimidine-3-carboxamide 9-3 (235 mg, 0.607 mmol), $K_2CO_3$ (1.21 mL, 2.42 mmol, 2M aqueous solution), 3,5-dimethylisoxazole pinacol ester (176 mg, 0.789 mmol), Pd(PPh$_3$)$_4$ (59 mg, 0.051 mmol) in anhydrous DMF (10 mL) were degassed under argon (×3) then heated to 100° C. for 4 h. After cooling, the reaction was diluted with $H_2O$ (20 mL)/EtOAc (30 mL). The aqueous layer was extracted into EtOAc (×2). The combined organic layers were washed with $H_2O$, brine, dried over $Na_2SO_4$, filtered, concentrated and purified by flash chromatography eluting with 30 to 40% EtOAc/hexane to provide N-butyl-8-(3,5-dimethylisoxazol-4-yl)-9-isopropoxy-4-oxo-4H-pyrido[1,2-a]pyrimidine-3-carboxamide 9-4 (119 mg, 54%) as an off-white solid. $^1$H NMR (400 MHz, d6-DMSO), 0.97 (t, J=7.2 Hz, 3H), 1.21 (d, J=6.4 Hz, 6H), 1.44 (sext, J=7.2 Hz, 2H), 1.66 (quin, J=7.2 Hz, 2H), (2.30 (s, 3H), 2.43 (s, 3H), (3.50 (q, J=7.2 Hz, 6.0 Hz, 2H), 4.94 (sept, J=6.0 Hz, 1H), 7.15 (d, J=7.2 Hz, 1H), 8.97 (br t, J=6.0 Hz, 1H), 9.01 (d, J=7.2 Hz, 1H), 9.38 (s, 1H).

N-butyl-8-(3,5-dimethylisoxazol-4-yl)-9-hydroxy-4-oxo-4H-pyrido[1,2-a]pyrimidine-3-carboxamide (9-5) (PB1657)

N-butyl-8-(3,5-dimethylisoxazol-4-yl)-9-isopropoxy-4-oxo-4H-pyrido[1,2-a]pyrimidine-3-carboxamide (9-4) (110 mg, 0.276 mmol) was heated to reflux in 48% aq HBr (3 mL) for 2 h. The reaction was cooled then quenched with saturated aqueous NaHCO$_3$ solution. The compound was extracted into CH$_2$Cl$_2$ (×3) and concentrated to afford N-butyl-8-(3,5-dimethylisoxazol-4-yl)-9-hydroxy-4-oxo-4H-pyrido[1,2-a]pyrimidine-3-carboxamide (9-5) (PB1657). $^1$H NMR (400 MHz, CDCl$_3$) δ 0.93 (t, J=7.6 Hz, 3H), 1.37 (sext, J=7.6 Hz, 2H), 1.51 (quin, J=7.6 Hz, 2H), 3.37 (q, J=6.8 Hz, 2H), 7.49 (d, J=6.8 Hz, 1H), 8.69 (d, J=6.8 Hz, 1H), 8.90 (t, J=6.8 Hz, 1H), 9.03 (s, 1H). Mass Spec: m/z 357.1187[M+H]$^+$.

Scheme 9b

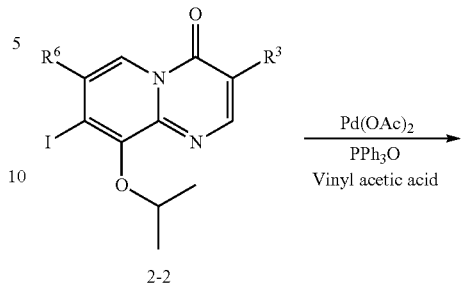

TABLE 9a

Compounds prepared according to Example 9a (Scheme 9a)

| Compound | Structure | MW | NMR | MS |
|---|---|---|---|---|
| 1657 | 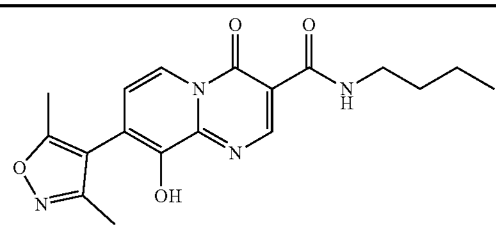 | 356.4 | $^1$H NMR (400 MHz, d6-DMSO) δ 0.93 (t, J = 7.6 Hz, 3H), 1.37 (sext, J = 7.6 Hz, 2H), 1.51 (quin, J = 7.6 Hz, 2H), 3.37 (q, J = 6.8 Hz, 2H), 7.49 (d, J = 6.8 Hz, 1H), 8.69 (d, J = 6.8 Hz, 1H), 8.90 (t, J = 6.8 Hz, 1H), 9.03 (s, 1H). | m/z 357.1 [M + H]$^+$ |
| 1660.1 | 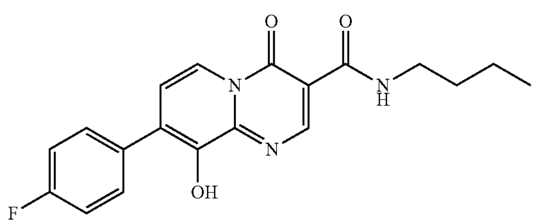 [SMILES: CCCCNC(=O)c1cnc2c(O)c(-c3ccc(F)cc3)ccn2c1=O] | 355.4 | $^1$H NMR (400 MHz, d6-DMSO) δ 0.91 (t, J = 7.6 Hz, 3H), 1.36 (m, 2H), 1.51 (m, 2H), 3.36 (m, 2H), 7.36 (m, 2H), 7.66 (d, J = 7.2 Hz, 1H), 7.90 (m, 2H), 8.70 (d, J = 7.2 Hz, 1H), 8.99 (m, 1H), 9.02 (s, 1H). | m/z 356.1 [M + H]$^+$ |
| 1661 | 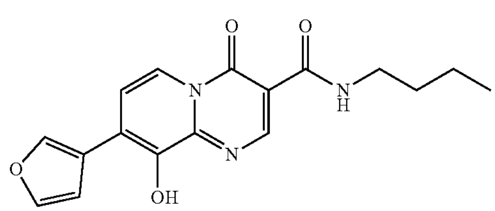 [SMILES: CCCCNC(=O)c1cnc2c(O)c(-c3ccoc3)ccn2c1=O] | 327.3 | $^1$H NMR (400 MHz, d6-DMSO) δ 0.91 (t, J = 7.0 Hz, 3H), 1.35 (m, 2H), 1.51 (m, 2H), 3.35 (m, 2H), 7.27 (m, 2H), 7.85 (d, J = 7.5 Hz, 1H), 7.89 (t, J = 2.0 Hz, 1H), 8.51 (s, 1H), 8.68 (d, J = 7.5 Hz, 1H), 8.98 (t, J = 6.0 Hz, 1H), 9.01 (s, 1H). | m/z 328.2 [M + H]$^+$ |

Example 9b

Compounds containing alkyl chains of three carbons or greater at position 9 can be prepared according to Scheme 9b. Attempted Heck coupling of compound 2-2 with vinyl acetic acid unexpectedly resulted in the formation of decarboxylated product 9-1. Selective reduction of the alkene afforded compound 9-2. Removal of the isopropyl ether using HBr generated target compound 9-3

-continued

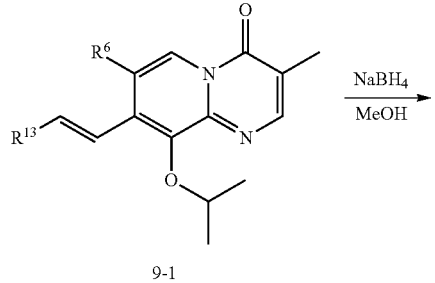

97

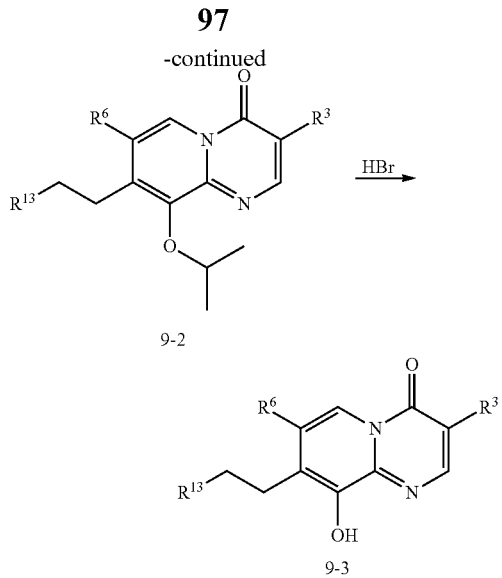

Compound 1605

9-Isopropoxy-3-isopropyl-8-(prop-1-enyl)-4H-pyrido[1,2-a]pyrimidin-4-one (9-1)

8-Iodo-9-isopropxy-3-isopropyl-4H-pyrido[1,2-a]pyrimidin-4-one 2-2 (195 mg, 0.524 mmol) was dissolved in anhydrous DMF (10 mL) and then degassed under argon (×3). Triphenylphosphine (14 mg, 0.053 mmol), Pd(OAc)$_2$ (35 mg, 0.0524 mmol) and vinyl acetic acid (1.0 mL, 11.5 mmol) were added followed by another round of degassing. The reaction was then heated to 100° C. for 4 h. The reaction was cooled and then partitioned between EtOAc/H$_2$O. The aqueous layer was extracted into EtOAc a further three times. Combined organic extracts were then dried over Na$_2$SO$_4$, filtered, concentrated and purified by flash chromatography eluting with 10% EtOAc/petroleum ether 40-60° C. to afford the 9-Isopropoxy-3-isopropyl-8-(prop-1-enyl)-4H-pyrido[1,2-a]pyrimidin-4-one 9-1 as a yellow oil (147 mg, 85%). $^1$H NMR (500 MHz, CDCl$_3$) δ1.30 (d, J=7.0 Hz, 1H), 1.36 (d, J=6.5 Hz, 1H), 2.01 (d, J=6.5 Hz, 3H), 3.24 (m, 1H), 5.05 (sept, J=6.5 Hz, 1H), 6.49 (dq, J=16.0, 6.5 Hz, 1H), 6.90 (dd, J=16.0, 1.5 Hz, 1H), 7.17 (d, J=7.5 Hz, 1H), 8.21 (s, 1H), 8.73 (d, J=7.5 Hz, 1H).

9-Isopropoxy-3-isopropyl-8-propyl-4H-pyrido[1,2-a]pyrimidin-4-one (9-2)

9-Isopropoxy-3-isoproply-8-(prop-1-enyl)-4H-pyrido[1,2-a]pyrimidin-4-one (9-1) (540 mg, 1.87 mmol) was dissolved in MeOH (20 Ml), cooled to 0° C. then treated with 5 lots of sodium borohydride (500 mg, 13.5 mmol) over 5 h. The reaction was left to stir for 2 days then concentrated. The residue was taken up in H$_2$O and CH$_2$Cl$_2$. The aqueous layer was then extracted into CH$_2$Cl$_2$ (×3) and the organic layer was dried over Na$_2$SO$_4$, filtered and concentrated to provide the major product, 9-Isopropoxy-3-isopropyl-8-propyl-4H-pyrido[1,2-a]pyrimidin-4-one (9-2) as an oil (410 mg, 75%). $^1$H NMR δ0.99 (t, J=7.0 Hz, 3H), 1.32 (d, J=6.5 Hz, 6H), 1.35 (d, J=6.5 Hz, 6H), 1.66 (m, 2H), 2.74 (t, J=7.0 Hz, 2H), 3.25 (sept, J=6.5 Hz, 1H), 5.13 (sept, J=6.5 Hz, 1H), 6.94 (d, J=7.5 Hz, 1H), 8.22 (s, 1H), 8.77 (d, J=7.5 Hz, 1H).

98

9-hydroxy-3-isopropyl-8-propyl-4H-pyrido[1,2-a]pyrimidin-4-one (9-3) (1605)

9-Isopropoxy-3-isopropyl-8-propyl-4H-pyrido[1,2-a]pyrimidin-4-one (9-2) (78 mg, 0.27 mmol) was heated to reflux in 48% aq HBr (2 mL) for 2 h. The reaction was cooled and concentrated and the resulting residue was diluted with H$_2$O. The mixture was then extracted into EtOAc (×3). The combined organic layers were washed with H$_2$O, dried over Na$_2$SO$_4$, filtered and concentrated to give a pale green solid. CH$_3$CN (5 mL) and H$_2$O (1 mL) were added to precipitate the target compound 9-3 as a flaky green solid (10 mg, 15%). $^1$H NMR (500 MHz, d6-DMSO) δ0.91 (t, J=7.5 Hz, 3H), 1.25 (d, J=6.5 Hz, 6H), 1.62 (sext, J=7.5 Hz, 2H), 2.66 (t, J=7.5 Hz, 2H), 3.11 (sept, J=6.5 Hz, 1H), 7.17 (d, J=7.0 Hz, 1H), 8.20 (s, 1H), 8.44 (d, J=7.0 Hz, 1H). HPLC: t$_R$=9.72 (98.25%). MS: m/z 247.1 [M+H]$^+$.

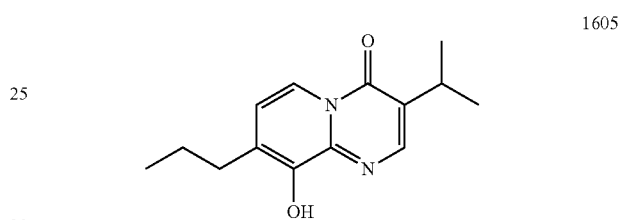

Example 10

Compounds possessing 2-substituted alkyloxymethyl groups can be prepared according to Scheme 10. The chloromethyl intermediate 6-1 is heated together with the appropriate alcohol in the presence of NaOH to form the desired ether product 10-1 (Scheme 10).

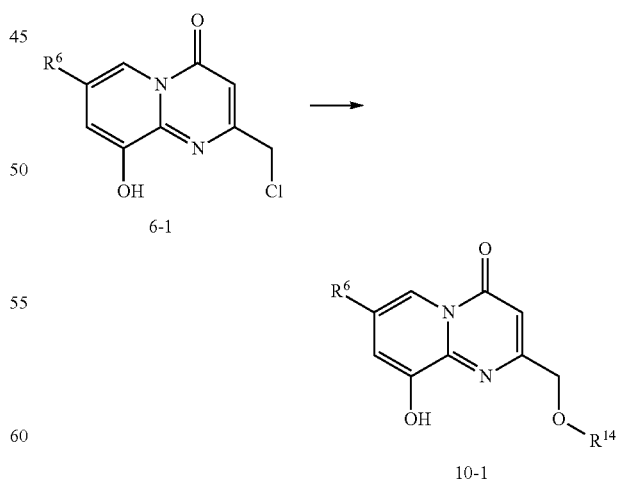

in which

R$^6$ is H or Cl; and

R$^{14}$ is C$_{1-3}$alkyl

2-(Ethoxymethyl)-9-hydroxy-4H-pyrido[1,2-a]pyrimidin-4-one (10-1)

The chloromethyl compound 6-1 (231 mg, 1.09 mmol) was dissolved in EtOH (17 mL) then treated with an aqueous solution of NaOH (5 mL, 6.25 mmol, 1.25 M). The reaction was then heated to 70° C. o/n. The reaction was cooled and filtered to remove some insoluble material. The filtrate was concentrated to 7 mL and the resulting orange solution was extracted with ether (15 mL). The aqueous layer was then acidified to pH 2 with conc. HCl (1 mL). The aqueous layer was then extracted into $CH_2Cl_2$ (×3) and the organic layers were dried over $Na_2SO_4$, filtered and concentrated to give an orange oil. Addition of 20% EtOAc/petroleum ether 40-60° C. (10 mL) afforded an off-white solid 10-1 that was collected by filtration (45 mg, 19% yield). $^1$H NMR (500 MHz, CDCl$_3$) δ1.21 (t, J=9.0 Hz, 3H), 3.59 (q, J=9.0 Hz, 2H), 4.47 (s, 2H), 6.37 (s, 1H), 7.20 (m, 2H), 8.46 (d, J=9.0 Hz, 1H). HPLC: $t_R$=6.21 min (98.3%). MS: m/z 221.1 [M+H]$^+$.

TABLE 10

Compounds prepared according to Example 10 (Scheme 10)

| Compound | Structure | MW | $^1$H NMR | MS |
|---|---|---|---|---|
| 1591 | 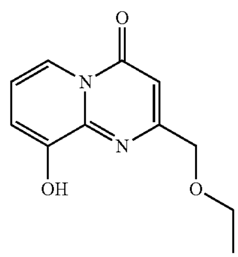 [SMILES: CCOCc1cc(=O)n2cccc(O)c2n1] | 220.2 | $^1$H NMR (500 MHz, d6-DMSO δ 1.21 (t, J = 9.0 Hz, 3H), 3.59 (q, J = 9.0 Hz, 2H), 4.47 (s, 2H), 6.37 (s, 1H), 7.20 (m, 2H), 8.46 (d, J = 9.0 Hz, 1H). | m/z 221.1 [M + H]$^+$ |
| 1646 | 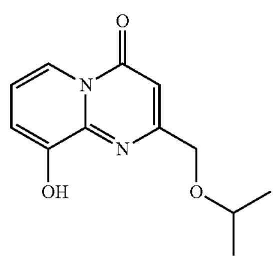 [SMILES: CC(C)OCc1cc(=O)n2cccc(O)c2n1] | 234.3 | $^1$H NMR (500 MHz, CDCl$_3$) δ 1.27 (d, J = 6.0 Hz, 6H), 3.76 (sept, J = 6.0 Hz, 1H), 4.52 (s, 2H), 6.66 (s, 1H), 7.03 (t, J = 7.0 Hz, 1H), 7.15 (d, J = 7.0 Hz, 1H), 8.53 (dd, J = 7.0, 1.5 Hz, 1H). | m/z 235.1 [M + H]$^+$ |
| 1701 | 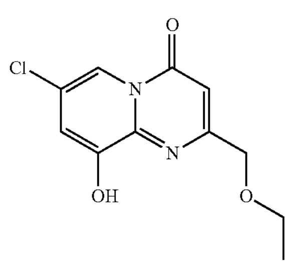 [SMILES: CCOCc1cc(=O)n2cc(Cl)cc(O)c2n1] | 254.7 | $^1$H NMR (400 MHz, d6-DMSO) δ 1.30 (t, J = 7.0 Hz, 3H), 3.65 (q, J = 7.0 Hz, 2H), 4.51 (s, 2H), 6.66 (s, 1H), 7.14 (d, J = 2.0 Hz, 1H), 8.58 (d, J = 2.0 Hz, 1H) | m/z 255.1 [M + H]$^+$ |
| 1705 | 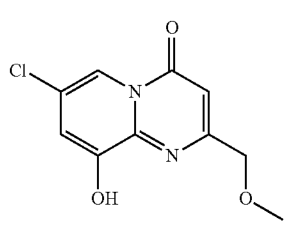 [SMILES: COCc1cc(=O)n2cc(Cl)cc(O)c2n1] | 240.6 | $^1$H NMR (400 MHz, d6-DMSO) δ 3.51 (s, 3H), 4.46 (s, 2H), 6.61 (s, 1H), 7.15 (d, J = 2.0 Hz, 1H), 8.58 (d, J = 2.0 Hz, 1H) | m/z 241.1 [M + H]$^+$ |

Example 11

Compounds containing alkoxymethyl group at position 3 can be prepared from the ester 5-2. Conversion of the phenol to a benzyl ether 11-1 followed by DIBAL reduction gives alcohol 11-2. The alcohol is then allowed to react with thionyl chloride to generate the intermediate alkyl chloride. Chloride displacement with an alcohol then gives alkoxymethyl compound 11-3. Ether cleavage provides the target alkoxymethyl compound 11-4. Similarly compounds containing and alkylaminomethyl group at position 3 can be prepared in analogous fashion. Alcohol 11-2 is converted to the alkylaminomethyl compound 11-5 via a chloride intermediate. Substitution with an amine generates the desired alkylaminomethyl product 11-5. Removal of the protecting group affords the target compounds 11-6 (Scheme 11).

2H), 5.31 (s, 2H), 7.43 (m, 5H), 7.50 (t, J=6.8 Hz, 1H), 7.72 (d, J=6.8 Hz, 1H), 8.76 (d, J=6.8 Hz, 1H), 8.82 (s, 1H).

9-(Benzyloxy)-3-(hydromethyl)-4H-pyrido[1,2-a]pyrimidin-4-one (11-2)

Ethyl-9-(benzyloxy)-4-oxo-4H-pyrido[1,2-a]pyrimidine-3-carboxylate (11-1) (1.54 g, 4.75 mmol) was dissolved in anhydrous 1:1 CH$_2$Cl$_2$/anhydrous ether (60 mL) and cooled to −10° C. in an ice/salt bath. A solution of DIBAL-H (11.0 mL, 11 mmol, 1.0 M in hexanes) was added dropwise over 15 minute. The resulting bright yellow solution was stirred under argon for 2 h. A further 1.0 mL of the above DIBAL-H solution was added and the reaction was left to warm to rt overnight. The reaction was cooled to 0° C. and quenched carefully with 10% K/Na$^+$ tartrate solution. Stirred at rt for

Scheme 11

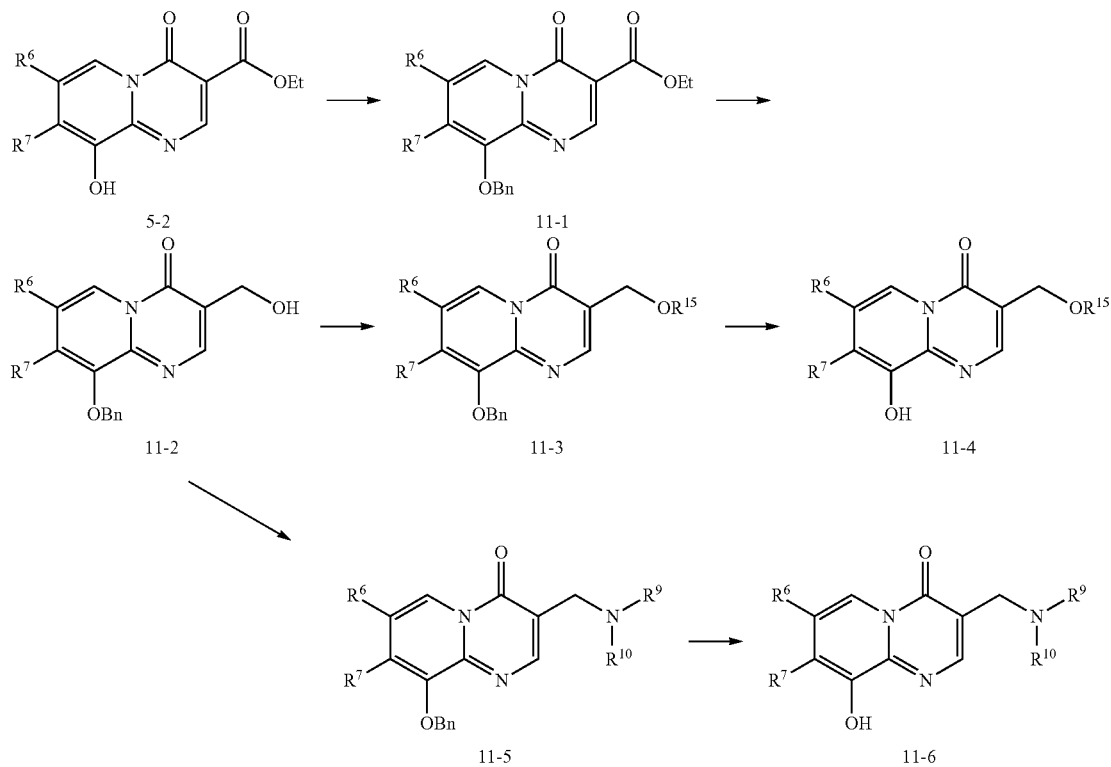

Compound 1424

Ethyl-9-(benzyloxy)-4-oxo-4H-pyrido[1,2-a]pyrimidine-3-carboxylate (11-1)

Ethyl-9-hydroxy-4-oxo-4H-pyrido[1,2-a]pyrimidine-3-carboxylate (7.5 g, 32.0 mmol) was dissolved in DMF (150 mL) then treated with K$_2$CO$_3$ (6.63 g, 48 mmol), followed by benzyl bromide (8.0 mL, 67.3 mmol). The reaction was stirred under N$_2$ for 3 days. To the reaction was added H$_2$O (50 mL) and the resulting tan solid was collected by filtration, washing with H$_2$O (×3), then petrol (×3) to afford (7.78 g, 75%) of ethyl-9-(benzyloxy)-4-oxo-4H-pyrido[1,2-a]pyrimidine-3-carboxylate (11-1) as a tan solid. $^1$H NMR (400 MHz, d6-DMSO) δ1.28 (t, J=7.2 Hz, 3H), 4.26 (q, J=7.2H, 2 h then the suspension was extracted into CH$_2$Cl$_2$ (×4). The combined organics were washed with brine, dried over MgSO$_4$, filtered and concentrated to afford the alcohol 11-2 as an oil (712 mg, 53%). $^1$H NMR (400 MHz, d6-DMSO) δ4.44 (d, J=6.0 Hz, 2H), 7.21 (t, J=7.2 Hz, 1H), 7.41 (m, 5H), 7.57 (d, J=7.2 Hz, 1H), 8.36 (s, 1H), 8.58 (d, J=7.2 Hz, 1H).

9-(Benzyloxy)-3-methoxymethyl)-4H-pyrido[1,2-a]-4-one (11-3)

Alcohol 11-2 (317 mg, 1.13 mmol) was dissolved in anhydrous CH$_2$Cl$_2$ (7 mL) and cooled to 0° C. Thionyl chloride (0.5 mL) was added dropwise and the reaction was stirred for 1.5 h then concentrated to afford the chloride in quantitative yield. The crude chloride was suspended in anhydrous CH$_2$Cl$_2$ (10 mL) cooled to 0° C. then treated with a methanolic solution of dimethylamine (1.5 mL, 3.0 mmol, 2.0 M). The reaction was warmed to rt and stirred for 3 days. Volatiles were removed in vacuo and the crude product was purified by flash chromatography eluting with 90% EtOAc/petroleum ether 40-60° C. to afford unreacted starting material. Further elution with 10% MeOH/CH$_2$Cl$_2$ provided methoxymethyl compound 11-3 (115 mg, 34% yield) as yellow oil. $^1$H NMR (400 MHz, d6-DMSO) δ3.21 (s, 3H), 4.38 (s, 2H), 5.25 (s, 2H), 7.29 (t, J=7.2 Hz, 1H), 7.39 (m, 5H), 7.56 (d, J=7.2 Hz, 1H), 8.30 (s, 1H), 8.49 (d, J=7.2 Hz, 1H).

9-Hydroxy-3-(methoxymethyl)-4H-pyrido[1,2-a]pyrimidin-4-one (11-4) (1398)

9-(Benzyloxy)-3-methoxymethyl)-4H-pyrido[1,2-a]-4-one 11-3 (112 mg, 0.362 mmol) in anhydrous CH$_2$Cl$_2$ (7 mL) was cooled to 0° C. then treated with boron tribromide (180 μL, 1.86 mmol). The reaction was warmed to rt and then stirred for 18 h. The reaction was cooled to 5° C. then quenched cautiously with MeOH (15 mL). The reaction was stirred at rt for 30 min then MeOH was removed in vacuo. The process was repeated (×3) and the compound was dried under high vacuum. The residue was then treated with MeOH (1 mL) and ether (20 mL) to precipitate a brown powder after sonication. The product was collected by filtration washing with ether three times to afford the 9-hydroxy-3-(methoxymethyl)-4H-pyrido[1,2-a]pyrimidin-4-one 11-4 as a brown solid (28 mg, 38%). $^1$H NMR (400 MHz, d6-DMSO) δ3.29 (s, 3H), 4.36 (s, 2H), 7.46 (t, J=7.2 Hz, 1H), 7.54 (d, J=7.2 Hz, 1H), 8.22 (s, 1H), 8.59 (d, J=7.2 Hz, 1H). HPLC: t$_R$=2.31 min (98.1%). MS: m/z 207.0 [M+H]$^+$.

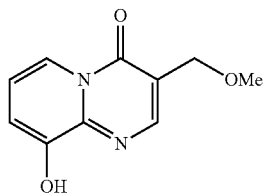

1398

9-Benzyloxy-3-((dimethylamino)methyl)-4H-pyrido[1,2-a]pyrimidin-4-one (11-5)

Alcohol 11-2 (317 mg, 1.13 mmol) was dissolved in anhydrous CH$_2$Cl$_2$ (7 mL) and cooled to 0° C. Thionyl chloride (0.5 mL) was added dropwise and the reaction was stirred for 1.5 h then concentrated to afford the chloride in quantitative yield. The chloride intermediate (344 mg, 1.14 mmol) was dissolved in anhydrous CH$_2$Cl$_2$ (10 mL) and cooled to 0° C. Dimethylamine hydrogenchloride (512 mg, 6.28 mmol) was added followed by DIEA (1.10 mL, 6.28 mmol) and the resulting orange/red solution was warmed to rt o/n. Volatiles were removed in vacuo then taken up in CH$_2$Cl$_2$ and sat. NaHCO$_3$. The aqueous layer was extracted into CH$_2$Cl$_2$ (×2) and the combined organic extracts were dried over Na$_2$SO$_4$, filtered, concentrated and purified by flash chromatography eluting with 5% MeOH/CH$_2$Cl$_2$. The product was then converted to the hydrogen chloride salt. The residue was stirred in conc. HCl (2 mL) for 30 min then solvent was removed under vacuum. A white solid was isolated and washed with MeOH (2 mL)/ether (15 mL). Further washing with ether provided the 9-benzyloxy-3-((dimethylamino)methyl)-4H-pyrido[1,2-a]pyrimidin-4-one HCl salt 11-5 as a white powder (104 mg, 29%). $^1$H NMR (400 MHz, d6-DMSO) δ2.77 (s, 3H), 2.79 (s, 3H), 4.25 (d, J=6.0 Hz, 2H), 5.36 (s, 2H), 7.42 (m, 5H), 7.55 (d, J=6.8 Hz, 1H), 7.44 (d, J=6.8 Hz, 1H), 7.66 (d, J=6.8 Hz, 1H), 8.37 (s, 1H), 8.68 (d, J=6.8 Hz, 1H). 10.29 (br s, 1H).

3-((Dimethylamino)methyl)-9-hydroxy-4H-pyrido[1,2-a]pyrimidin-4-one hydrogen chloride (11-6) (1424)

9-Benzyloxy-3-((dimethylamino)methyl)-4H-pyrido[1,2-a]pyrimidin-4-one HCl 11-5 was dissolved in MeOH (8 mL). Then 10% Pd on carbon (13 mg) was added under argon. The flask was evacuated three times then placed under a balloon of hydrogen. The reaction was stirred at rt for 4 h then filtered and concentrated to afford 3-((dimethylamino)methyl)-9-hydroxy-4H-pyrido[1,2-a]pyrimidin-4-one hydrogen chloride 11-6 a pale yellow solid (30 mg, 37% yield). $^1$H NMR (400 MHz, D$_2$O) δ3.01 (s, 6H), 4.48 (s, 2H), 7.73 (t, J=6.8 Hz, 1H), 7.88 (d, J=6.8 Hz, 1H), 8.84 (s, 1H), 8.84 (d, J=6.8 Hz, 1H). HPLC: t$_R$=1.74 min (100%). MS: m/z 220.1 [M+H]$^+$.

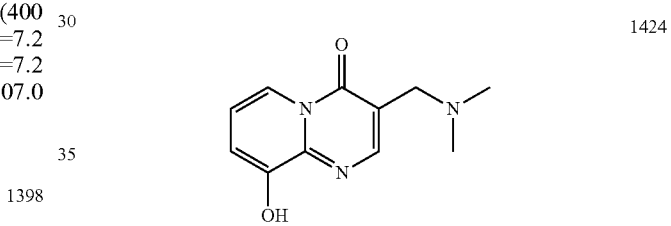

1424

Example 12

Compounds containing an S-methylene-dithiocarbamate group 12-2 can be prepared by reaction of intermediate 6-1 with carbon disulfide and an appropriately substituted amine in THF (Scheme 12).

Scheme 12

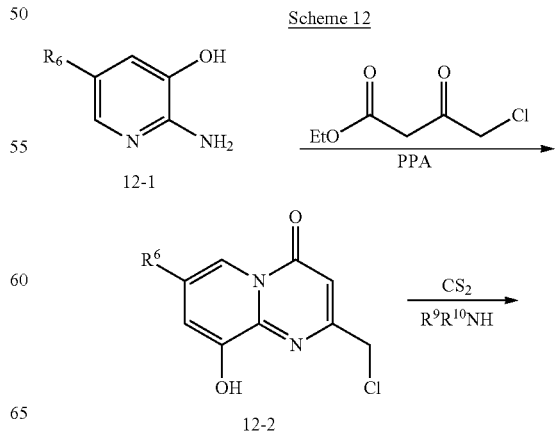

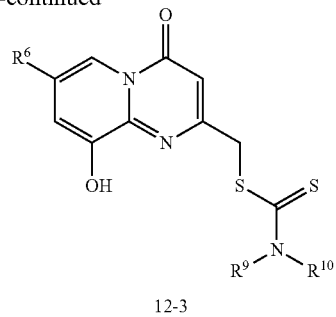

in which
R⁶ is Cl;
R⁹ and R¹⁰ are independently selected from H, $C_{1-2}$alkyl and $CH_2$ pyridine; or
R⁹ and R¹⁰ together with the N to which they are attached from an optionally substituted 6 membered ring optionally containing N.

Compound 1713

7-Chloro-2-(chloromethyl)-9-hydroxy-4H-pyrido[1,2-a]pyrimidin-4-one (12-2)

5-chloro-2-amino-pyridinol 12-1 (4.3 g, 29.7 mmol), 4-chloroacetoacetate (8.5 mL) were heated together in polyphosphoric acid (20 mL) at 110° C. for 2.5 h. The reaction mixture was cooled, crushed ice (30 g) was added and the pH of the mixture was adjusted to 5, by the addition of 2N NaOH. A brown precipitate formed, that was collected by filtration, washing with $H_2O$ until the washings were colourless. The product was dried to afford the chloromethyl derivative as a brown powder (7.27 g, 100%). ¹H NMR (500 mHz, d6-DMSO) δ4.67 (s, 2H), 6.59 (s, 1H), 7.27 (d, J=2.0 Hz, 1H), 8.46 (d, J=2.0 Hz, 1H).

(7-Chloro-9-hydroxy-4-oxo-4H-pyrido[1,2-a]pyrimidin-2-yl)methyl morpholine-4-dithiocarbamate (12-3) (1713)

7-Chloro-2-(chloromethyl)-9-hydroxy-4H-pyrido[1,2-a]pyrimidin-4-one (12-1) (235 mg, 0.96 mmol) was dissolved in THF (4 mL), then carbon disulfide (65 μL) was added at 0° C., followed by the addition of morpholine (175 μL). The reaction was stirred at 0° C. for 30 min then allowed to warm to rt over 18 h. The reaction was quenched by the addition of $H_2O$ (2 mL). After stirring for 2 h at rt, a beige precipitate resulted that was collected by filtration. ¹H NMR (400 MHz, d6-DMSO) δ 3.67 (m, 4H), 3.97 (m, 2H), 4.23 (m, 2H), 4.59 (s, 2H), 6.50 (s, 1H), 7.23 (d, J=2.0 Hz, 1H), 8.41 (d, J=2.0 Hz, 1H). MS (ESI+ve): m/z 371.9 [M+H]⁺.

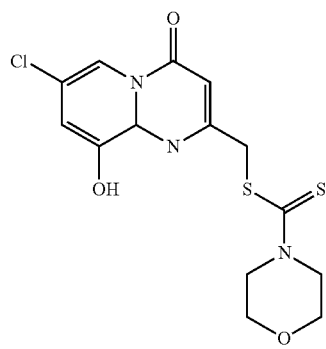

TABLE 11

Compounds prepared according to Example 12 (Scheme 12)

| Compound | Structure | MW | Proton NMR | MS |
|---|---|---|---|---|
| 1714 | 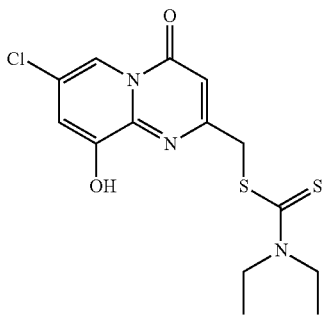 [SMILES: CCN(CC)C(=S)SCc1cc(=O)n2cc(Cl)cc(O)c2n1] | 357.9 | ¹H NMR (500 MHz, d6-DMSO) δ 1.18 (m, 6H), 3.76 (q, J = 7.5 Hz, 2H), 3.96 (q, J = 7.5 Hz, 2H), 6.27 (s, 1H), 6.78 (d, J = 2.0 Hz, 1H), 7.87 (d, J = 2.0 Hz, 1H) | m/z 358.0 [M + H]⁺ |
| 1720 | 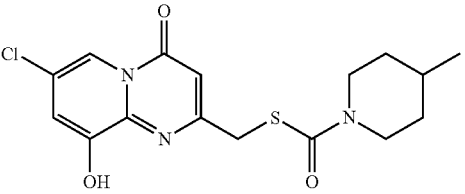 | 383.9 | ¹H NMR (400 MHz, d6-DMSO) δ 0.91 (m, 5H), 1.11 (m, 3H), 1.21 (m, 2H), 1.60 (m, 1H), 1.78 (m, 4H), 2.80 (m, 2H), 3.19 (m, 2H), 4.42 (br s, 1H), 4.59 (d, J = 5.6 Hz, 1H), 5.24 (br s, 1H), 6.51 (s, 1H), 7.29 (d, J = 2.0 Hz, 1H), 8.44 (s, 1H). | m/z 384.1 [M + H]⁺ |

TABLE 11-continued

Compounds prepared according to Example 12 (Scheme 12)

| Compound | Structure | MW | Proton NMR | MS |
|---|---|---|---|---|
| 1721 | 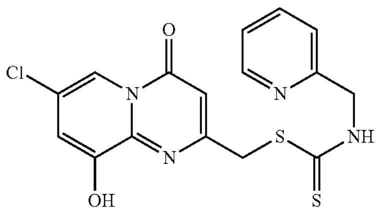 [SMILES: O=c1cc(CSC(=S)NCc2ccccn2)nc2c(O)cc(Cl)cn12] | 392.9 | ¹H NMR (400 MHz, d6-DMSO) δ 4.52 (s, 2H), 5.16 (d, J = 7.6 Hz, 2H), 6.52 (s, 1H), 7.36 (d, J = 2.0 Hz, 1H), 7.98 (m, 2H), 8.36 (t, J = 7.2 Hz, 1H), 8.46 (d, J = 2.0 Hz, 1H), 8.79 d, J = 5.2 Hz, 1H), 11.67 (s, 1H) | m/z 393.025 [M + H]⁺ |

Example 13

Acyl hydrazine and acyl hydrazide derivatives can be prepared from an ester intermediate 11-1 (Scheme 11) by heating with an aqueous solution of hydrazine hydrate in Ethanol to generate compound 13-1. Hydrazine 13-1 is allowed to react with commercially available aldehydes to provide hydrazide 13-2 (Scheme 13).

Scheme 13

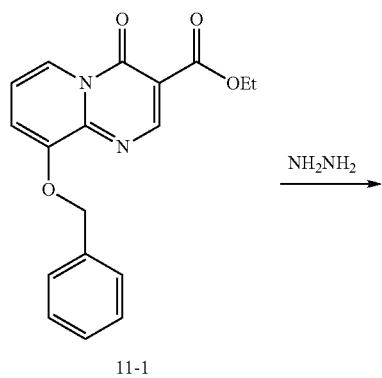

11-1

NH₂NH₂ →

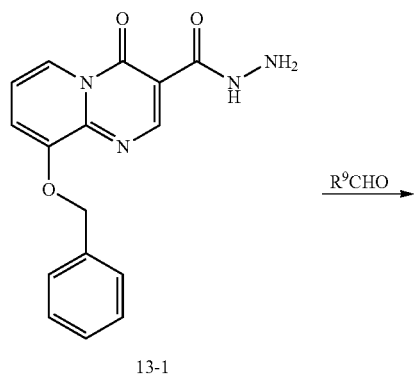

13-1

R⁹CHO →

-continued

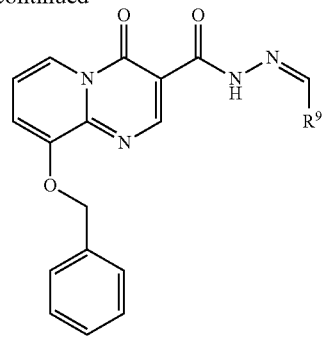

13-2 in which
R⁹ is optionally substituted imidazolyl.

Compound 1711

9-(Benzyloxy)-4-oxo-4H-pyrido[1,2-a]pyrimidinine-3-carbohydrazide (13-1) (1711)

To a solution of Ethyl 9-(benzyloxy)-4-oxo-4H-[1,2-a] pyrimidine-3-carboxylate (11-1) (493 mg, 1.59 mmol), was added hydrazine hydrate (2 mL) and three drops of conc. H₂SO₄. The reaction was heated to reflux for 3 h, then cooled. The hydrazide precipitated out of solution as a fluffy white solid and was collected by filtration (388 mg, 83%). ¹H NMR (400 MHz, d6-DMSO) δ4.63 (br s, 2H), 5.33 (s, 2H), 7.42 (m, 6H), 7.70 (d, J=8.0 Hz, 1H), 8.79 (d, J=8.0 Hz, 1H), 8.97 (s, 1H), 9.76 (br s, 1H). MS (ES+ve): m/z 311.11 [M+H]⁺.

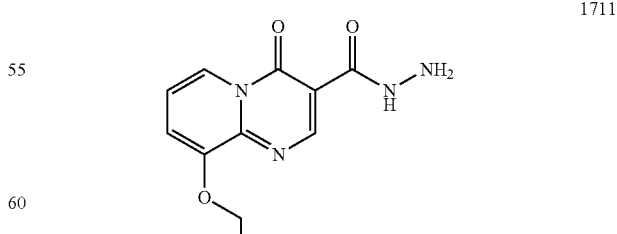

1711

Compound 1723

9-Benzyloxy-N"-2-(hydroxybenzilidene)-4-oxo-4-H-pyrido[1,2-a]pyrimidine-3-carbohydrazide (13-2) (1723)

9-(Benzyloxy)-4-oxo-4H-pyrido[1,2-a]pyrimidinine-3-carbohydrazide (13-1) (80 mg, 0.258 mmol), salicylaldehyde (50 mg, 0.41 mmol) were heated to reflux in EtOH (12 mL) for 4 h. A cream precipitate resulted. After allowing the reaction mixture to cool, the resulting 9-Benzyloxy-N"-2-(hydroxybenzilidene)-4-oxo-4-H-pyrido[1,2-a]pyrimidine-3-carbohydrazide (13-2) (80 mg, 75%) was collected by filtration. $^1$H NMR (400 MHz, d6-DMSO) δ5.32 (s, 2H), 6.89 (m, 2H), 7.27 (t, J=8.0 Hz, 1H), 7.37 (m, 4H), 7.52 (m, 3H), 7.74 (d, J=8.0 Hz, 1H), 8.68 (s, 1H), 8.80 (d, J=7.2 Hz, 1H), 9.03 (s, 1H), 11.25 (br s, 1H), 12.1 (br s, 1H). MS (ESI+ve): m/z 415.2 [M+H]$^+$.

TABLE 12

Compounds prepared according to Example 13 (Scheme 13)

| Compound | Structure | MW | Proton NMR | MS |
|---|---|---|---|---|
| 1723 | 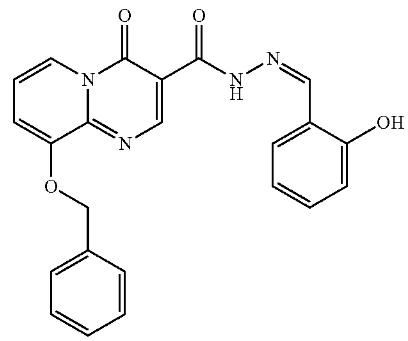 [SMILES: O=C(N/N=C\c1ccccc1O)c1cnc2c(OCc3ccccc3)cccn2c1=O] | 414.41 | $^1$H NMR (400 MHz, d6-DMSO) δ 5.32 (s, 2H), 6.89 (m, 2H), 7.27 (t, J = 8.0 Hz, 1H), 7.37 (m, 4H), 7.52 (m, 3H), 7.74 (d, J = 8.0 Hz, 1H), 8.68 (s, 1H), 8.80 (d, J = 7.2 Hz, 1H), 9.03 (s, 1H), 11.25 (br s, 1H), 12.1 (br s, 1H). | m/z 415.2 [M + H]$^+$ |
| 1724 | 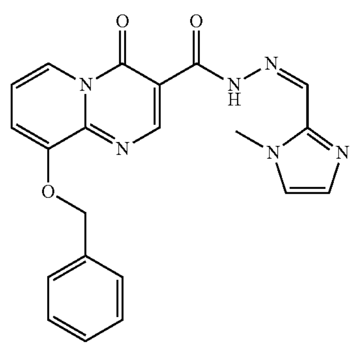 [SMILES: Cn1ccnc1/C=N\NC(=O)c1cnc2c(OCc3ccccc3)cccn2c1=O] | 402.41 | $^1$H NMR (400 MHz, d6-DMSO) δ 3.96 (s, 3H), 5.36 (s, 2H), 7.40 (m, 4H), 7.52 (m, 4H), 7.78 (d, J = 6.8 Hz, 1H), 8.63 (s, 1H), 8.83 (d, J = 6.8 Hz, 1H), 9.05 (s, 1H), 12.3 (s, 1H), | m/z 403.2 [M + H]$^+$ |
| 1732 | 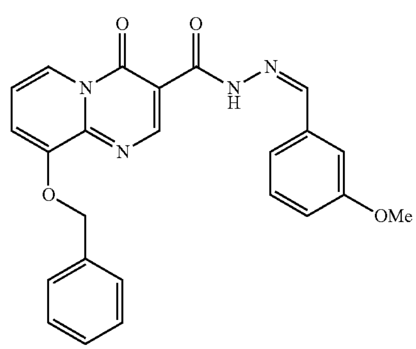 [SMILES: COc1cccc(/C=N\NC(=O)c2cnc3c(OCc4ccccc4)cccn3c2=O)c1] | 428.44 | $^1$H NMR (400 MHz, d6-DMSO-did not fully dissolve) δ 3.77 (s, 3H), 5.32 (s, 2H), 7.01 (m, 1H), 7.08 (m, 1H), 7.28 (m, 2H), 7.37 (m, 1H), 7.41 (m, 2H), 7.50 (m, 2H), 7.77 (d, J = 7.2 Hz, 1H), 8.42 (s, 1H), 8.65 (s, 1H), 8.82 (m, 1H), 9.03 (s, 1H), 12.05 (s, 1H) | m/z 429.2 [M + H]$^+$ |

Example 14

2-Methylsubstituted pyridopyrimidine derivatives can be synthesized by reaction of 2-amino-3-pyridinols 14-1 with commercially available ethyl (acetoacetates) 14-2 to generate the 2-substituted pyridopyrimidine ring system 14-3. Regioselective iodination to provide 14-4 was achieved by the action of iodine and hydrogen peroxide. A Suzuki coupling reaction can be carried out with Pd(PPh$_3$)$_4$ as catalyst and commercially available boronic acids R$^7$B(OH)$_2$ or boronate esters R$^7$B(OR$^5$)$_2$ to afford aryl and heteroaryl compounds 14-5 (Scheme 14).

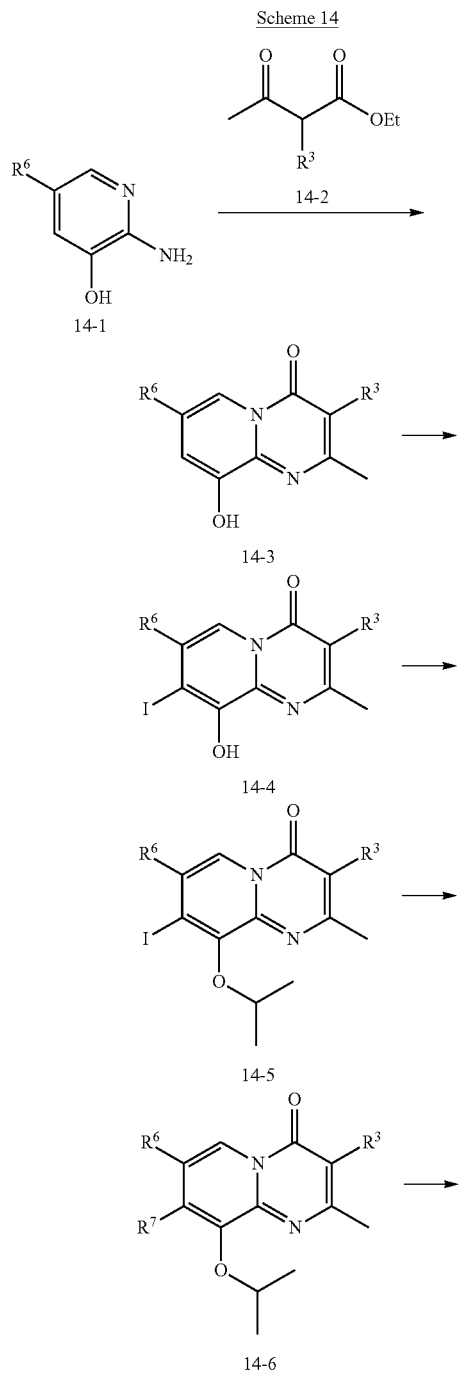

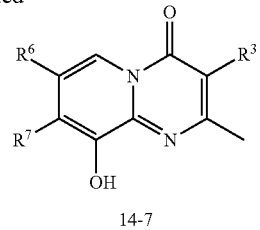

in which R$^3$ is O$_1$-4alkyl or benzyl;

R$^6$ is H or Cl; and

R$^7$ is H, I, pyridinyl optionally substituted pyrazolyl or optionally substituted isoxazolyl.

3-butyl-7-chloro-9-hydroxy-2-methyl-4H[1,2-a]pyrimidin-4-one (14-3) (1667)

2-amino-5-chloropyridinol (2.0 g, 14 mmol), ethyl-2-butylacetoacetate (3.87 g, 20 mmol) and polyphosphoric acid (25 g) were heated together at 110° C. for 4 hours. After cooling, H$_2$O was added and the pH taken to 4 with 2N NaOH. The resulting yellow precipitate was collected by filtration, washed with H$_2$O then ether and dried to afford 3-butyl-7-chloro-9-hydroxy-2-methyl-4H[1,2-a]pyrimidin-4-one PB1667 (2.54 g, 69%) as a yellow powder. $^1$H NMR (500 MHz, d6-DMSO) δ 0.94 (t, J=7.5 Hz, 2H), 1.42 (m, 2H), 1.52 (m, 2H), 2.48 (s, 3H), 2.67 (t, J=7.4 Hz, 2H), 7.01 (s, 1H), 8.48 (s, 1H). MS: m/z 267.1[M+H]$^+$.

3-butyl-7-chloro-9-hydroxy-8-iodo-2-methyl-4H[1,2-a]pyrimidin-4-one (14-4) (1688)

To a solution of 3-butyl-7-chloro-9-hydroxy-2-methyl-4H[1,2-a]pyrimidin-4-one (14-3) (900 mg, 3.4 mmol) in EtOH (35 mL) was added iodine (940 mg, 3.7 mmol), followed by the dropwise addition of 30% aqueous hydrogen peroxide (380 ML). The reaction was stirred o/n at rt and the resulting precipitate was filtered off, washing with EtOH (3×5 mL) to provide the 3-butyl-7-chloro-9-hydroxy-8-iodo-2-methyl-4H[1,2-a]pyrimidin-4-one (14-4) PB1688 as yellow powder (955 mg, 72% yield). $^1$H NMR (500 MHz, d6-DMSO) δ 0.90 (t, J=7.0 Hz, 3H), 1.33 (m, 2H), 1.43 (m, 2H), 2.53 (s, 3H), 2.55 (s, 2H), 8.31 (s, 1H).

3-butyl-7-chloro-9-isopropoxy-8-iodo-2-methyl-4H[1,2-a]pyrimidin-4-one (14-5) (1689)

To a stirred solution of 3-butyl-7-chloro-9-hydroxy-8-iodo-2-methyl-4H[1,2-a]pyrimidin-4-one 14-4 (955 mg, 2.40 mmol) in DMF (12 mL) was added K$_2$CO$_3$ (1.35 g, 9.7 mmol), followed by 2-bromopropane (700 μL, 7.5 mmol) and the reaction was stirred at 50° C. for 6 days. The reaction was diluted with H$_2$O and EtOAc and the aqueous layer was further extracted into EtOAc (×2). The resulting organic layers were washed with H$_2$O, brine, dried over Na$_2$SO$_4$, filtered and concentrated to give 3-butyl-7-chloro-9-isopropoxy-8-iodo-2-methyl-4H[1,2-a]pyrimidin-4-one (14-5) 1689 as a yellow solid (611 mg, 59% yield). $^1$H NMR (500 MHz, d6-DMSO) δ0.97 (t, J=7.0 Hz, 3H), 2.38 (m, 8H), 1.42 (m, 2H), 2.41 (s, 3H), 2.58 (m, 2H), 5.39 (m, 1H), 8.67 (s, 1H). MS: m/z 435.0 [M+H]$^+$.

3-butyl-7-chloro-9-isopropoxy-2-methyl(pyridin-4-yl)-4H[1,2-a]pyrimidin-4-one (14-6)

3-butyl-7-chloro-9-isopropoxy-8-iodo-2-methyl-4H[1,2-a]pyrimidin-4-one 14-5 (300 mg, 0.69 mmol) was dissolved in DMF (15 mL) and 2M K$_2$CO$_3$ (1.4 mL) in a Schlenk flask. The solution was degassed and back-filled with argon (×2). Then 4-pyridinyl boronic acid (130 mg, 1.03 mmol) and Pd(PPh$_3$)$_4$ (55 mg, 7 mol %) were added to the reaction at which time the flask was degassed a further 5 times. The reaction flask was heated to 95° C. o/n. After cooling, volatiles were removed under reduced pressure. The residue was then diluted with H$_2$O (20 mL) and extracted into EtOAc (3×10 mL). The combined organic layers were washed with H$_2$O (2×10 mL), dried Na$_2$SO$_4$, filtered and concentrated to afford crude 3-butyl-7-chloro-9-isopropoxy-2-methyl(pyridin-4-yl)-4H[1,2-a]pyrimidin-4-one (14-6) as a brown oil (284 mg). Compound was taken onto the next step without purification.

3-butyl-7-chloro-9-hydroxy-2-methyl(pyridin-4-yl)-4H[1,2-a]pyrimidin-4-one (14-7) (1690)

3-butyl-7-chloro-9-isopropoxy-2-methyl(pyridin-4-yl)-4H[1,2-a]pyrimidin-4-one (14-6) (284 mg, 0.74 mmol) was dissolved in anhydrous CH$_2$Cl$_2$ (5 mL) cooled to −10° C. then a 1.0M solution of boron trichloride in CH$_2$Cl$_2$ (5.2 mL, 5.2 mmol) was added. After stirring for 5 min the reaction was warmed to rt o/n. Methanol was cautiously added to the reaction which was then concentrated in vacuo. This procedure was repeated five times then the residue was sonicated with EtOH only, producing 3-butyl-7-chloro-9-hydroxy-2-methyl(pyridin-4-yl)-4H[1,2-a]pyrimidin-4-one (14-7) PB1690 as a cream coloured solid that was collected by filtration (116 mg, 46% yield). $^1$H NMR (500 MHz, d6-DMSO) δ 0.91 (t, J=7.0 Hz, 3H), 1.35 (m, 2H), 1.47 (m, 2H), 2.58 (s, 3H), 2.60 (m, 2H), 8.17 (s, 1H), 8.23 (s, 1H), 9.34 (br s, 1H). MS: m/z 344.1 [M+H]$^+$.

TABLE 13

Compounds prepared according to Example 14 (Scheme 14)

| Compound | Structure | MW | Proton NMR | Mass Spec |
| --- | --- | --- | --- | --- |
| 1662 | 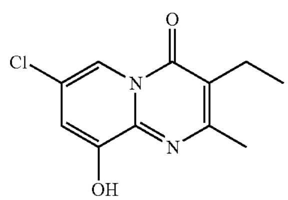 [SMILES: CCc1c(C)nc2c(O)cc(Cl)cn2c1=O] | 238.7 | $^1$H NMR (400 MHz, d6-DMSO) δ 1.10 (t, J = 7.0 Hz, 3H), 2.52 (s, 3H), 2.63 (q, J = 7.0 Hz, 2H), 7.15 (s, 1H), 8.41 (s, 1H) | m/z 239.1 [M + H]$^+$ |
| 1663 | 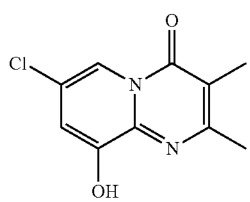 | 224.6 | $^1$H NMR (500 MHz, d6-DMSO) δ 2.11 (s, 3H), 2.42 (s, 3H), 7.09 (d, J = 2.0 Hz, 1H), 8.34 (d, J = 2.0 Hz, 1H) | m/z 225.0 [M + H]$^+$ |
| 1665 | 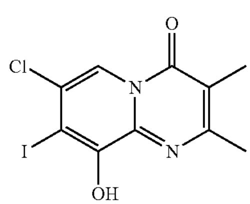 [SMILES: Cc1nc2c(O)c(I)c(Cl)cn2c(=O)c1C] | 350.5 | $^1$H NMR (500 MHz, d6-DMSO) δ 2.08 (s, 3H), 2.44 (s, 3H), 8.19 (s, 1H). | m/z 350.9 [M + H]$^+$ |
| 1666 | 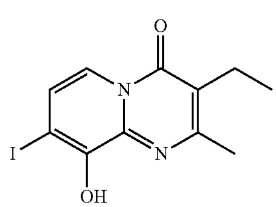 [SMILES: CCc1c(C)nc2c(O)c(I)ccn2c1=O] | 339.4 | $^1$H NMR (400 MHz, d6-DMSO) δ 1.06 (t, J = 7.2 Hz, 3H), 2.48 (s, 3H), 2.57 (q, J = 7.2 Hz, 2H), 7.47 (d, J = 7.6 Hz, 1H), 8.10 (d, J = 7.6 Hz, 1H) | m/z 331.1 [M + H]$^+$ |
| 1667 | 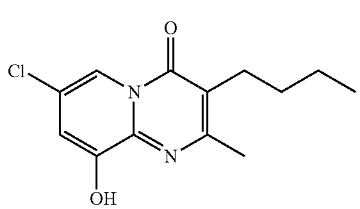 [SMILES: CCCCc1c(C)nc2c(O)cc(Cl)cn2c1=O] | 266.7 | $^1$H NMR (500 MHz, d6-DMSO) δ 0.94 (t, J = 7.5 Hz, 2H), 1.42 (m, 2H), 1.52 (m, 2H), 2.48 (s, 3H), 2.67 (t, J = 7.4 Hz, 2H), 7.01 (s, 1H), 8.48 (s, 1H) | m/z 267.1 [M + H]$^+$ |

TABLE 13-continued

Compounds prepared according to Example 14 (Scheme 14)

| Compound | Structure | MW | Proton NMR | Mass Spec |
|---|---|---|---|---|
| 1672 | 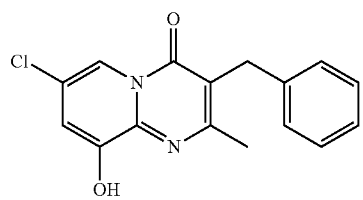 [SMILES: Cc1nc2c(O)cc(Cl)cn2c(=O)c1Cc1ccccc1] | 300.7 | $^1$H NMR (500 MHz, d6-DMSO) δ 2.42 (s, 3H), 3.98 (s, 2H), 7.16 (m, 2H), 7.23 (m, 4H), 8.42 (s, 1H) | m/z 301.1 [M + H]$^+$ |
| 1673 | 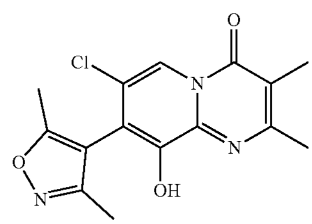 [SMILES: Cc1noc(C)c1-c1c(Cl)cn2c(=O)c(C)c(C)nc2c1O] | 319.7 | $^1$H NMR (500 MHz, d6-DMSO) δ 2.11 (s, 3H), 2.14 (s, 2H), 2.29 (s, 3H), 2.50 (s, 3H), 8.49 (s, 1H) | m/z 320.1 [M + H]$^+$ |
| 1687 | 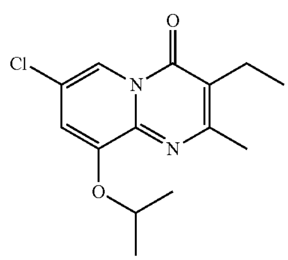 [SMILES: CCc1c(C)nc2c(OC(C)C)cc(Cl)cn2c1=O] | 280.8 | $^1$H NMR (500 MHz, d6-DMSO) δ 1.05 (t, J = 7.5 Hz, 3H), 1.34 (s, 3H), 1.35 (s, 3H), 2.41 (s, 3H), 2.61 (q, J = 7.5 Hz, 2H), 4.87 (sept, J = 6.0 Hz, 1H), 7.31 (d, J = 1.5 Hz, 1H), 8.45 (d, J = 1.5 Hz, 1H) | m/z 281.1 [M + H]$^+$ |
| 1688 | 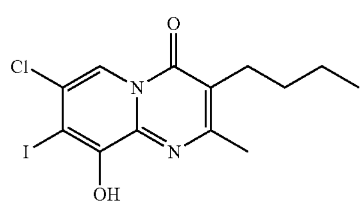 [SMILES: CCCCc1c(C)nc2c(O)c(I)c(Cl)cn2c1=O] | 392.6 | $^1$H NMR (500 MHz, d6-DMSO) δ 0.90 (t, J = 7.0 Hz, 3H), 1.33 (m, 2H), 1.43 (m, 2H), 2.53 (s, 3H), 2.55 (s, 2H), 8.31 (s, 1H) | m/z 393.0 [M + H]$^+$ |
| 1689 | 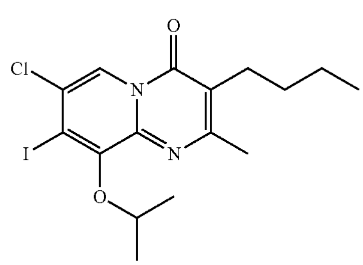 [SMILES: CCCCc1c(C)nc2c(OC(C)C)c(I)c(Cl)cn2c1=O] | 434.7 | $^1$H NMR (500 MHz, d6-DMSO) δ 0.97 (t, J = 7.0 Hz, 3H), 2.38 (m, 8H), 1.42 (m, 2H), 2.41 (s, 3H), 2.58 (m, 2H), 5.39 (m, 1H), 8.67 (s, 1H) | m/z 435.0 [M + H]$^+$ |
| 1690 | 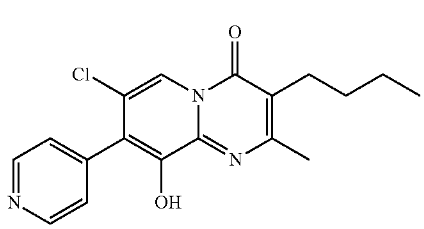 [SMILES: CCCCc1c(C)nc2c(O)c(-c3ccncc3)c(Cl)cn2c1=O] | 343.8 | $^1$H NMR (500 MHz, d6-DMSO) δ 0.91 (t, J = 7.0 Hz, 3H), 1.35 (m, 2H), 1.47 (m, 2H), 2.58 (s, 3H), 2.60 (m, 2H), 8.17 (s, 1H), 8.23 (s, 1H), 9.34 (br s, 1H) | m/z 344.1 [M + H]$^+$ |

TABLE 13-continued

Compounds prepared according to Example 14 (Scheme 14)

| Compound | Structure | MW | Proton NMR | Mass Spec |
|---|---|---|---|---|
| 1694 | 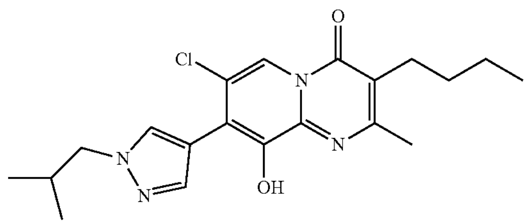 [SMILES: CCCCc1c(C)nc2c(O)c(-c3cnn(CC(C)C)c3)c(Cl)cn2c1=O] | 388.89 | ¹H NMR (500 MHz, d6-DMSO) δ 0.85 (s, 3H), 0.87 (s, 3H), 0.92 (t, J = 7.0 Hz, 3H), 1.35 (m, 2H), 1.44 (m, 2H), 2.14 (m, 1H), 2.58 (s, 3H), 4.00 (d, J = 7.0 Hz, 2H), 7.97 (s, 1H), 8.26 (s, 1H), 8.43 (s, 1H) | m/z 389.3 [M + H]⁺ |
| 1698 | 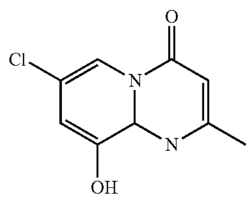 | 210.62 | ¹H NMR (400 MHz, d6-DMSO) δ 2.47 (s, 3H), 6.52 (s, 1H), 7.78 (d, J = 1.6 Hz, 1H), 8.60 (d, J = 1.6 Hz, 1H) | m/z 211.0 [M + H]⁺ |

Example 15

7-Substituted sulphonamides can be prepared from pyridopyrimidines 15-1. A regioselective nitration ortho to the phenol followed by reduction to the aniline 15-3 is achieved with sodium dithionite. Reaction of the aniline with sulfonyl chloride generates the target sulphonamide 15-4.

Scheme 15

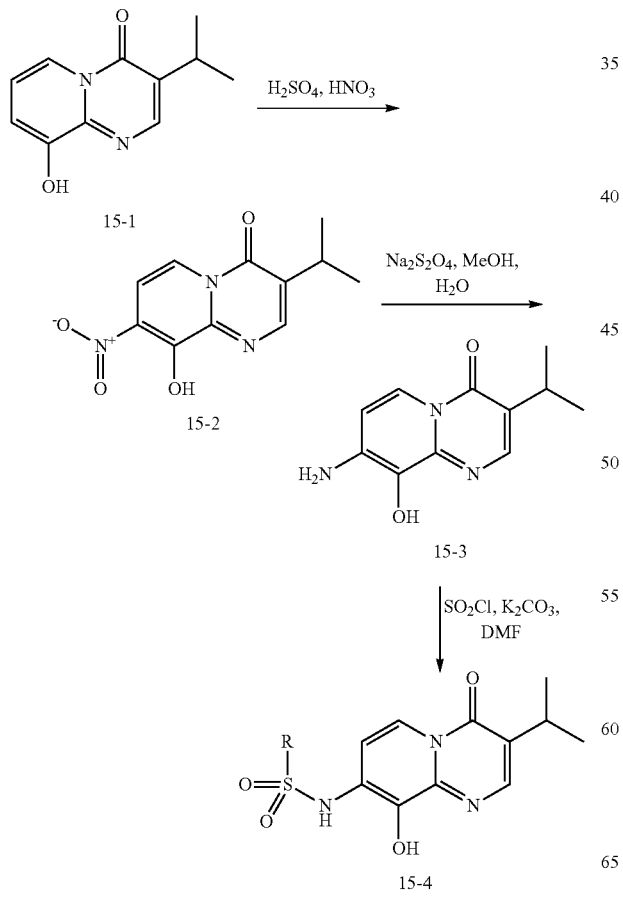

Compound 1717

9-Hydroxy-3-isopropyl-8-nitro-4H-pyrido[1,2-a]pyrimidin-4-one (15-2) (1704)

The phenol 15-1 (1.0 g, 4.90 mmol) was dissolved in concentrated sulfuric acid (4.8 mL) and cooled to 0O. A 70% solution of nitric acid (0.38 mL, 5.90 mmol) was added dropwise to this solution causing a yellow colour change. The reaction was stirred at 0O for 1 h, then at RT for 1.5 h. Ice was added and the mixture was stirred for 1 h, then filtered to afford a yellow solid was washed with water (×2) and air dried to give hydroxy-3-isopropyl-8-nitro-4H-pyrido[1,2-a]pyrimidin-4-one 15-2 (0.78 g, 60%). ¹H NMR (400 MHz, d₆-DMSO) δ1.21 (s, 3H), 1.22 (s, 3H), 3.05 (m, J=6.8 Hz, 1H), 7.64 (d, J=8.0 Hz, 1H), 7.80 (d, J=8.0 Hz, 1H), 7.88 (s, 1H). HPLC (254 nm): $t_R$=8.81 (96%).

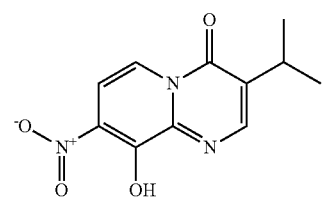

1704

8-Amino-9-hydroxy-3-isopropyl-4H-pyrido[1,2-a]pyrimidin-4-one (15-3)

To a stirred suspension of the nitro compound (15-2) (0.77 g, 3.50 mmol) in a 1:1 mixture of methanol and water (12 mL each) was added sodium dithionite (3.24 g, 18.6 mmol) and the mixture was stirred under a nitrogen atmosphere for 17 h. The majority of methanol was removed under reduced pressure before the precipitate was filtered and washed with water (×3) and air dried. The desired product 8-Amino-9-hydroxy-3-isopropyl-4H-pyrido[1,2-a]pyrimidin-4-one (15-3) was isolated as a yellow solid (0.46 g, 60%). ¹H NMR (400 MHz, d₆-DMSO) δ1.25 (s, 3H), 1.27 (s, 3H), 3.13 (m, J=6.8 Hz, 1H), 5.82 (bs, 2H), 6.88 (d, J=7.6 Hz, 1H), 7.98 (s, 1H), 8.45 (d, J=7.6 Hz, 1H).

4-Chloro-N-(9-hydroxy-3-isopropyl-4-oxo-4H-pyrido[1,2-a]pyrimidin-8-yl)benzenesulfonamide 15-4 (1717)

The reaction was conducted according to the general procedure above using the amine (50 mg, 0.23 mmol) and 4-chlorobenzene sulfonyl chloride (60 mg, 0.30 mmol). Concentration gave a brown gum that was sonicated in water, filtered, washed with water and air dried. 4-Chloro-N-(9-hydroxy-3-isopropyl-4-oxo-4H-pyrido[1,2-a]pyrimidin-8-yl)benzenesulfonamide was obtained as a tan solid (38.4 mg, 51%). $^1$H NMR (500 MHz, d$_6$-DMSO) δ1.13 (s, 3H), 1.15 (s, 3H), 2.98 (m, 1H), 6.84 (d, J=8.0 Hz, 1H), 6.97 (bs, 1H), 7.62 (s, 1H), 7.67 (d, J=9.0 Hz, 2H), 7.99 (d, J=9.0 Hz, 2H), 8.58 (d, J=8.0 Hz, 1H). MS (ESI) m/z: 394.0621 [M+H]$^+$. HPLC (254 nm): $t_R$=10.86 (82%).

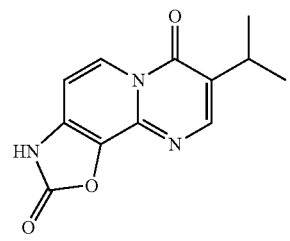

16-1

TABLE 14

Compounds prepared according to Example 15 (Scheme 15)

| Compound | Structure | MW | Proton NMR | Mass Spec |
|---|---|---|---|---|
| 1722 | (structure shown) | 311.4 | $^1$H NMR (400 MHz, d6-DMSO) δ 1.18 (s, 3H), 1.19 (s, 3H), 1.45 (t, J = 7.6 Hz, 3H), 3.88 (d, J = 7.6 Hz, 3H), 6.81 (bs, 1H), 6.88 (d, J = 8.0 Hz, 1H), 8.00 (s, 1H), 8.63 (d, J = 8.0 Hz, 1H). | m/z 312.1 [M + H]$^+$ |

Example 16

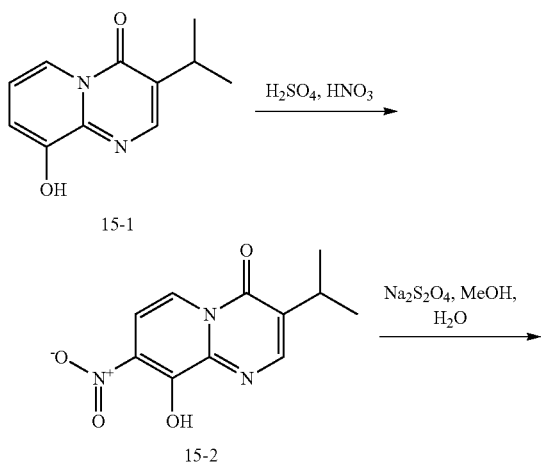

Scheme 16

Fused Oxazole (16-1) (1708)

Carbonyldiimadazole (50 mg, 0.34 mmol) was added to a solution of the aniline 15-3 (50 mg, 0.23 mmol) in THF (1 mL) and heated to reflux for 2 h. The reaction was cooled to room temperature over 1 h and concentrated under reduced pressure to give a yellow solid. The solid was dissolved in dichloromethane and extracted with a 2M aqueous solution of sodium hydroxide (7 mL×3). The combined aqueous layers were taken to pH 5 carefully using concentrated HCl solution, resulting in a white precipitate forming in solution. The precipitate was filtered off and washed with water and air dried to afford the fused oxazole (16-1) PB1708 (28 mg, 50%). $^1$H NMR (400 MHz, d$_6$-DMSO) δ1.22 (s, 3H), 1.23 (s, 3H), 3.09 (m, 1H), 7.31 (d, J=7.6 Hz, 1H), 8.15 (s, 1H), 8.85 (d, J=7.6 Hz, 1H). MS (ESI) m/z: 246.0875 [M+H]$^+$. HPLC (254 nm): $t_R$=7.09 (93%).

Example 17

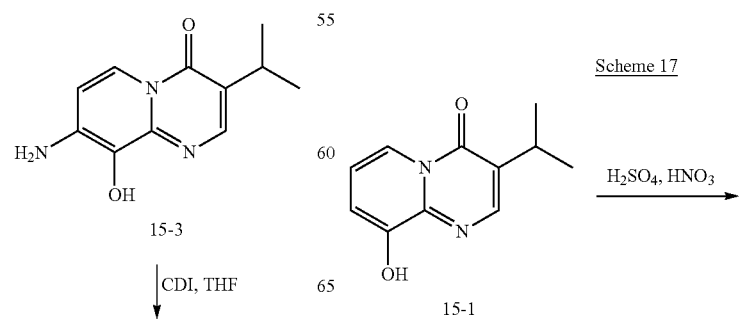

Scheme 17

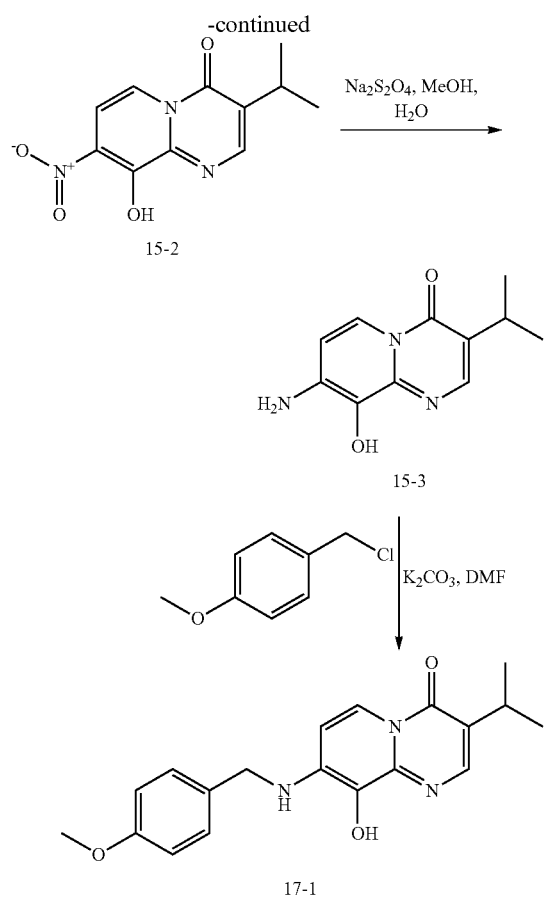

9-Hydroxy-3-isopropyl-8-(4-methoxybenzylamino)-4H-pyrido[1,2-a]pyrimidin-4-one (17-1) (1716)

Potassium carbonate (40 mg, 0.31 mmol) was added to a stirred solution of 4-methoxybenzyl chloride (40 mg, 0.25 mmol) and the aniline 15-3 (50 mg, 0.23 mmol) in DMF (1 mL) and heated at 90° C. for 17 h. The reaction was concentrated to give a dark brown gum that was diluted with ethyl acetate and washed with water (5 mL) and brine (5 mL) and then dried ($Na_2SO_4$). Concentration under reduced pressure gave a brown gum that was purified by flash chromatography on silica (5 g) eluting with a 4% solution of methanol in dichloromethane (400 mL). A yellow gum was isolated and identified as 9-hydroxy-3-isopropyl-8-(4-methoxybenzylamino)-4H-pyrido[1,2-a]pyrimidin-4-one (17-1) 1716 (20 mg, 25%). $^1$H NMR (400 MHz, $d_6$-DMSO) δ1.21 (s, 3H), 1.21 (s, 3H), 2.99 (m, 1H), 3.71 (s, 3H), 5.07 (s, 2H), 6.47 (bs, 1H), 6.79 (d, J=7.6 Hz, 1H), 6.87 (d, J=8.8 Hz, 2H), 7.45 (d, J=8.8 Hz, 2H), 8.07 (s, 1H), 8.54 (d, J=7.6 Hz, 1H). MS (ESI) m/z: 340.1572 [M+H]$^+$. HPLC (300 nm): $t_R$=10.15 (99%).

Example 18—Metallocomplexes

Copper and zinc metal complexes of various 9-hydroxy pyridopyrimidine compounds can be prepared by stirring a solution of the pyridopyrimidine in a solvent together with Cu (II) or Zn (II) chloride. The resulting precipitated product is filtered and dried to afford the desired complexes.

Zinc complex of 9-hydroxy-3-propyl-4H-pyridin[1,2-a]pyrimidin-4-one (1678)

To a stirred solution of 9-hydroxy-3-propyl-4H-pyridin[1,2-a]pyrimidin-4-one (150 mg, 0.75 mmol) in EtOH (75 mL) was added a solution of zinc (II) chloride (100 mg, 0.75 mmol) in $H_2O$ (36 mL). After 10 min, a precipitate formed which was removed by filtration. The mother liquors were left to stand overnight in which time fine white crystals precipitated out of solution. After leaving for a further 7 days, the crystals were filtered off (91 mg) and washed with cold ethanol to provide the desired zinc complex (1678). An X-ray crystal structure was obtained.

TABLE 15

Compounds prepared according to Example 18

| Compound | Structure | MW | Analysis |
|---|---|---|---|
| 1678 | 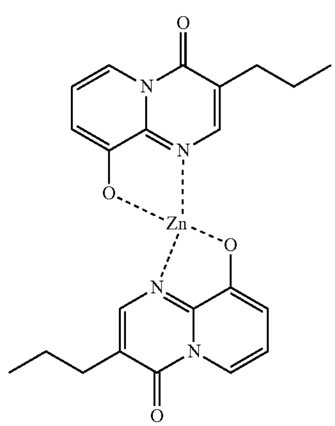 | 473.83 | $^1$H NMR (600 MHz, d6-DMSO) δ 0.91 (t, J = 7.8 Hz, 3H), 1.59 (m, 2h), 2.52 m, 2H), 6.84 (d, J = 7.2 Hz, 1H), 7.22 (t, J = 7.2 Hz, 1H), 8.05 (d, J = 7.2 Hz, 1H), 8.11 (s, 1H). |

TABLE 15-continued
Compounds prepared according to Example 18
| Compound | Structure | MW | Analysis |
|---|---|---|---|
| 1692 | 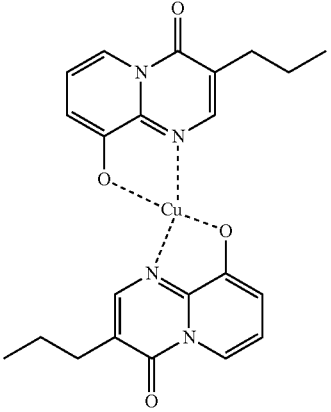 | 472.00 | IR(KBr, cm$^{-1}$): 3447 (coordinated water), 2922 (C—H), 1709 (C=O), 1683, 1618 (C=N), 1538, 1505, 1338, 1289, 1242, 1162, 1141, 1070, 952, 750. |
| 1700 | 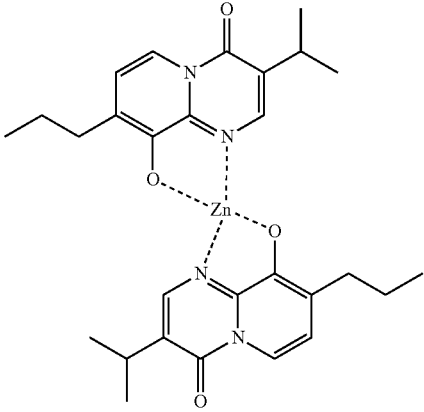 | 558.0 | $^1$H NMR (600 MHz, d6-DMSO) δ 0.96 (t, J = 7.2 Hz, 3H), 1.19 (s, 3H), 1.20 (s, 3H), 1.71 (m, 2H), 2.74 (t, J = 7.2 Hz, 2H), 3.08 (m, 1H), 7.20 (d, J = 6.6 Hz, 1H), 8.04 (d, J = 6.6 Hz, 1H), 8.08 (s, 1H) |
| 1715 | 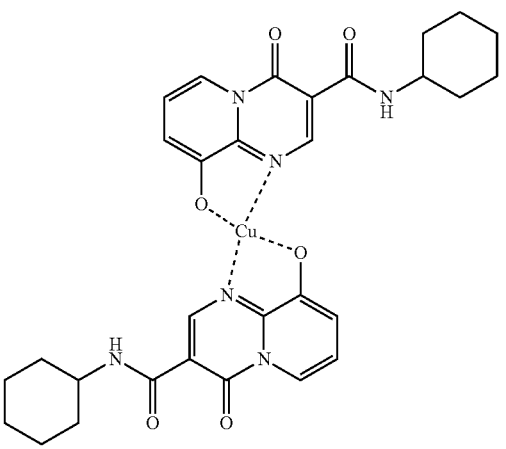 | 636.2 | IR(KBr, cm$^{-1}$): 3441 (coordinated water), 3326 (NH), 2927 (C—H), 2851, 1695 (C=O), 1644. 1613, 1528 (C=N), 1494, 1373, 1320, 1283, 1134, 779, 673. |

TABLE 15-continued
Compounds prepared according to Example 18
| Compound | Structure | MW | Analysis |
|---|---|---|---|
| 1718 | 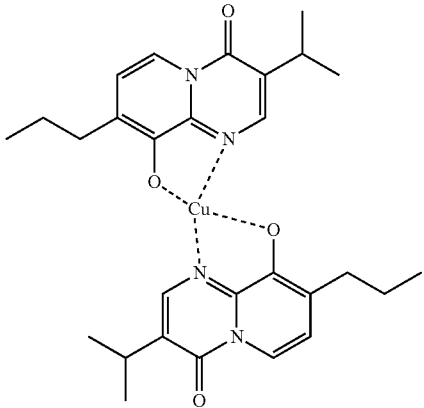 | 554.1 | IR(KBr, cm$^{-1}$): 3441 (coordinated water), 2954 (C—H), 1673 (C=O), 1600 (C=N), 1527. 1515, 1346, 1300, 1246, 1149, 832. |
| 1719 | 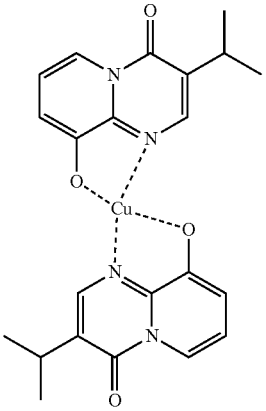 | 470.0 | IR(KBr, cm$^{-1}$): 3441 (coordinated water), 2954 (C—H), 1673 (C=O), 1600 (C=N), 1527. 1515, 1346, 1300, 1246, 1149, 832. |
| 1744 | 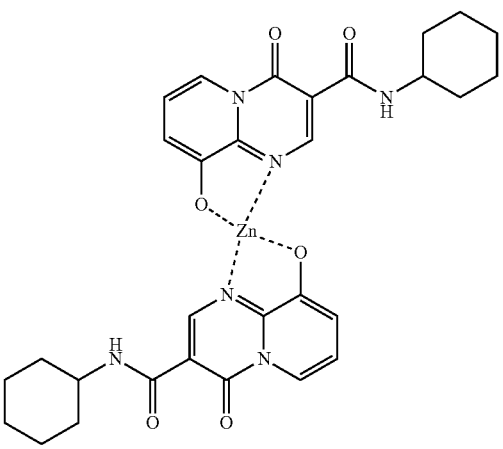 | 638.0 | $^1$H NMR (400 MHz, d6-DMSO) δ 1.31 (m, 6H), 1.65 (m, 1H), 1.60 (m, 2H), 1.84 (m, 2H), 3.80 (m, 1H), 7.15 (d, J = 5.2 Hz, 1H), 7.43 (t, J = 7.2 Hz, 1H), 8.24 (d, J = 7.2 Hz), 8.82 (s, 1H), 8.99 (d, J = 7.2 Hz, 1H). |

TABLE 15-continued
Compounds prepared according to Example 18
| Compound | Structure | MW | Analysis |
|---|---|---|---|
| 1745 | 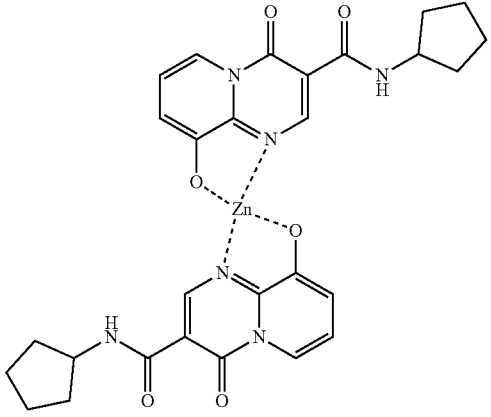 | 610.0 | $^1$H NMR (500 MHz, d6-DMSO) δ 1.47 (m, 2H), 1.59 (m, 2H), 1.91 (m, 2H), 4.24 (m, 1H), 7.15 (d, J = 8.0 Hz, 1H), 7.44 (t, J = 6.0 Hz, 1H), 8.23 (m, 1H), 8.85 (s, 1H), 8.93 (d, J = 8.0 Hz, 1H). m/z 609.1 [M + H]$^+$ |
| 1748 | 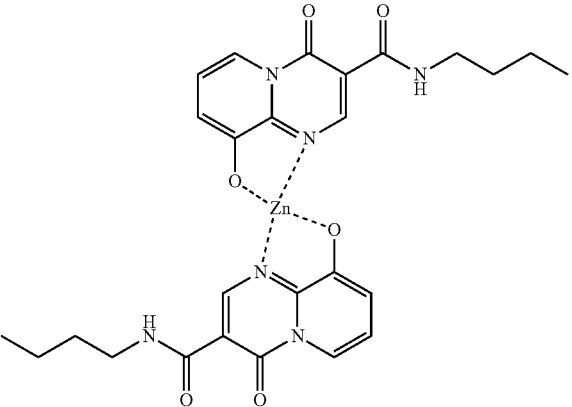 | 586.0 | $^1$H NMR (500 MHz, d6-DMSO) δ 0.90 (t, J = 6.0 Hz, 3H), 1.33 (m, 2H), 1.49 (m, 2H), 1.51 (m, 2H), 3.36 (m, 2H, obscured), 7.15 (d, J = 5.6 Hz, 1H), 7.44 (t, J = 5.6 Hz, 1H), 8.24 (d, J = 5.6 Hz, 1H), 8.87 (s, 1H), 8.93 (m, 1H) |
Example 19
Scheme 19
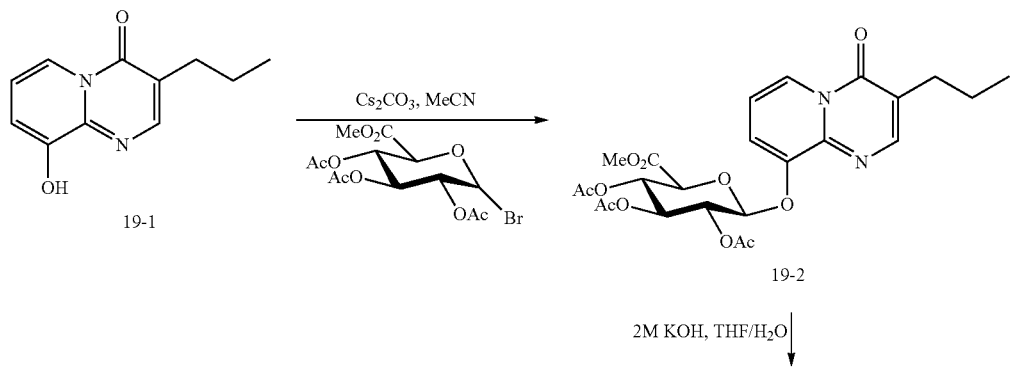
2M KOH, THF/H$_2$O

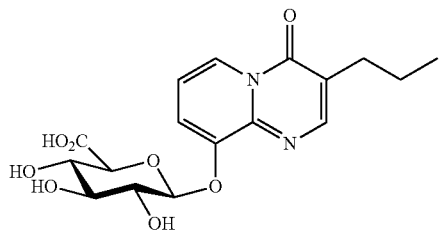
PB1761

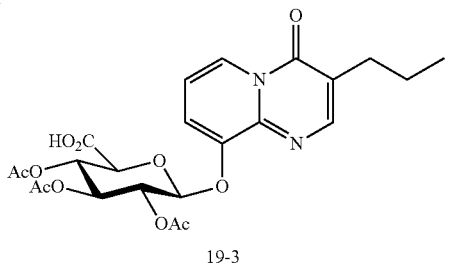
19-3

Compound 1761

(2S,3S,4S,5R,6S)-2-(Methoxycarbonyl)-6-(4-oxo-3-propyl-4H-pyrido[1,2-a]pyrimidin-9-yloxy)tetrahydro-2H-pyran-3,4,5-triyl triacetate (19-2)

Caesium carbonate (0.65 g, 2.0 mmol) was added to a stirred solution of 9-hydroxy-3-propyl-4H-pyridin[1,2-a]pyrimidin-4-one (19-1) (0.13 g, 0.67 mmol) and (3R,4S,5S,6S)-2-bromo-6-(methoxycarbonyl)tetrahydro-2H-pyran-3,4,5-triyl triacetate (0.80 g, 2.0 mmol) in acetonitrile (7.0 mL). The mixture was stirred at room temperature under an argon atmosphere for 6 days. Water (5.0 mL) was added to the reaction which was then extracted with dichloromethane (10 mL×3). The organic layers were dried (sodium sulphate) and concentrated under reduced pressure to give a brown gum. Purification by chromatography on silica (10 g), eluting with a 20:1 solution of dichloromethane/methanol afforded (2S,3S,4S,5R,6S)-2-(methoxycarbonyl)-6-(4-oxo-3-propyl-4H-pyrido[1,2-a]pyrimidin-9-yloxy)tetrahydro-2H-pyran-3,4,5-triyl triacetate (19-2) as a cream solid (0.30 g, 86%). $^1$H NMR (600 MHz, CDCl$_3$) δ 0.92 (t, J=7.2 Hz, 3H), 0.62 (m, 2H), 1.98 (s, 3H), 2.00 (s, 3H), 2.05 (s, 3H), 2.56 (m, 2H), 3.66 (s, 3H), 4.07 (d, J=9.0 Hz, 1H), 5.30-5.33 (m, 3H), 5.43 (d, J=6.6 Hz, 1H), 6.94 (t, J=7.2 Hz, 1H), 7.36 (d, J=1.2 Hz, 1H), 8.09 (s, 1H), 8.76 (dd, J=1.2, 7.2 Hz, 1H).

(2S,3S,4S,5R,6S)-3,4,5-Triacetoxy-6-(4-oxo-3-propyl-4H-pyrido[1,2-a]pyrimidin-9-yloxy)tetrahydro-2H-pyran-2-carboxylic acid (19-3)

A 2M aqueous solution of potassium carbonate (0.29 mL, 0.58 mmol) was added to a solution of A (0.05 g, 0.10 mmol) dissolved in THF/water (4:1, 8 mL) at 0° C. The reaction was stirred at this temperature for 5 min then warmed to room temperature and stirred for 2 h. The reaction was then neutralised with Amberlite IRA (H+) resin and filtered. The resin was washed with methanol (5 mL×2) and the filtrates were concentrated. Chromatography (silica, 20 g), eluting with a mixture of ethyl acetate, methanol and water (7:2:1, 300 mL) afforded (2S,3S,4S,5R,6S)-3,4,5-triacetoxy-6-(4-oxo-3-propyl-4H-pyrido[1,2-a]pyrimidin-9-yloxy)tetrahydro-2H-pyran-2-carboxylic acid (19-3) as cream, gummy solid (78 mg, 74%). $^1$H NMR (600 MHz, d$_6$-DMSO) δ 0.89 (t, J=7.8 Hz, 3H), 1.59 (m, 2H), 1.90 (s, 3H), 1.98 (s, 3H), 1.99 (s, 3H), 2.50 (m, 2H), 3.98 (d, J=10.2 Hz, 1H), 5.09 (t, J=9.6 Hz, 1H), 5.13 (t, J=7.8 Hz, 1H), 5.26 (t, J=9.6 Hz, 1H), 5.58 (d, J=8.4 Hz, 1H), 7.25 (t, J=7.2 Hz, 1H), 7.48 (d, J=7.8 Hz, 1H), 8.23 (s, 1H), 8.66 (d, J=7.2 Hz, 1H).

(2S,3S,4S,5R, 6S)-3,4,5-Trihydroxy-6-(4-oxo-3-propyl-4H-pyrido[1,2-a]pyrimidin-9-yloxy)tetrahydro-2H-pyran-2-carboxylic acid (1761)

Triethylamine (0.21 mL, 1.50 mmol) was added to a stirred solution of the acid 19-3 (0.15 g, 0.30 mmol) in methanol (1.5 mL) and headed under argon for 17 h. The reaction was cooled in an ice bath and the subsequent white precipitate was filtered off and washed with minimal cold methanol. (2S,3S,4S,5R,6S)-3,4,5-Trihydroxy-6-(4-oxo-3-propyl-4H-pyrido[1,2-a]pyrimidin-9-yloxy)tetrahydro-2H-pyran-2-carboxylic acid (1761) was isolated as a white solid (54 mg, 47%). $^1$H NMR (600 MHz, d$_6$-DMSO) δ 0.90 (t, J=7.2 Hz, 3H), 1.59 (m, 2H), 2.50 (m, 2H), 3.12 (t, J=9.0 Hz, 1H), 3.26-3.31 (m, 2H), 3.44 (d, J=9.6 Hz, 1H), 5.02 (bs, 1H), 5.06 (d, J=7.8 Hz, 1H), 5.41 (d, J=5.4 Hz, 1H), 7.22 (t, J=7.8 Hz, 1H), 7.42 (d, J=7.8 Hz, 1H), 8.23 (s, 1H), 8.61 (d, J=6.6 Hz, 1H). 13C NMR (150 MHz, d$_6$-DMSO) δ 14.11, 21.75, 30.20, 72.41, 73.38, 74.01, 77.34, 101.05, 115.59, 116.61, 117.81, 119.92, 144.80, 150.10, 151.48, 157.85, 171.22. MS (ESI) m/z: 381.1302 [M+H]$^+$. HPLC (300 nm): $t_R$=4.99 (97%).

Example 20

Scheme 20

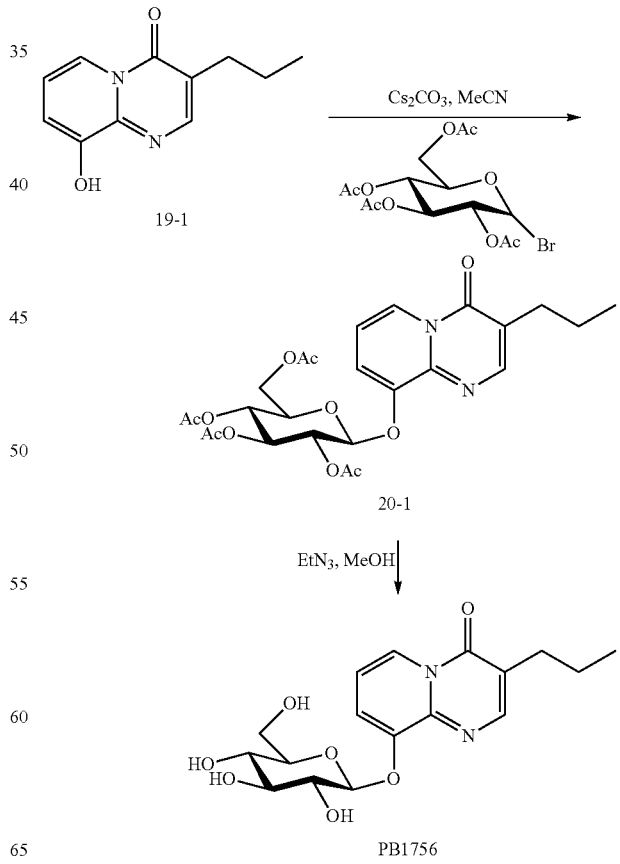
PB1756

Compound 1756 (Glycoside of 9-hydroxy-3-propyl-4H-pyridin[1,2-a]pyrimidin-4-one 19-1)

(2R,3R,4S,5R,6S)-2-(acetoxymethyl)-6-(4-oxo-3-propyl-4H-pyrido[1,2-a]pyrimidin-9-yloxy)tetrahydro-2H-pyran-3,4,5-triyl triacetate (20-1)

Caesium carbonate (2.4 g, 7.3 mmol) was added to a stirred solution of 9-hydroxy-3-propyl-4H-pyridin[1,2-a]pyrimidin-4-one (19-1) (0.50 g, 2.5 mmol) and (2R,3S,4S,5R)-2-(acetoxymethyl)-4,6-dihydroxytetrahydro-2H-pyran-3,5-diyl diacetate (3.0 g, 7.3 mmol) in acetonitrile (24.0 mL). The mixture was stirred at room temperature under an argon atmosphere for 6 days. Water (30.0 mL) was added to the reaction which was then extracted with dichloromethane (10 mL×3). The organic layers were dried (sodium sulphate) and concentrated under reduced pressure to give a brown oil. Purification by chromatography on silica (40 g), eluting with a 20:1 solution of dichloromethane/methanol (500 mL) afforded 2R,3R,4S,5R,6S)-2-(acetoxymethyl)-6-(4-oxo-3-propyl-4H-pyrido[1,2-a]pyrimidin-9-yloxy)tetrahydro-2H-pyran-3,4,5-triyl triacetate (20-1) as a cream solid (0.98 g, 75%). $^1$H NMR (600 MHz, CDCl$_3$) δ 0.91 (t, J=7.2 Hz, 3H), 0.62 (m, 2H), 1.97 (s, 6H), 2.00 (s, 3H), 2.05 (s, 3H), 2.56 (m, 2H), 3.75 (m, 1H), 4.11 (dd, J=2.4, 12.0 Hz, 1H), 4.20 (dd, J=4.8, 12.6 Hz, 1H), 5.13 (m, 1H), 5.31 (m, 3H), 6.93 (t, J=7.8 Hz, 1H), 7.29 (dd, J=1.2, 7.2 Hz, 1H), 8.11 (s, 1H), 8.76 (dd, J=1.2, 7.2 Hz, 1H). $^{13}$C NMR (150 MHz, CDCl$_3$) δ 14.52, 21.23, 21.28, 21.34, 21.47, 22.41, 31.05, 62.38, 68.85, 71.64, 72.95, 72.97, 100.66, 114.28, 120.10, 121.31, 123.34, 149.42, 152.08, 158.72, 170.02, 170.21, 170.87, 171.82.

3-Propyl-9-((2S,3R,4S,5S,6R)-3,4,5-trihydroxy-6-(hydroxymethyl)tetrahydro-2H-pyran-2-yloxy)-4H-pyrido[1,2-a]pyrimidin-4-one (1756)

Triethylamine (0.48 mL, 3.50 mmol) was added to a stirred solution of the acetate 20-1 (0.37 g, 0.69 mmol) in methanol (7.0 mL) and headed under argon for 17 h. In this time a precipitate was evident in the reaction mixture. The reaction was cooled in an ice bath and the white precipitate was filtered off and washed with minimal cold methanol. The solid was recrystallised from methanol to yield 3-propyl-9-((2S,3R,4S,5S,6R)-3,4,5-trihydroxy-6-(hydroxymethyl)tetrahydro-2H-pyran-2-yloxy)-4H-pyrido[1,2-a]pyrimidin-4-one (1756) as a white solid (151 mg, 60%). $^1$H NMR (600 MHz, d$_6$-DMSO) δ 0.89 (t, J=7.2 Hz, 3H), 1.58 (m, 2H), 2.53 (m, 2H), 3.16 (m, 1H), 3.32 (m, 2H), 3.46 (m, 1H), 3.68 (m, 1H), 4.56 (m, 1H), 5.06 (d, J=4.8 Hz, 1H), 5.11-5.12 (m, 2H), 5.51 (d, J=4.8 Hz, 1H), 7.22 (d, J=6.6 Hz, 1H), 7.43 (d, J=7.2 Hz, 1H), 8.22 (s, 1H), 8.61 (d, J=6.6 Hz, 1H). $^{13}$C NMR (150 MHz, d$_6$-DMSO) δ14.11, 21.76, 30.18, 61.05, 69.06, 73.46, 77.16, 77.73, 100.78, 115.52, 116.19, 117.94, 119.96, 142.75, 144.80, 149.84, 151.39, 157.63. MS (ESI) m/z: 367.1509 [M+H]$^+$. HPLC (300 nm): t$_R$=4.

TABLE 16

Compound prepared according to Example 20

| Compound | Structure | MW | Analysis |
|---|---|---|---|
| 1862 | 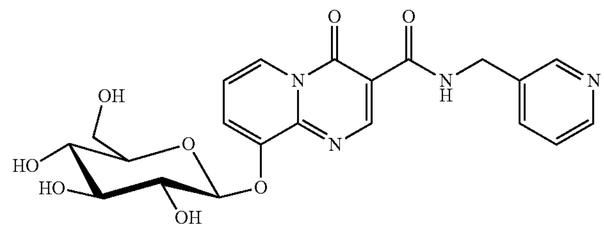 | 458.42 | |

Example 21—Assessment of Properties Compounds

The following Assays were used to assess the properties of the compounds to determine their suitability for use in the methods of the present invention.

Assay 1. Hydrogen Peroxide Assay $H_2O_2$ is a strong oxidizer and a highly reactive oxygen species that is known to be toxic to surrounding proteins and organelles, inhibiting their function. The hydrogen peroxide ($H_2O_2$) inhibition assay is a fluorescence assay which evaluates the ability of a test compound to inhibit the generation of $H_2O_2$ by the presence of copper and a reducing substrate, being either dopamine or ascorbic acid. In the assay, copper in the form of CuCl$_3$ is allowed to react with ascorbic acid or dopamine by incubating for 1 hr at 37° C. in the presence of the fluorescing compound DCF and horseradish peroxidase. $H_2O_2$ generated by the system is assessed by measuring the specific fluorescence profile at the excitation and emission wavelengths of 485 and 530 nm respectively, in the presence of test compound. Test compounds were dissolved in DMSO and tested at concentrations of 0.4 μM. Test compounds are ranked according to their capacity to inhibit $H_2O_2$ generated by the system where lower values reflect greater ability to inhibit $H_2O_2$ production.

Assay 2. Physiochemical Properties cLog P Values

Theoretical Log P values were determined using the ACD Log P software. The values quoted have been calculated from an untrained database and refer to the unionised species.

E Log D

Effective Log D values were measured using a chromatographic method employing a SUPELCOSIL LC-ABZ column using an octanol saturated mobile phase at pH 7.4. See F. Lombardo et al, J. Med. Chem. 2000, 43, 2922-2928.

The following table provides the properties and structures of compounds of the present invention. The properties of the HCl salt were tested for those compounds in the table where the MW of the HCl salt is provided.

TABLE 17

| Compound | H₂O₂ IC₅₀ (µM)$^a$ Fe-ASC % Fe-DA % (cf. 0.4 uM Fe/Asc or Fe/DA) cf. CQ (CQ = 100%) | Parent MW/PSA | ClogP |
|---|---|---|---|
| 1235 | 0.29 86% ASC | 238.68 | 2.43 |
| 1394 | 0.72 96% ASC | 317.38 | 3.56 |
| 1398 | 1.29 39% ASC | 206.20 | |
| 1399 | 0.23 30% ASC | 205.21 | −0.16 |
| 1400 | 0.33 32% ASC | Parent: 219.24 HCl Salt: 255.69 | 0.37 |
| 1401 | 0.42 55% ASC | Parent: 219.24 HCl Salt: 255.69 | 0.31 |
| 1402 | 1.68 36% ASC | 288.35 HCl salt 324.81 | 1.31 |
| 1403 | 1.7 49% ASC | 259.31 HCl salt 295.76 | 1.50 |
| 1404 | 0.28 37% ASC | 243.267 HCl salt 279.72 | 0.91 |
| 1405 | 0.29 35% ASC | 247.3 HCl salt 283.75 | 1.43 |
| 1406 | 1.14 | 315.75 HCl salt 352.21 | 1.71 |
| 1407 | 0.15 31% ASC | Parent: 233.27 HCl Salt: 269.72 | 0.90 |
| 1408 | 0.43 | Parent: 247.29 HCl Salt: 283.74 | 1.30 |
| 1409 | 0.14 | Parent: 299.30 HCl Salt: 335.75 | 1.14 |
| 1410 | 0.43 62% ASC | Parent: 303.40 HCl Salt: 339.85 | 3.55 |
| 1411 | 0.33 36% ASC | Parent: 245.28 HCl Salt: 281.73 | 0.82 |
| 1412 | 0.13 29% ASC | Parent: 318.37 HCl salt: 391.29 | 0.43 |
| 1413 | 0.19 42% ASC | Parent: 261.32 HCl Salt: 297.77 | 1.96 |
| 1414 | <0.1 29% ASC | Parent: 282.3 HCl Salt: 318.74 | −0.50 |
| 1415 | <0.1 34% ASC | Parent: 296.33 HCl Salt: 332.77 | 0.44 |
| 1416 | 0.1 52% ASC | Parent: 282.2 HCl Salt: 318.76 | −0.50 |
| 1417 | 0.13 29% ASC | Parent: 288.35 HCl salt: 361.27 | 0.86 |
| 1418 | 0.24 30% ASC | Parent: 304.35 HCl Salt: 377.27 | 0.21 |
| 1422 | 0.68 63% ASC | 275.31 | 1.97 |
| 1423 | 0.38 45% ASC | 247.26 | 0.91 |
| 1424 | 0.8 48% ASC | 219.2452 HCl salt: 243.69 | 0.31 |
| 1425 | 0.34 Cu 212% ASC Zn 69% ASC 76% | 261.28 | 1.31 |
| 1426 | 0.32 Cu 212% ASC Zn 121% ASC 62% | 302.33 | 0.90 |
| 1427 | 0.18 Cu 212% ASC Zn 61% ASC 74% | 310.31 | 0.45 |
| 1428 | 0.43 Cu 212% ASC Zn 74% ASC 75% | 259.27 | 0.83 |
| 1429 | 0.39 Cu 54% ASC Zn 57% ASC 148% | 329.74 | 2.53 |
| 1430 | 2.28 Cu 184% ASC Zn 98% ASC 44% | 204.23 | 1.95 |
| 1431 | 0.44 71% ASC 70% | 325.33 | 1.74 |
| 1432 | 0.41 65% ASC 66% | 339.31 | 1.79 |
| 1433 | 0.39 152% ASC 73% | 223.23 | 0.38 |
| 1434 | 3.16 135% ASC 95% | 190.2 | 1.42 |
| 1435 | 0.23 133% ASC 90% | 259.31 HCl salt: 295.75 | 1.314 |
| 1436 | 0.21 190% ASC 101% | 273.29 | 1.32 |
| 1437 | 0.47 71% ASC 71% | 331.28 | 2.11 |
| 1438 | 0.24 143% ASC 47% | 275.35 HCl salt: 311.8 | 2.487 |
| 1439 | >10 156% ASC 68% | 247.3 HCl salt: 283.75 | 1.366 |
| 1440 | 0.69 66% ASC 48% | 289.34 | 2.50 |
| 1441 | 0.47 >224% ASC 55% | 263.26 | 0.05 |
| 1442 | 0.24 128% ASC 58% | 281.32 | 1.0 |
| 1443 | 0.25 116% ASC 52% | 347.8 | 0.92 |
| 1444 | 0.35 105% ASC 53% | 303.27 | 2.05 |
| 1445 | <0.1 176% ASC 45% | 219.2 | −0.147 |
| 1446 | 0.34 218% ASC 56% | 296.29 | 0.32 |
| 1447 | 0.24 112% ASC 52% | 296.29 | 0.35 |
| 1448 | 0.46 137% ASC 66% | 268.28 | |
| 1449 | 0.47 144% ASC 71% | 267.29 | |
| 1450 | 0.38 126% ASC 55% | 296.29 | 0.35 |
| 1451 | 0.58 136% ASC 67% | 285.27 | 1.87 |

TABLE 17-continued

| Compound | H$_2$O$_2$ IC$_{50}$ (μM)$^a$ Fe-ASC % Fe-DA % (cf. 0.4 uM Fe/Asc or Fe/DA) cf. CQ (CQ = 100%) | Parent MW/PSA | ClogP |
|---|---|---|---|
| 1452 | 0.54 60% ASC 49% | 364.19 | 3.25 |
| 1453 | 0.34 79% ASC 59% | 363.30 | 2.70 |
| 1454 | 1 65% ASC 46% | 331.28 | 2.04 |
| 1455 | 0.35 82% ASC 47% | 295.34 | 1.88 |
| 1456 | 0.39 122% ASC 58% | 273.34 | 1.88 |
| 1457 | 0.39 127% 61% | 350.21 | 2.43 |
| 1458 | 0.58 137% ASC 43% | 287.35 | 2.49 |
| 1459 | 0.33 110% ASC 48% | 317.30 HCl salt: 353.75 | 1.29 |
| 1460 | 0.44 92% ASC 29% | 287.32 | 1.88 |
| 1461 | 0.49 59% ASC 57% | 301.35 | 2.50 |
| 1462 | 0.46 72% ASC 54% | 305.38 | 3.03 |
| 1463 | 0.59 158% ASC 73% | 341.37 | 0.658 |
| 1464 | 0.47 135% ASC 47% | 365.31 HCl salt: 401.76 | 2.03 |
| 1466 | 0.34 >234% ASC 47% | 233.27 HCl salt: 269.72 | 0.807 |
| 1467 | 0.44 74% ASC 42% | 313.33 | 1.642 |
| 1468 | 0.21 169% ASC 39% | 287.36 HCl salt: 323.81 | 2.372 |
| 1469 | 0.5 63% ASC 43% | 329.789 | 2.212 |
| 1470 | 0.35 >234% ASC 38% | 247.299 | 1.399 |
| 1471 | 0.3 125% ASC 62% | 273.34 HCl salt: 309.79 | 2.000 |
| 1476 | 0.23 122% ASC 46% | 310.36 | 0.908 |
| 1478 | 3.12 198% ASC 75% | 295.34 | 1.49 |
| 1479 | 0.46 147% ASC 42% | 313.33 HCl salt 349.78 | 2.21 |
| 1485 | 0.53 159% ASC 57% | 261.33 HCl salt: 297.78 | 1.895 |
| 1488 | 1.95 114% ASC 69% | 283.12 | 2.55 |
| 1490 | 0.4 178% ASC 55% | 261.326 HCl salt: 297.776 | 1.865 |
| 1491 | 0.3 >222% ASC 48% | 257.294 HCl salt: 293.74 | 1.4072 |
| 1500 | 0.36 171% ASC 42% | 327.36 HCl salt: 363.81 | 2.718 |
| 1503 | 0.23 204% ASC 42% | 301.38 HCl salt: 337.84 | 2.991 |
| 1504 | 0.31 160% ASC 33% | 310.35 2HCl salt: 383.26 | 0.9412 |
| 1506 | >10 161% ASC 48% | 273.34 HCl salt: 309.79 | 2.02025 |
| 1508 | 0.17 148% ASC 32% | 287.357 HCl salt: 323.807 | 2.519 |
| 1515 | 1 103% ASC 54% | 368.404 HCl salt: 441.305 | 2.647 |
| 1516 | 0.3 102% ASC 52% | 313.326 HCl salt: 349.776 | 2.219 |
| 1517 | 0.35 105% ASC 55% | 313.326 HCl salt: 349.776 | 2.219 |
| 1518 | 0.58 84% ASC 49% | 329.781 HCl salt: 366.23 | 2.789 |
| 1519 | 0.35 100% ASC 47% | 343.807 HCl salt: 380.26 | 3.288 |
| 1521 | >10 123% ASC 50% | 287.357 HCl salt: 323.807 | 2.339 |
| 1522- | 0.44 156% ASC 47% | 382.431 HCl salt: 455.341 | 3.146 |
| 1523 | 0.7 135% ASC 49% | 301.383 HCl salt: 337.833 | 2.838 |
| 1525 | 0.32 105% ASC 46% | 327.36 HCl salt: 363.81 | 2.718 |
| 1527 | 0.33 133% ASC 64% | 327.36 HCl salt: 363.81 | 2.718 |
| 1531 | 1.48 | 296.13 HCl salt: 332.77 | 1.894 |
| 1532 | 0.9 | 259.26 | −0.145 |
| 1533 | 1.19 | 273.29 | 0.414 |
| 1591 | | 220.22 | 0.66 |
| 1595 | | 421.9 | 3.71 |
| 1596 | | 281.31 | 2.00 |
| 1597 | | 326.39 | 3.07 |
| 1598 | | 312.37 | |
| 1599 | | 283.12 | 2.91 |
| 1600 | | 299.32 | 1.42 |
| 1601 | | 312.37 | 2.67 |
| 1602 | | 284.31 | 1.81 |
| 1603 | | 299.32 | 1.55 |
| 1604 | | 253.68 | 1.03 |
| 1605 | | 290.31 | 1.99 |
| 1606 | | 361.4 | 2.80 |

TABLE 17-continued

| Compound | Properties $H_2O_2$ IC$_{50}$ (μM)$^a$ Fe-ASC % Fe-DA % (cf. 0.4 uM Fe/Asc or Fe/DA) cf. CQ (CQ = 100%) | Parent MW/PSA | ClogP |
|---|---|---|---|
| 1607 | | 238.67 | 2.76 |
| 1608 | | 281.74 | 2.09 |
| 1609 | | 347.7 | 2.95 |
| 1610 | | 333.74 | 1.83 |
| 1611 | | 364.57 | 3.54 |
| 1612 | | 384.64 | 3.15 |
| 1613 | | 232.29 | 3.00 |
| 1614 | | 267.71 | 1.63 |
| 1615 | | 361.4 | 2.93 |
| 1616 | | 361.4 | 3.23 |
| 1617 | | 339.4 | 2.93 |
| 1618 | | 402.85 2HCl 475.77 | 3.37 |
| 1619 | | 228.25 | 1.39 |
| 1620 | | 232.28 | 3.06 |
| 1621 | | 244.30 | 3.09 |
| 1622 | | 278.73 | 3.82 |
| 1623 | | 230.26 | 2.54 |
| 1624 | | 264.71 | 3.26 |
| 1625 | | 228.25 | 1.39 |
| 1626 | | 339.39 | 2.64 |
| 1627 | | 287.36 | 2.32 |
| 1628 | | 344.41 | 1.67 |
| 1629 | Cu 204% ASC Zn 130% ASC | 315.75 | 2.60 |
| 1630 | Cu 213% ASC Zn 129% ASC | 333.77 | 2.02 |
| 1631 | Cu 248% ASC Zn 101% ASC | 261.33 | 1.82 |
| 1632 | Cu 228% ASC Zn 106% ASC | 261.33 | 1.69 |
| 1633 | Cu 17% ASC Zn 140% ASC | 284.32 | 1.61 |
| 1634 | | 295.72 | 0.95 |
| 1635 | | 279.72 HCl MW: 316.18 | 1.67 |
| 1636 | | 420.84 | 3.52 |
| 1637 | | 453.75 | 4.66 |
| 1638 | | 414.89 | 3.15 |
| 1639 | | 298.31 | 3.77 |
| 1640 | | 329.29 | 2.23 |
| 1641 | | 281.31 | 2.13 |
| 1642 | | 301.38 | 2.89 |
| 1643 | | 238.67 | 2.63 |
| 1644 | | 421.28 | 3.03 |
| 1645 | | 303.36 | 1.73 |
| 1646 | | 234.1 | 0.97 |
| 1647 | | 289.37 | 2.87 |
| 1648 | | 298.34 | 1.67 |
| 1649 | | 248.23 | 1.46 |
| 1650 | | 282.25 | 2.61 |
| 1651 | | 298.34 | 1.54 |
| 1652 | | 286.35 | 3.14 |
| 1653 | | 270.28 | 2.67 |
| 1654 | | 284.31 | 3.37 |
| 1655 | | 281.31 | 2.00 |
| 1656 | | 303.36 | 1.60 |
| 1657 | | 356.38 | 0.94 |
| 1658 | | 318.37 | 1.22 |
| 1659 | | 298.31 | 3.64 |
| 1660 | | 355.36 | 3.17 |
| 1661 | | 327.33 | 2.2 |
| 1662 | | 238.65 | 2.68 |
| 1663 | | 224.64 | 2.15 |
| 1664 | | 339.35 | 2.39 |
| 1665 | | 350.54 | 2.92 |
| 1666 | | 330.11 | 2.74 |
| 1667 | | 266.72 | 3.73 |
| 1668 | | 348.32 | 4.38 |
| 1669 | | 330.38 | 1.10 |
| 1670 | | 307.78 HCl salt MW: 344.24 | |
| 1671 | | 296.36 | 3.72 |
| 1672 | | 300.74 | 3.71 |
| 1673 | | 319.74 | 1.407 |
| 1674 | | 252.27 | 2.54 |
| 1678 | | 473.83 | 3.57 |
| 1679 | | 275.35 | 2.56 |
| 1680 | | 281.31 | 2.13 |
| 1681 | | 316.30 | 3.91 |
| 1682 | | 332.40 | 1.75 |
| 1683 | | 323.39 | |
| 1684 | | 372.2 | |
| 1685 | | 220.2 | 0.38 |
| 1686 | | 254.67 | 1.11 |
| 1687 | | 280.75 | 3.61 |
| 1688 | | 392.62 | 4.51 |
| 1689 | | 434.70 | 5.51 |
| 1690 | | 343.81 | 3.58 |
| 1691 | | 277.32 | 0.16 |
| 1692 | | 472.00 | |
| 1698 | | 212.63 | 0.969 |
| 1699 | | 398.89 | 2.42 |
| 1700 | | 557.99 | 6.43 |
| 1701 | | 254.67 | 1.39 |
| 1703 | | 283.67 | 2.35 |
| 1704 | | 219.24 | 1.74 |
| 1708 | | 245.23 | 0.81 |
| 1710 | | 291.3 | 0.79 |
| 1711 | | 310.31 | 0.95 |
| 1712 | | 370.38 | 1.75 |
| 1713 | | 373.88 | 0.98 |
| 1714 | | 357.88 | 2.87 |
| 1715 | | 636.16 | 2.81 |
| 1716 | | 339.39 | 3.53 |
| 1717 | | 393.84 | 3.56 |
| 1718 | | 554.14 | 6.22 |
| 1719 | | 469.98 | 3.11 |
| 1720 | | HCl salt MW: 420.38 383.92 | 3.52 |
| 1721 | | HCl salt MW: 429.34 392.88 | 1.97 |
| 1722 | | 311.36 | 1.71 |
| 1723 | | 414.41 | 3.62 |
| 1724 | | 402.41 | 1.11 |
| 1744 | | 644.0 | |
| 1745 | | 612.0 | |
| 1748 | | 585.95 | |
| 1756 | | 366.37 | 0.054 |
| 1761 | | 380.35 | −0.42 |
| 1862 | | 458.42 | −1.61 |

REFERENCES

Bush A I, Goldstein L E. Specific metal-catalysed protein oxidation reactions in chronic degenerative disorders of ageing: focus on Alzheimer's disease and age-related cataracts. Novartis Found Symp. 2001; 235:26-38; discussion 38-43.

It is to be understood that, if any prior art publication is referred to herein, such reference does not constitute an admission that the publication forms a part of the common general knowledge in the art, in Australia or any other country.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The claims defining the invention are as follows:
1. A compound of formula Ic:

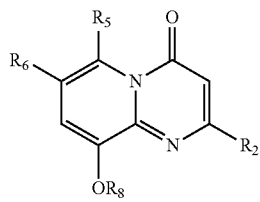

in which
R$^2$ is (CH$_2$)$_n$NR$^9$R$^{10}$, C$_{1-4}$alkyl optionally interrupted with O— or (CH$_2$)$_n$SC=SNR$^9$R$^{10}$;
R$^5$ is H or C$_{1-4}$ alkyl;
R$^6$ is H, halo, (CH$_2$)$_n$ 5 or 6 membered heterocyclyl in which the heterocyclyl group is optionally substituted or C$_{2-4}$ alkynyl; provided that one of R$^5$ and R$^6$ is not hydrogen;
R$^8$ is H, SO$_2$ aryl in which the aryl group is optionally substituted, C$_{1-4}$ alkyl or (CH$_2$)$_n$ aryl; or
R$^9$ and R$^{10}$ together with the nitrogen atom to which they are attached form a 5 or 6 membered heterocyclyl in which the heterocyclyl group is optionally substituted;
n is 0, 1, 2 or 3;
wherein optional substituents are selected from C$_{1-6}$ alkyl, C$_{3-6}$ cycloalkyl, C$_{2-6}$ alkenyl, C$_{2-6}$ alkynyl, aryl, heterocyclyl, halo, haloC$_{1-6}$alkyl, CF$_3$, haloC$_{3-6}$cycloalkyl, haloC$_{2-6}$alkenyl, haloC$_{2-6}$alkynyl, haloaryl, haloheterocycylyl, hydroxy, C$_{1-6}$ alkoxy, OCF$_3$, C$_{2-6}$alkenyloxy, C$_{2-6}$ alkynyloxy, aryloxy, heterocyclyloxy, carboxy, haloC$_{1-6}$alkoxy, haloC$_{2-6}$alkenyloxy, haloC$_{2-6}$alkynyloxy, haloaryloxy, nitro, nitroC$_{1-6}$alkyl, nitroC$_{2-6}$alkenyl, nitroaryl, nitroheterocyclyl, azido, amino, C$_{1-6}$alkylamino, C$_{2-6}$alkenylamino, C$_{2-6}$alkynylamino, arylamino, heterocyclylamino acyl, C$_{1-6}$alkylacyl, C$_{2-6}$alkenylacyl, C$_{2-6}$alkynylacyl, arylacyl, heterocyclylacyl, acylamino, acyloxy, aldehydo, C$_{1-6}$alkylsulphonyl, arylsulphonyl, C$_{1-6}$alkylsulphonylamino, arylsulphonylamino, C$_{1-6}$alkylsulphonyloxy, arylsulphonyloxy, C$_{1-6}$alkylsulphenyl, C$_{2-6}$alklysulphenyl, arylsulphenyl, carboalkoxy, carboaryloxy, mercapto, C$_{1-6}$alkylthio, arylthio, acylthio and cyano;
each 5 or 6 membered heterocyclyl group may have 1, 2, 3 or 4 heteroatoms selected from O, S and N and may be saturated, unsaturated or aromatic;
or a pharmaceutically acceptable salt, stereoisomer or geometric isomer thereof.

2. A compound according to claim 1 which is a compound of formula Ic wherein R$^2$ is (CH$_2$)$_n$NR$^9$R$^{10}$, C$_{1-4}$alkyl optionally interrupted with O or (CH$_2$)$_n$SC=SNR$^9$R$^{10}$; R$^5$ is H or C$_{1-4}$alkyl; and R$^6$ is halo.

3. A compound according to claim 2 wherein R$^5$ is methyl and/or R$^6$ is chloro.

4. A compound of according to claim 1 which is selected from:

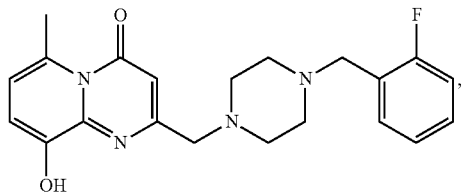

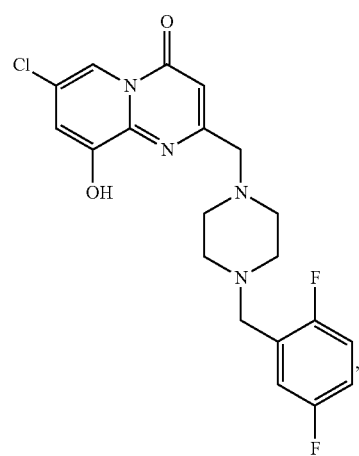

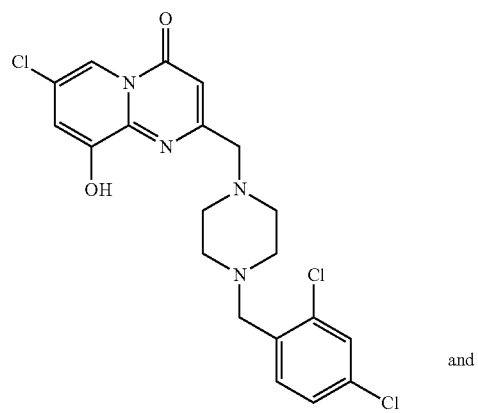

and

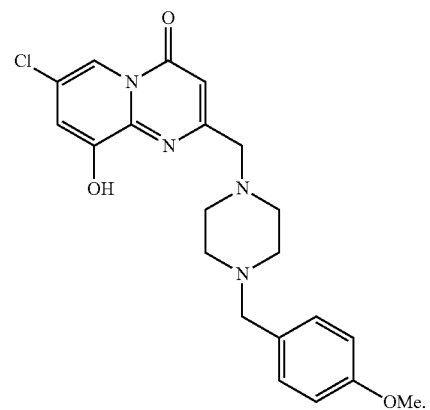

5. A compound of formula II

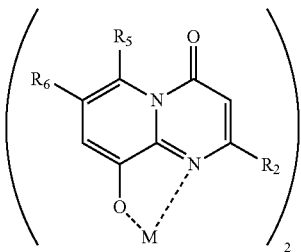

in which
$R^2$ is $(CH_2)_n NR^9 R^{10}$, $C_{1-4}$alkyl optionally interrupted with O or $(CH_2)_n SC=SNR^9 R^{10}$;
$R^5$ is H or $C_{1-4}$ alkyl;
$R^6$ is H, halo, $(CH_2)_n$ 5 or 6 membered heterocyclyl in which the heterocyclyl group is optionally substituted or $C_{2-4}$ alkynyl; provided that one of $R^5$ and $R^6$ is not hydrogen;
$R^9$ and $R^{10}$ together with the nitrogen atom to which they are attached form a 5 or 6 membered heterocyclyl in which the heterocyclyl group is optionally substituted;
n is 0, 1, 2 or 3;
R and
M is transition metal;

wherein optional substituents are selected from $C_{1-6}$ alkyl, $C_{3-6}$ cycloalkyl, $C_{2-6}$ alkenyl, $C_{2-6}$ alkynyl, aryl, heterocyclyl, halo, halo$C_{1-6}$alkyl, $CF_3$, halo$C_{3-6}$cycloalkyl, halo$C_{2-6}$alkenyl, halo$C_{2-6}$alkynyl, haloaryl, haloheterocycylyl, hydroxy, $C_{1-6}$ alkoxy, $OCF_3$, $C_{2-6}$alkenyloxy, $C_{2-6}$alkynyloxy, aryloxy, heterocyclyloxy, carboxy, halo$C_{1-6}$alkoxy, halo$C_{2-6}$alkenyloxy, halo$C_{2-6}$alkynyloxy, haloaryloxy, nitro, nitro$C_{1-6}$alkyl, nitro$C_{2-6}$alkenyl, nitroaryl, nitroheterocyclyl, azido, amino, $C_{1-6}$alkylamino, $C_{2-6}$alkenylamino, $C_{2-6}$alkynylamino, arylamino, heterocyclylamino acyl $C_{1-6}$alkylacyl, $C_{2-6}$alkenylacyl, $C_{2-6}$alkynylacyl, arylacyl, heterocyclylacyl, acylamino, acyloxy, aldehydo, $C_{1-6}$alkylsulphonyl, arylsulphonyl, $C_{1-6}$alkylsulphonylamino, arylsulphonylamino, $C_{1-6}$alkylsulphonyloxy, arylsulphonyloxy, $C_{1-6}$alkylsulphenyl, $C_{2-6}$alklysulphenyl, arylsulphenyl, carboalkoxy, carboaryloxy, mercapto, $C_{1-6}$alkylthio, arylthio, acylthio and cyano;
each 5 or 6 membered heterocyclyl group may have 1, 2, 3 or 4 heteroatoms selected from O, S and N and may be saturated, unsaturated or aromatic;
or a pharmaceutically acceptable salt, stereoisomer or geometric isomer thereof.

6. A pharmaceutical agent comprising an effective amount of the compound according to claim 1, or a pharmaceutically acceptable salt or stereoisomer or geometric isomer thereof and a pharmaceutically acceptable carrier.

* * * * *